United States Patent [19]
Pittet et al.

[11] Patent Number: 6,019,851
[45] Date of Patent: Feb. 1, 2000

[54] PRODUCING TASTANDS INCLUDING FOOD AND BEVERAGE ADDITIVES

[75] Inventors: Alan Owen Pittet, Colts Neck; Kevin P. Miller, Middletown; Marvin Schulman, Howell; Ranya Muralidhara, Fair Haven; William J. Kinlin, Middletown; Carlos Ramirez, Iselin, all of N.J.; Michael F. Javes, Merton, Wis.

[73] Assignee: International Flavors & Fragrances Inc., New York, N.Y.

[21] Appl. No.: 09/305,485

[22] Filed: May 6, 1999

Related U.S. Application Data

[62] Division of application No. 09/038,945, Mar. 12, 1998.

[51] Int. Cl.[7] .............................. C13D 1/00; C13D 1/02; C13D 1/04; C13D 1/08; A23L 1/00
[52] U.S. Cl. .................................. 127/2; 99/537; 99/584; 127/42
[58] Field of Search .............................. 99/509–511, 537, 99/538, 584; 127/2, 42, 43, 53–56, 6; 83/168, 569, 425, 856; 152/7; 156/259; 422/276; 241/260, 222, 60, 62; 426/548, 597, 242, 655, 443, 466, 533, 435, 650, 496

[56] References Cited

U.S. PATENT DOCUMENTS

| | | | |
|---|---|---|---|
| 3,690,358 | 9/1972 | Tilby | 99/510 X |
| 3,713,469 | 1/1973 | Dietzel | 99/537 X |
| 3,926,662 | 12/1975 | Rundell | 127/57 X |
| 3,976,498 | 8/1976 | Tilby et al. | 127/2 |
| 4,033,755 | 7/1977 | Nickell | 127/42 X |
| 4,063,960 | 12/1977 | Paley | 127/42 |
| 4,151,004 | 4/1979 | Vukelic | 127/2 |
| 4,572,741 | 2/1986 | Mason | 127/2 |
| 4,636,263 | 1/1987 | Cundiff | 127/42 |
| 4,743,307 | 5/1988 | Mason | 127/2 |
| 5,173,122 | 12/1992 | Tilby et al. | 127/2 |
| 5,468,300 | 11/1995 | Monclin | 127/42 X |
| 5,468,301 | 11/1995 | Monclin | 127/43 |

*Primary Examiner*—Timothy Simone
*Attorney, Agent, or Firm*—Arthur L. Liberman

[57] ABSTRACT

Described is a process for producing one or more tastands including food and beverage additives from *Saccharum officinarum* leaves (sugarcane leaves) by means of carrying out one or more physical separation unit operations on a plurality of such leaves, macerates thereof or mixtures of leaves and macerates thereof whereby one or more natural food additives is separated and isolated from the remainder of the plurality of leaves, macerates thereof or mixtures of leaves and macerates thereof. Such unit operations include pressurization using hydraulic press means, steam distillation, fractional distillation, supercritical carbon dioxide extraction, volatile solvent extraction and/or charcoal column separation means. Also described is apparatus for carrying out such processes as well as the products produced using such processes and organoleptic uses of such products. Also described are compositions comprising (a) such tastands in admixture with (b) an eatable having a bitter and/or metallic taste. The eatable is any ingested material taken by mammals, such as foodstuffs, non-calorie food components or medicines including bitter chocolate or a drug such as ibuprofen.

8 Claims, 42 Drawing Sheets

FIG. 1-A
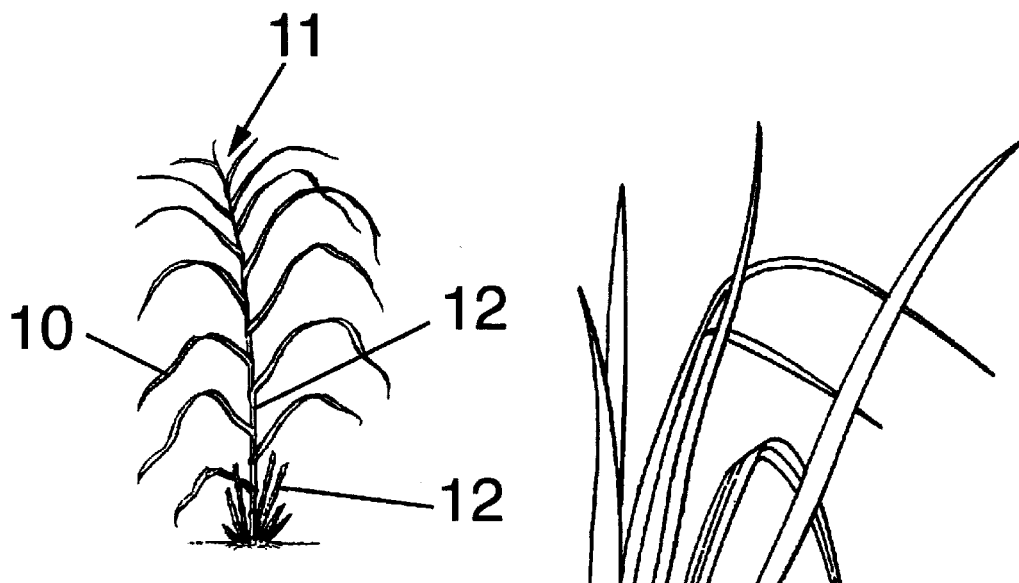
FIG. 1-B
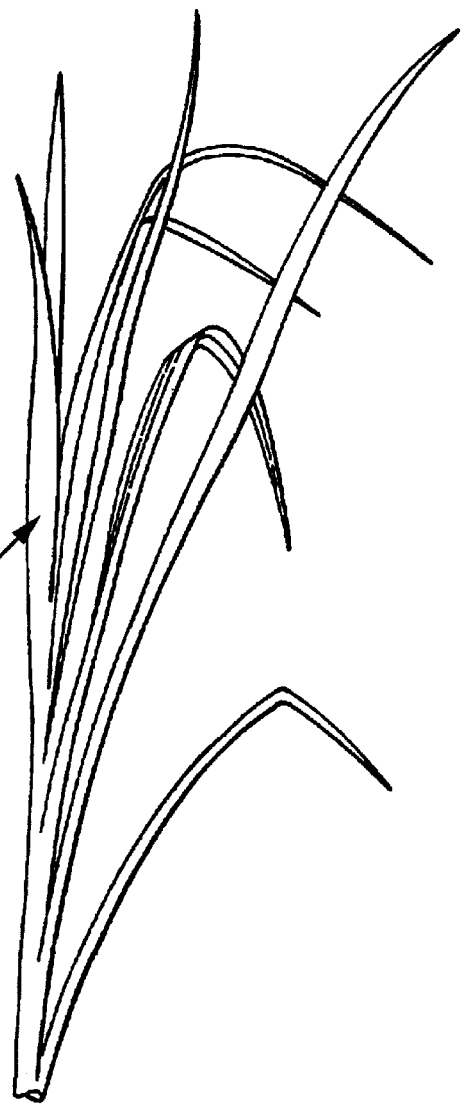

FIG. 1-C
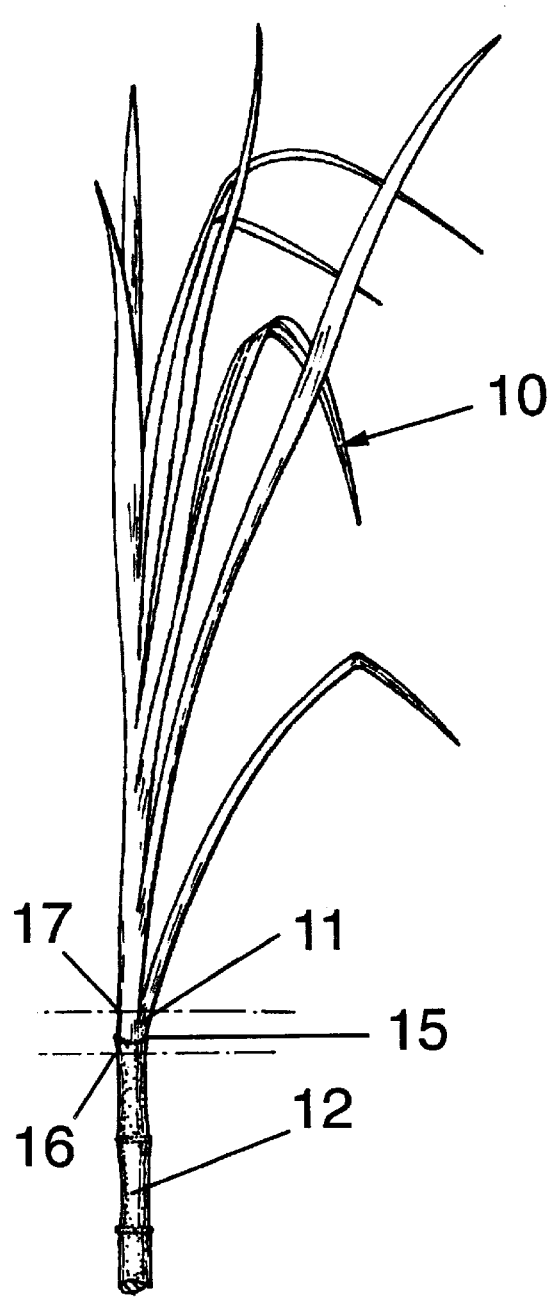
FIG. 1-D
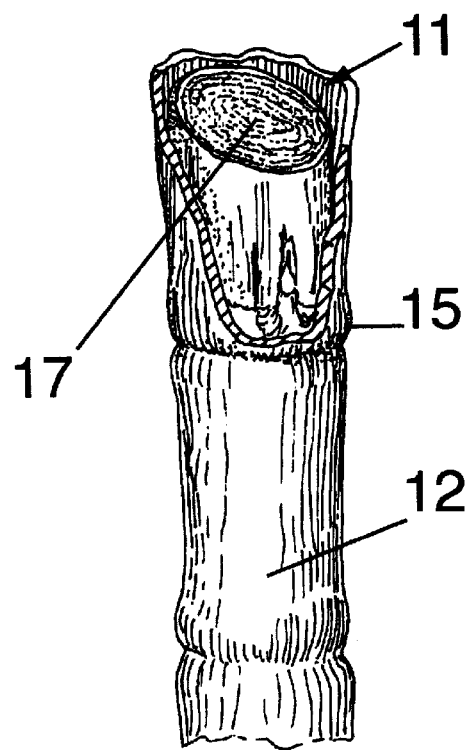
FIG. 1-E
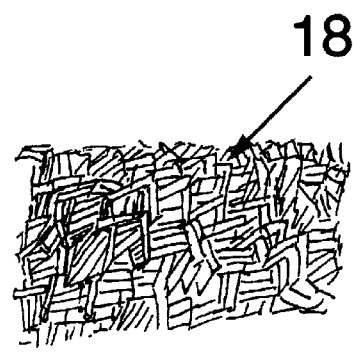

FIG. 1-F
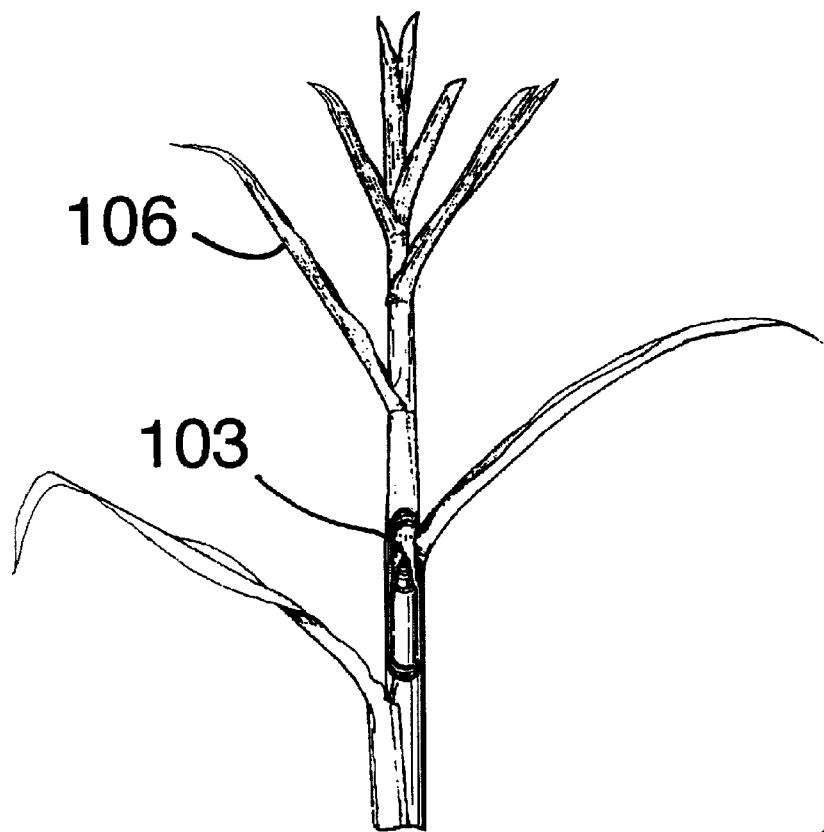
FIG. 1-G
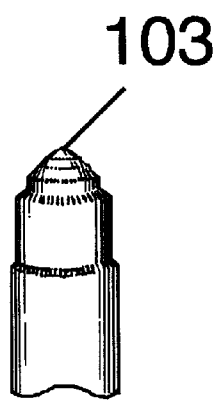

FIG. 1-H
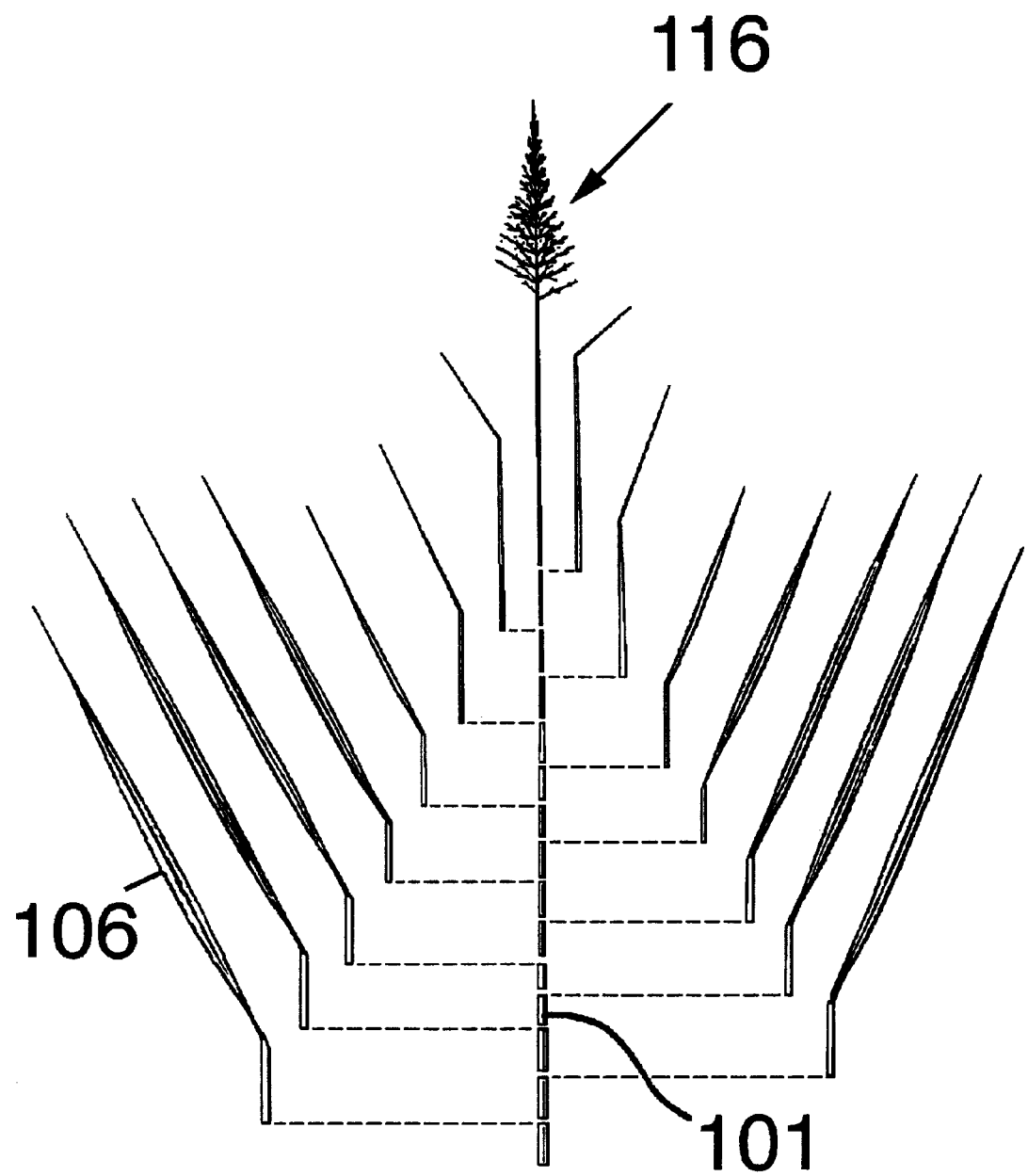

FIG. 1-I
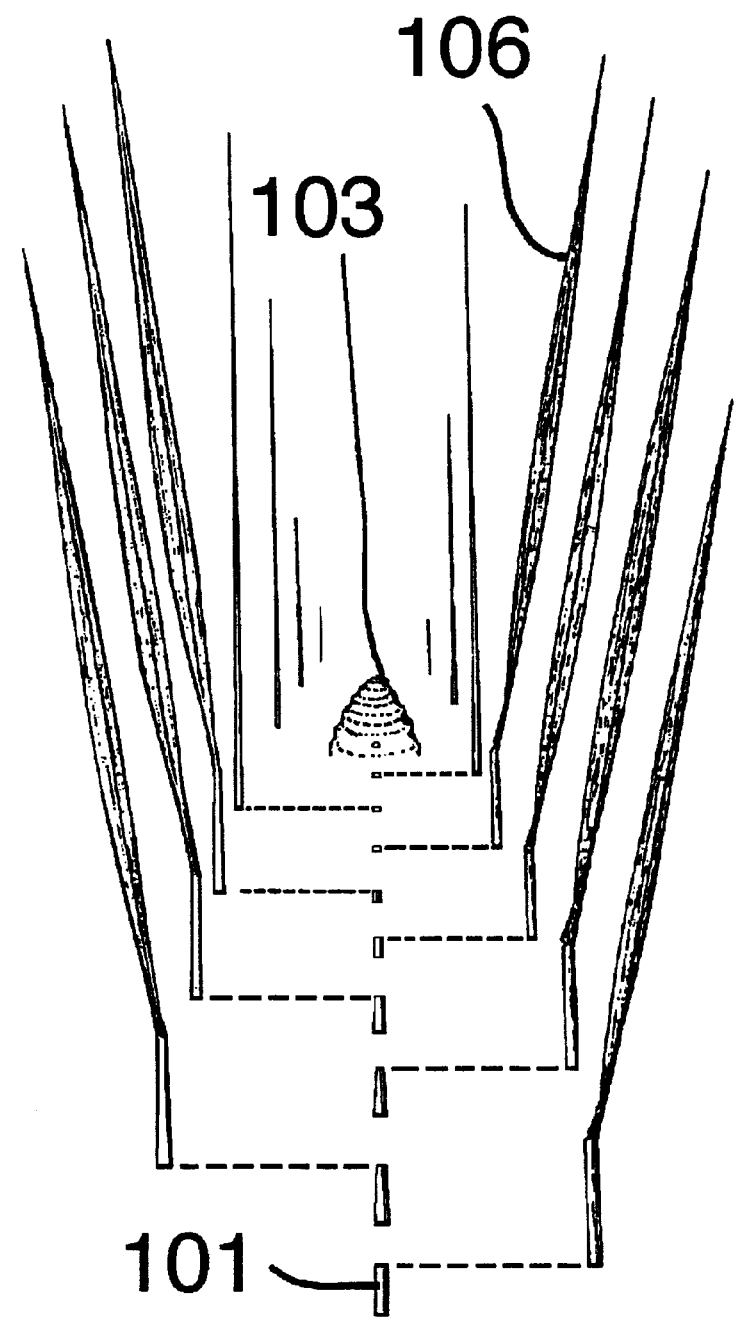

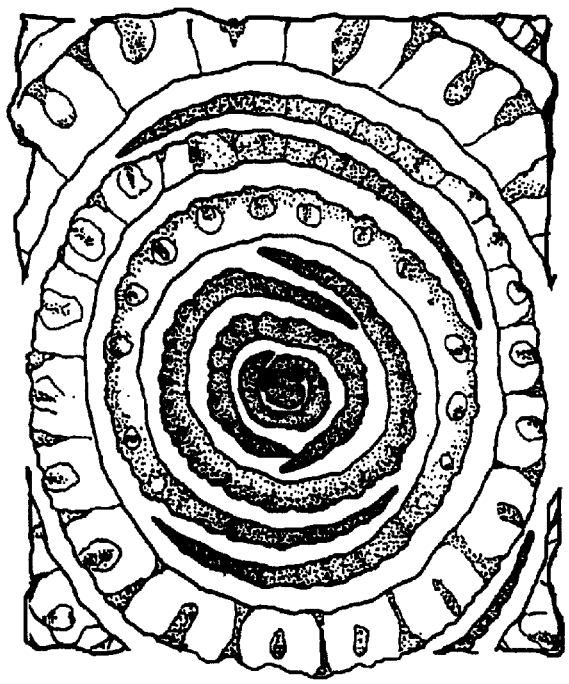
FIG. 1-J
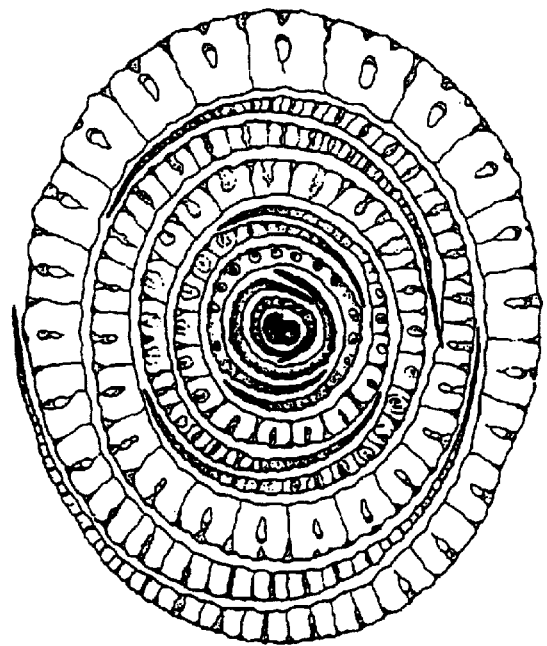
FIG. 1-K

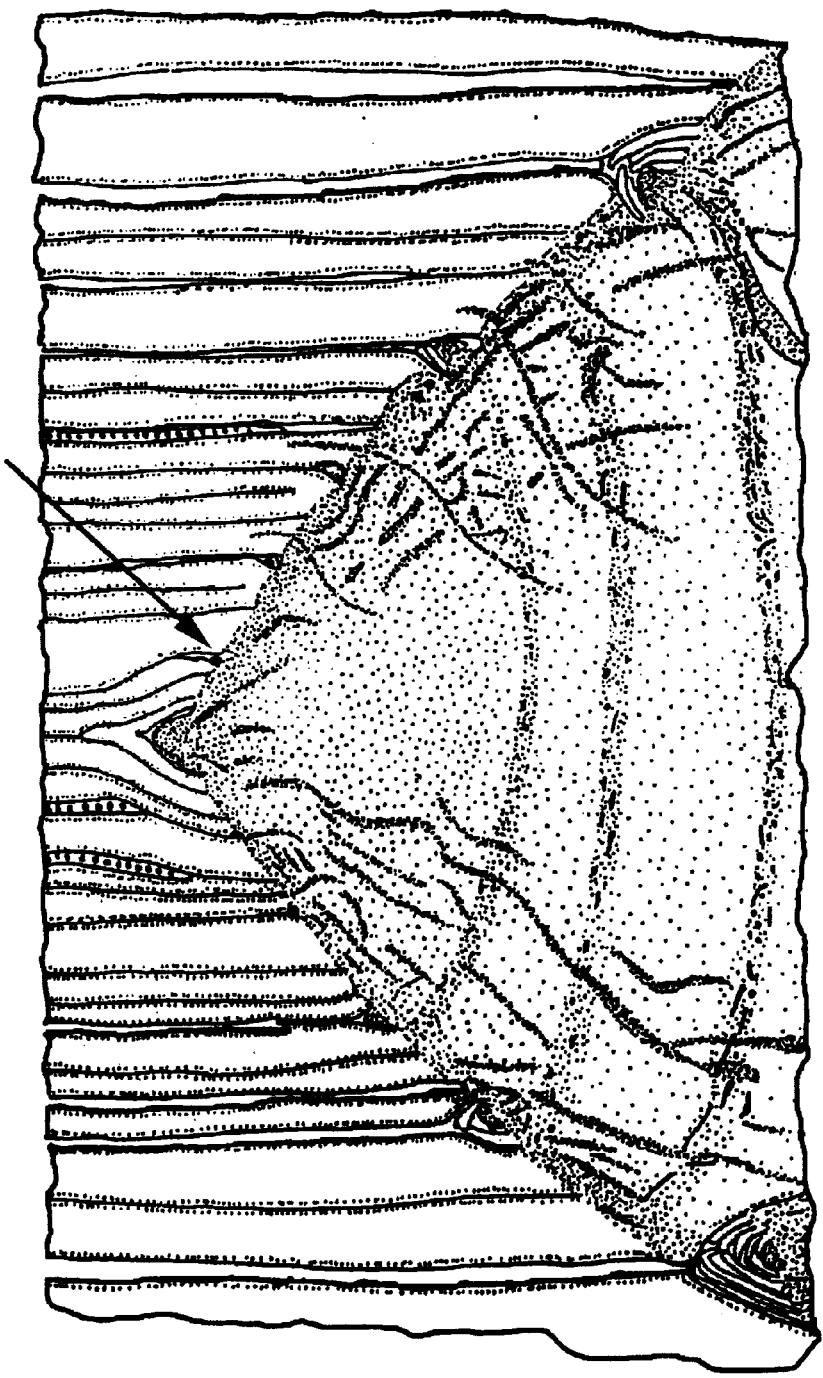
FIG. 1-L

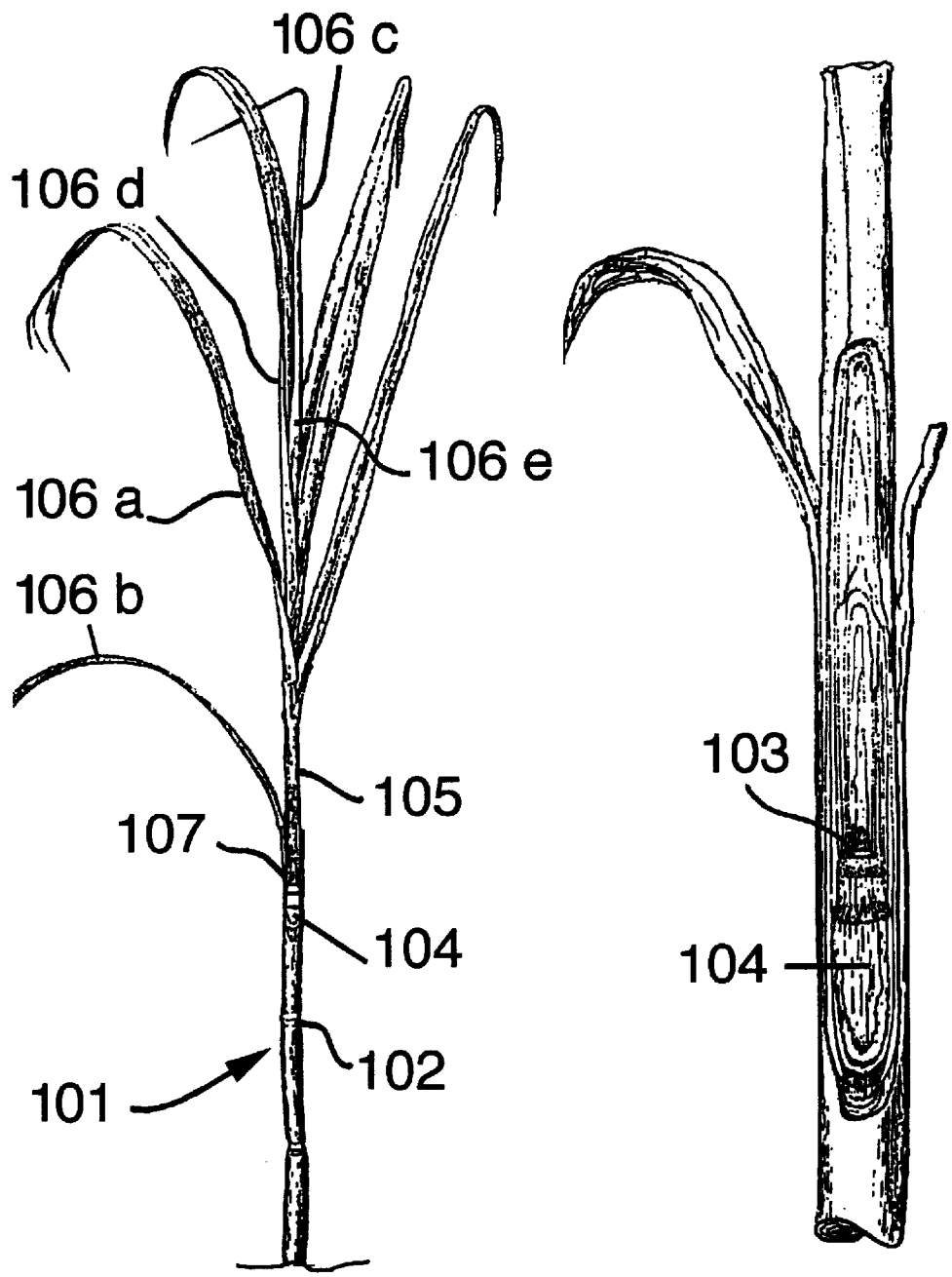

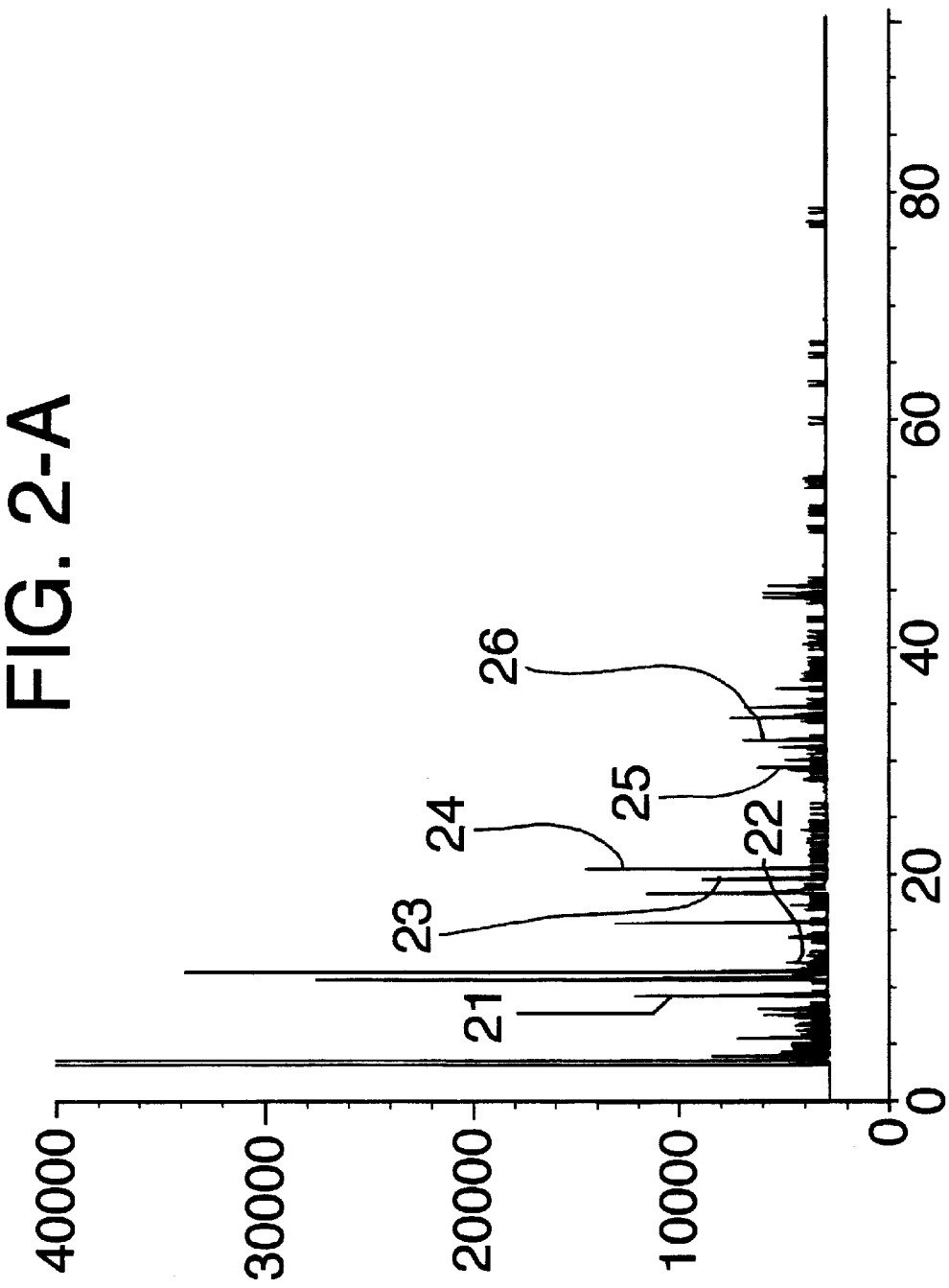

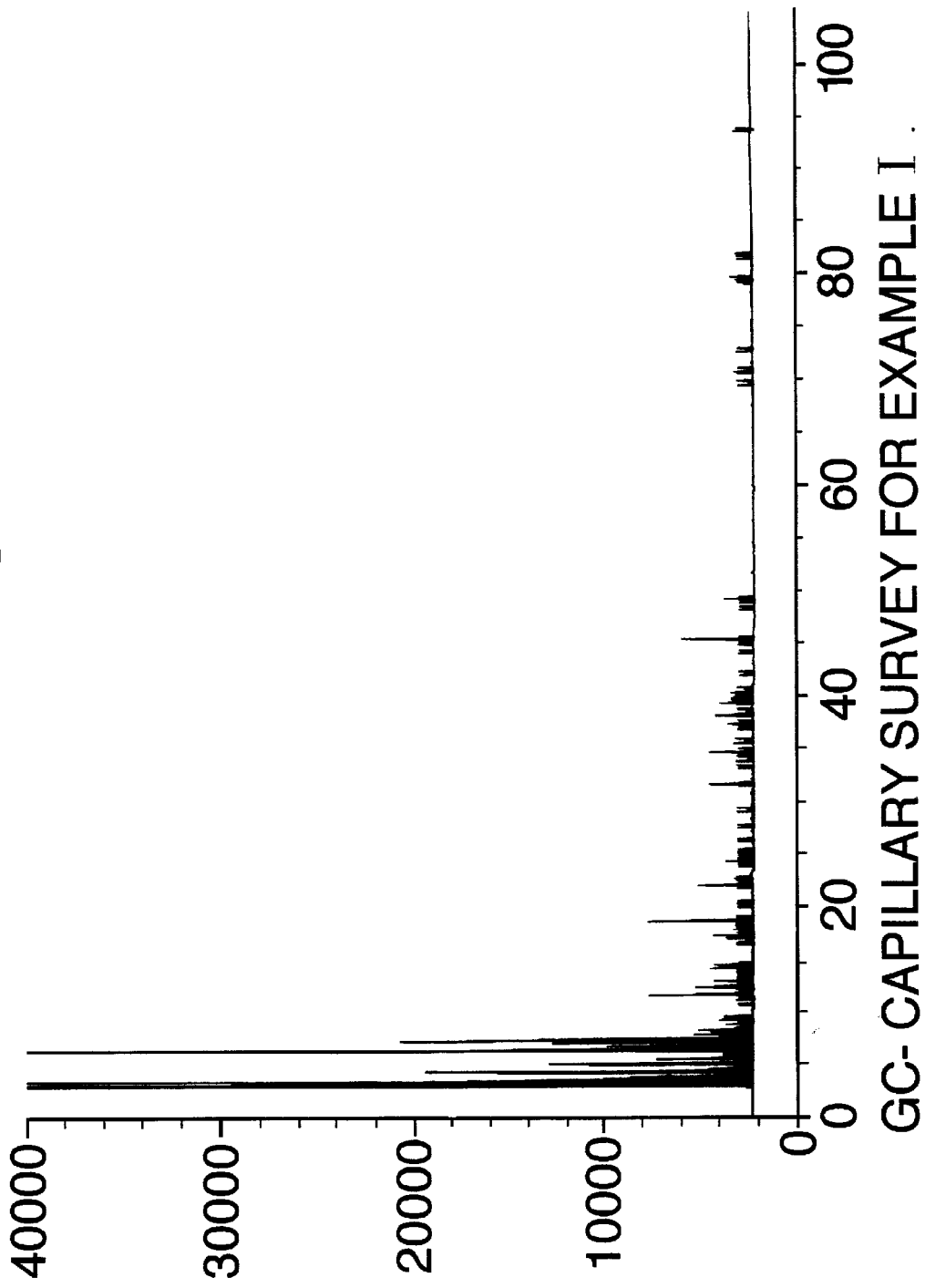
FIG. 2-B

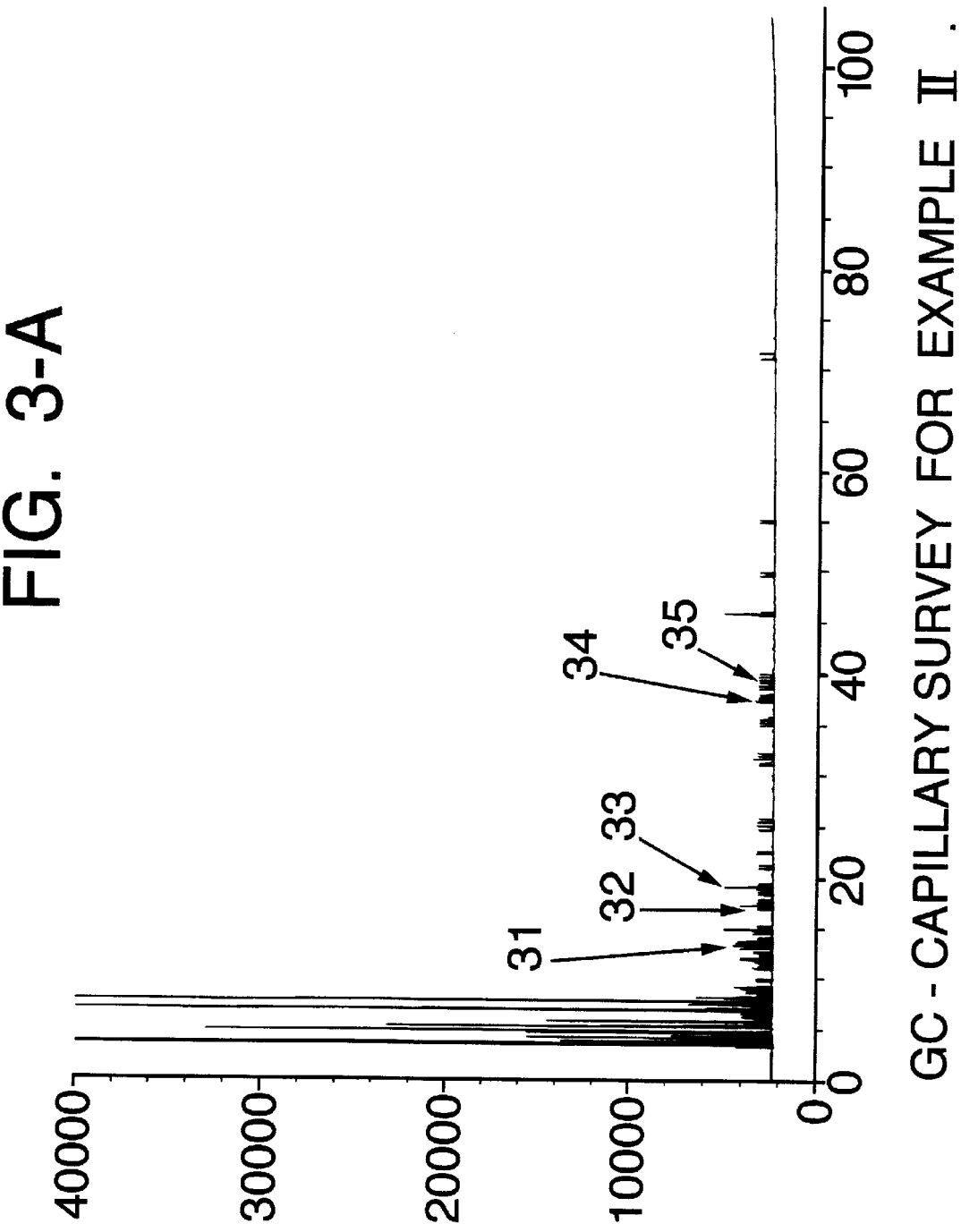
FIG. 3-A

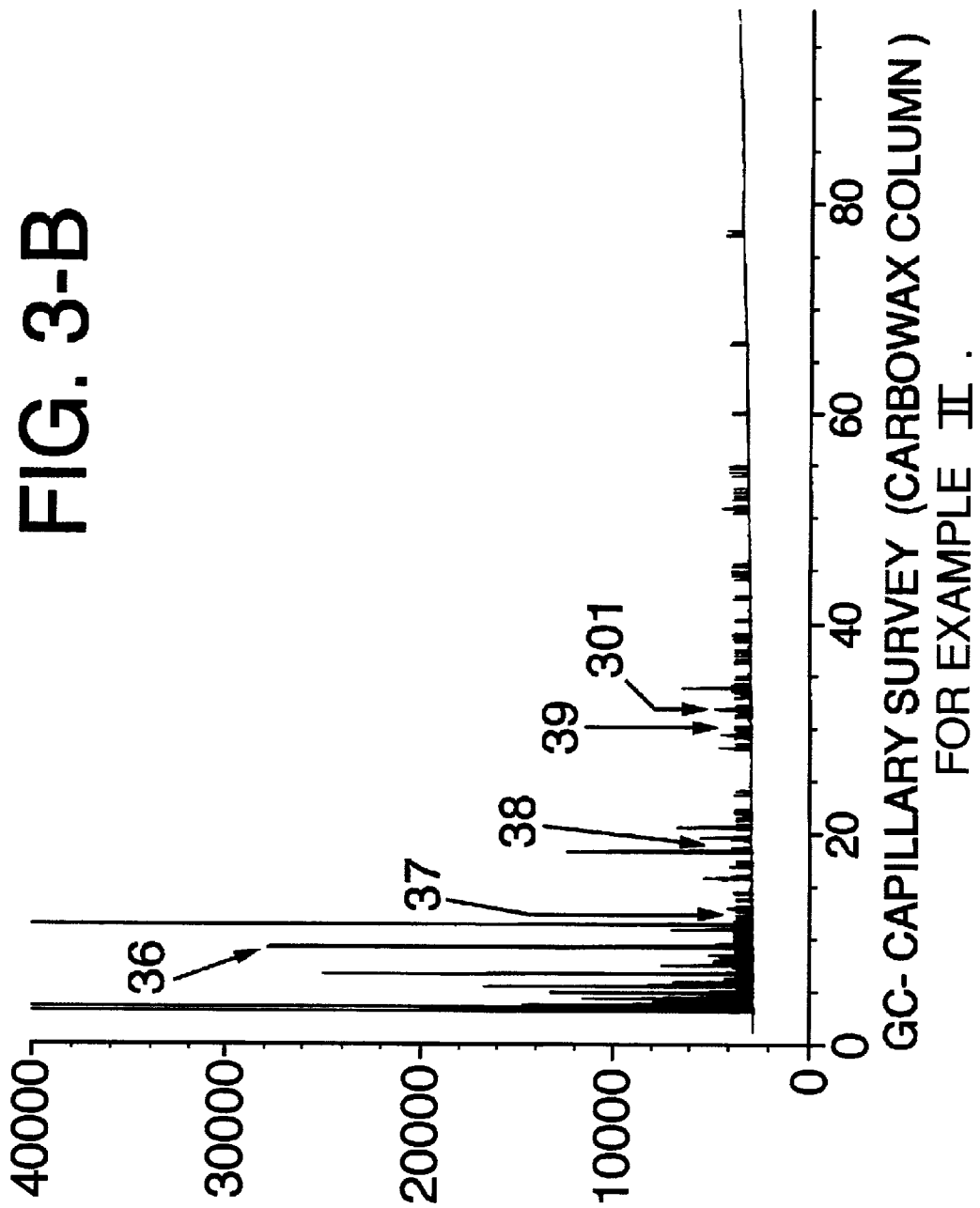

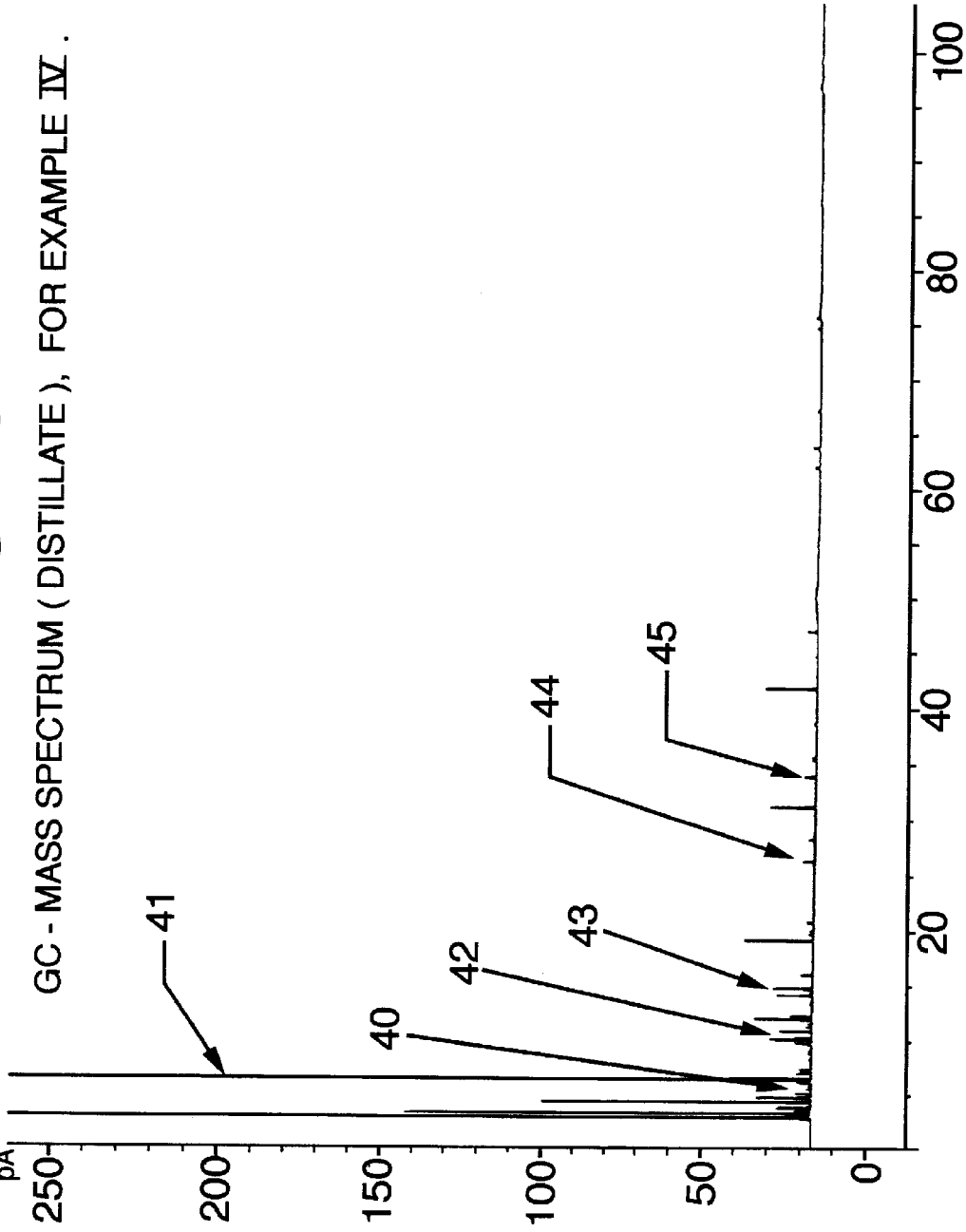

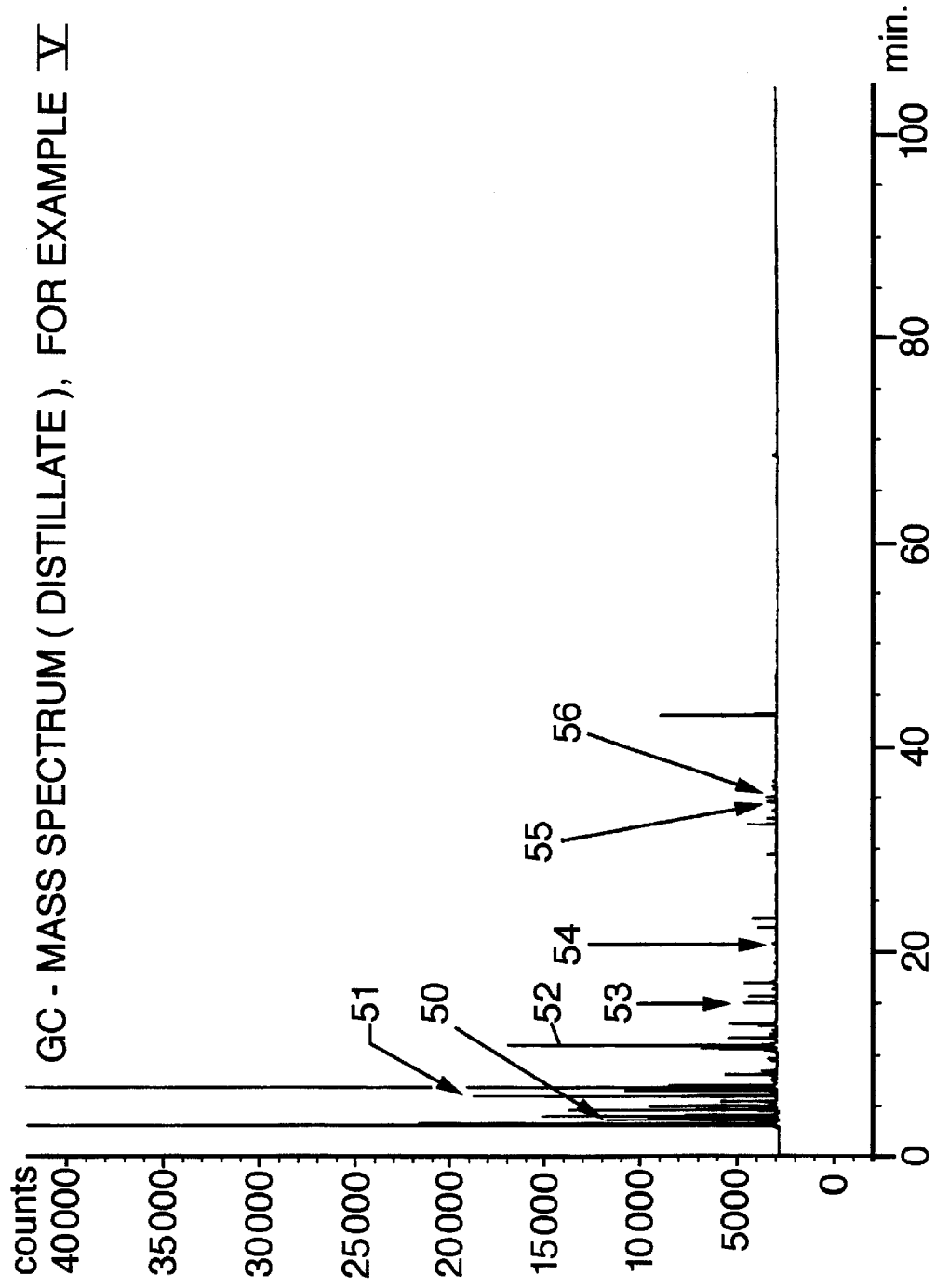
FIG. 5-A
GC - MASS SPECTRUM (DISTILLATE), FOR EXAMPLE V

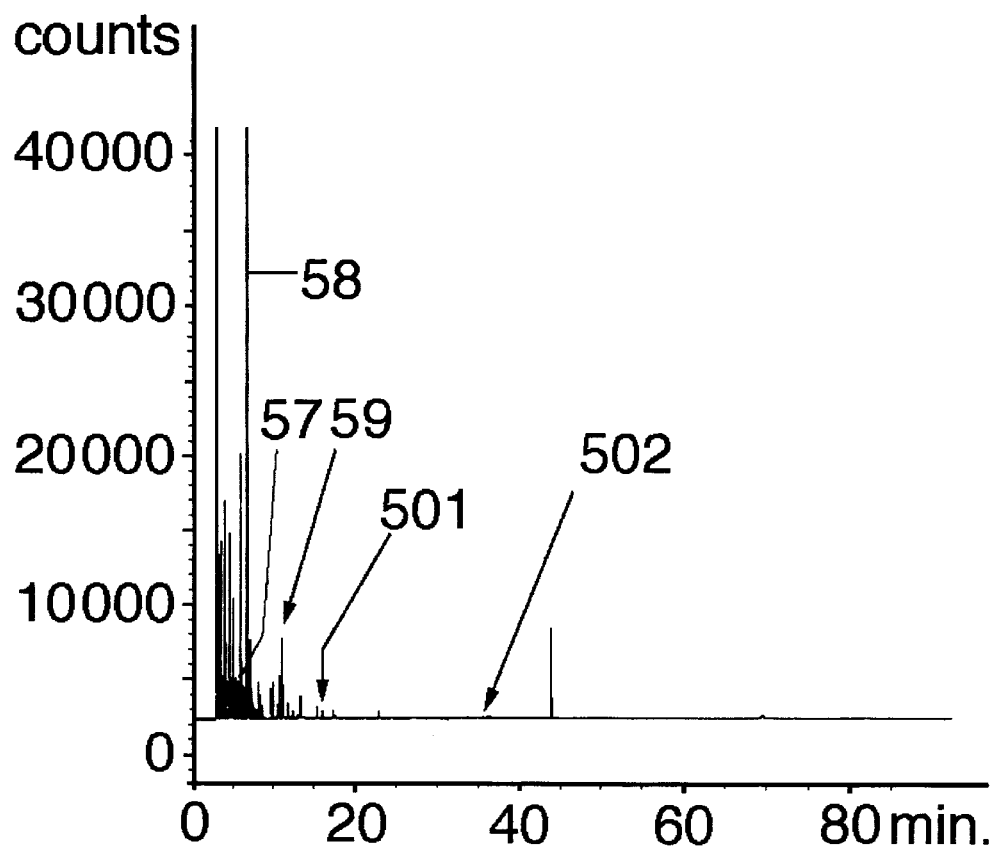
FIG.5-B
GC - MASS SPECTRUM , FOR EXAMPLE V
(PERMEATE)

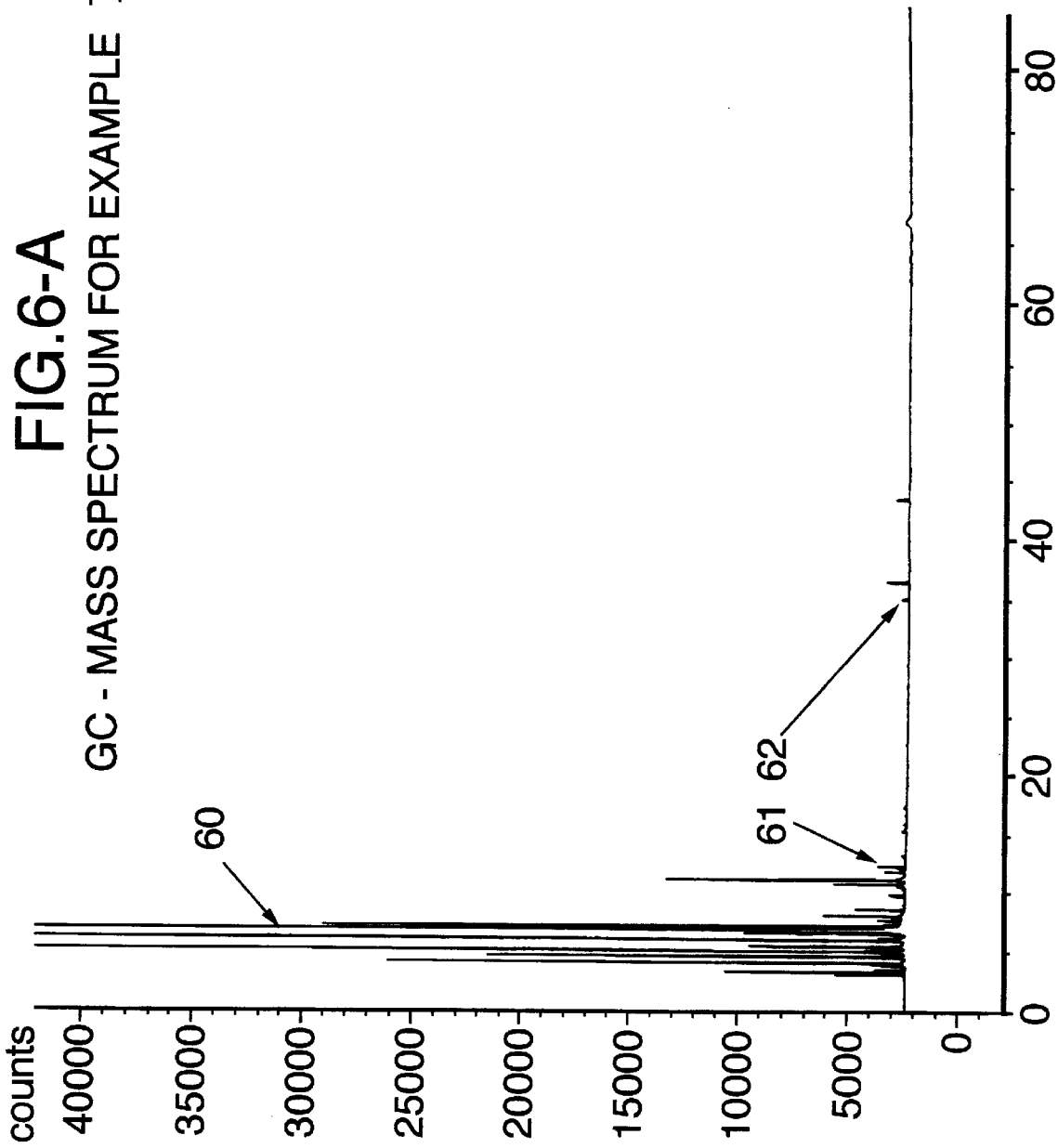

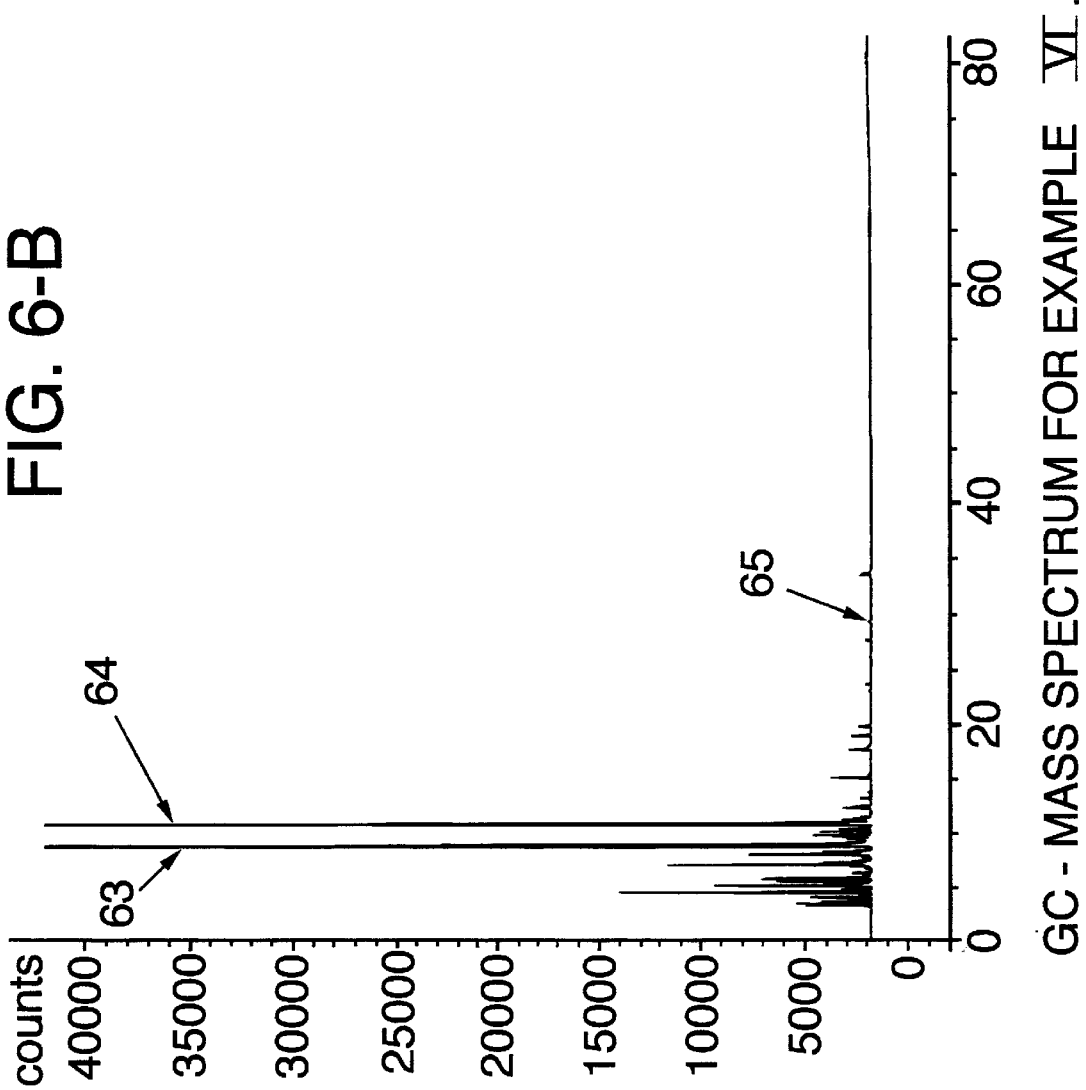
FIG. 6-B

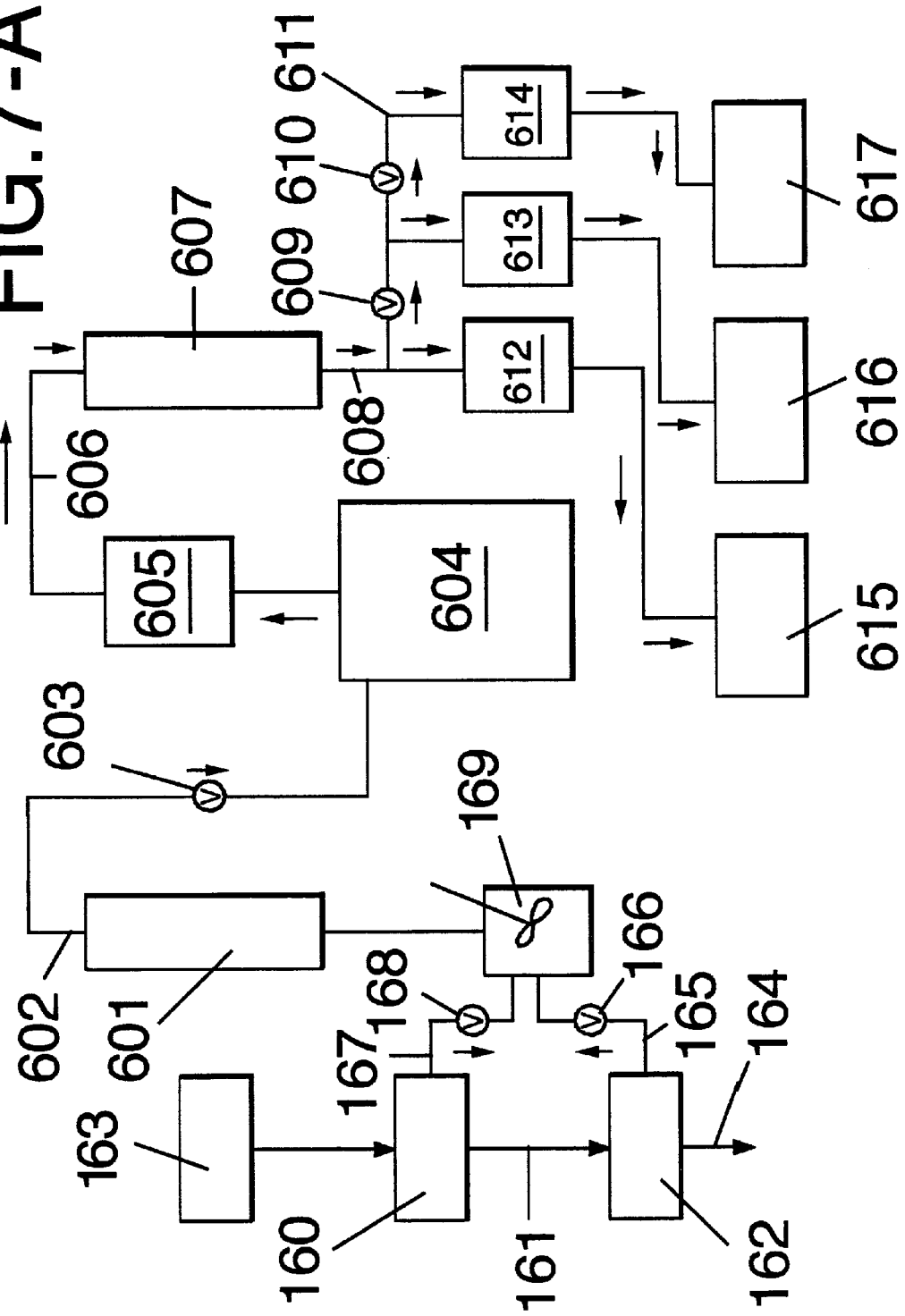
FIG.7-A

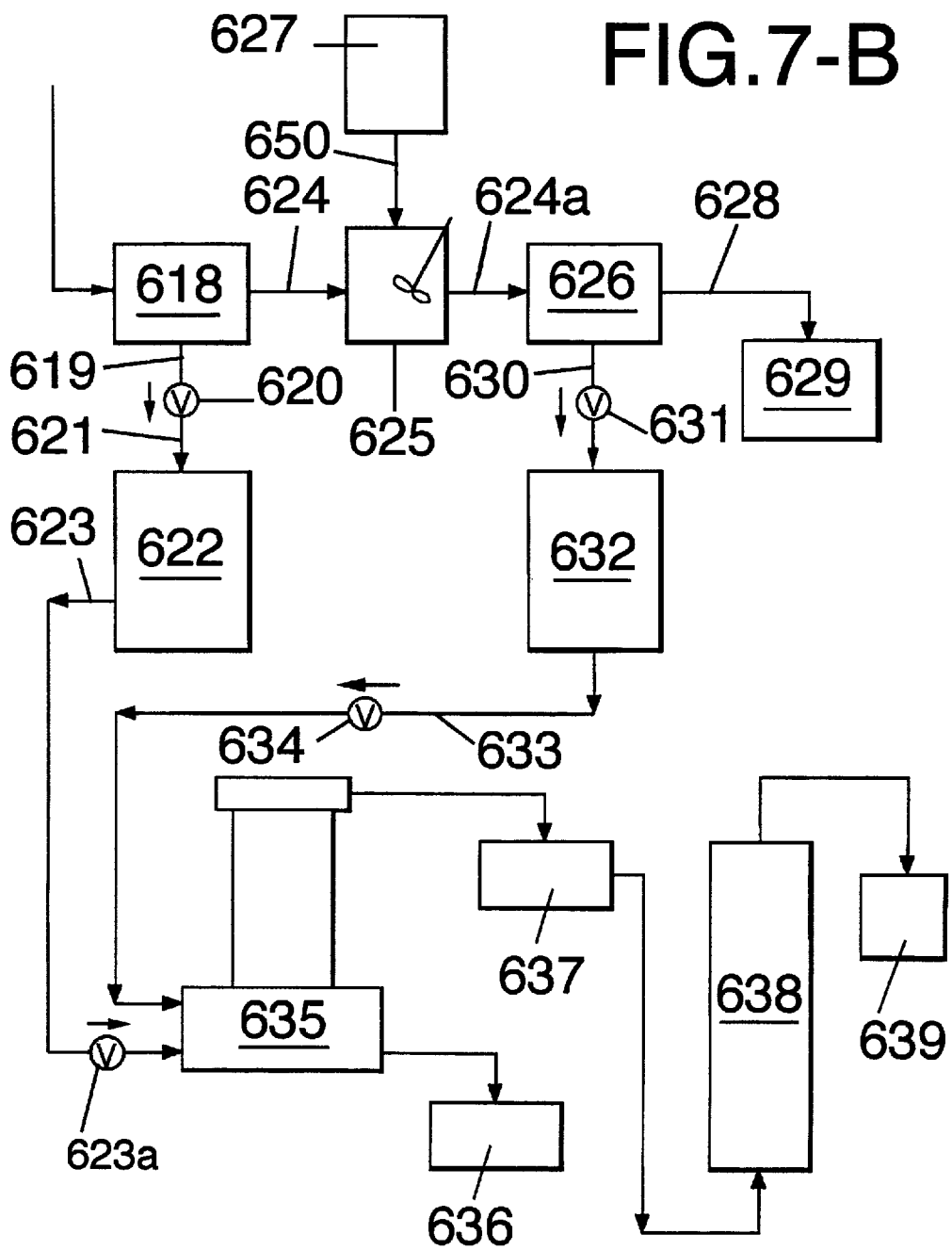
FIG.7-B

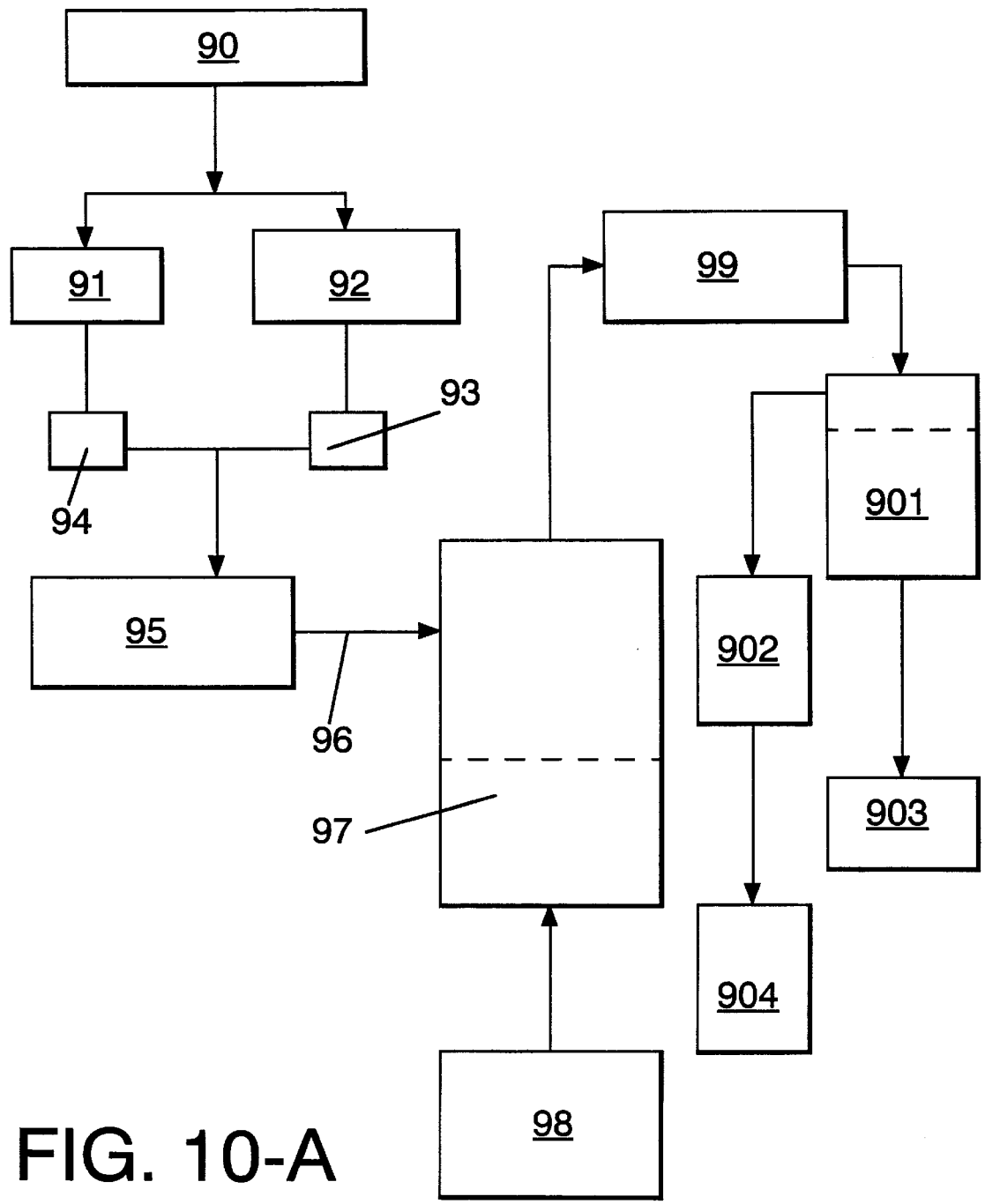
FIG. 10-A

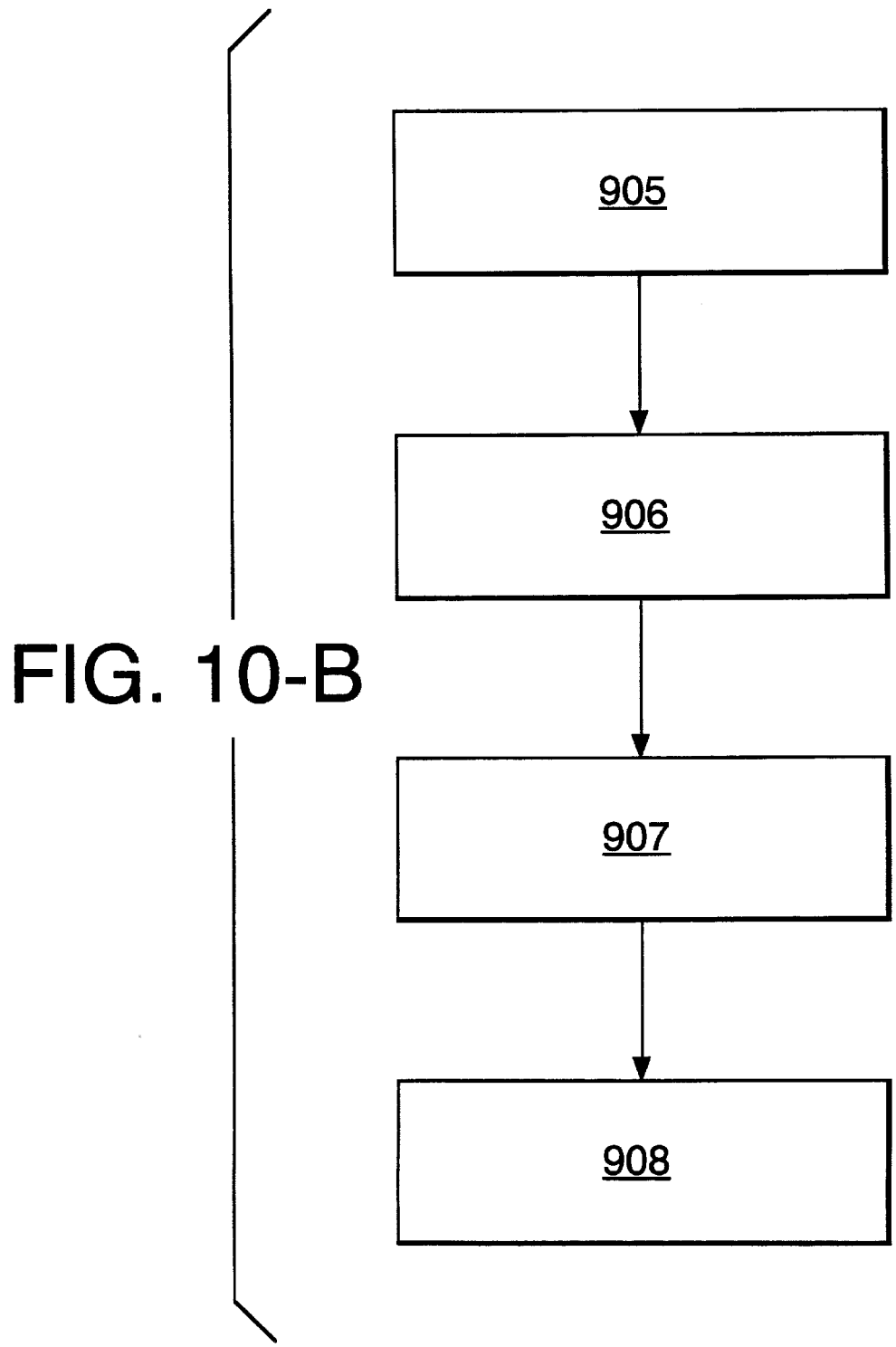
FIG. 10-B

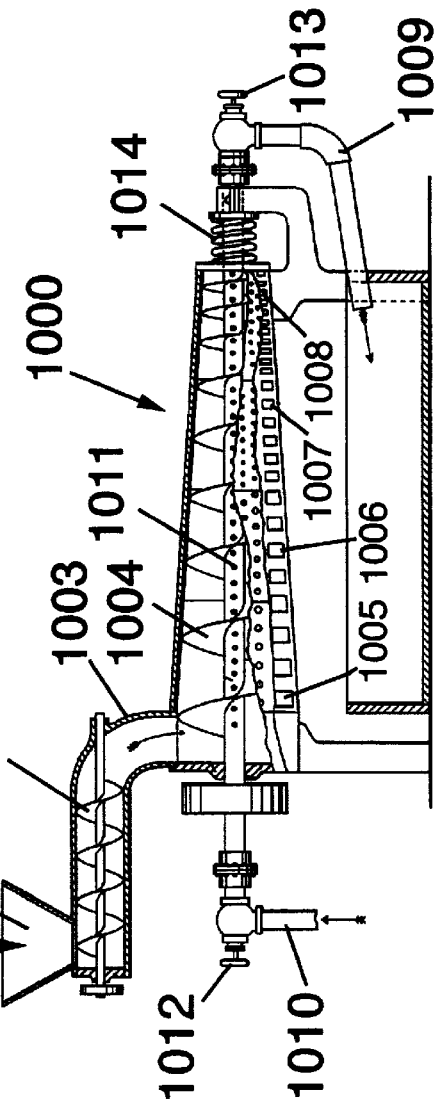

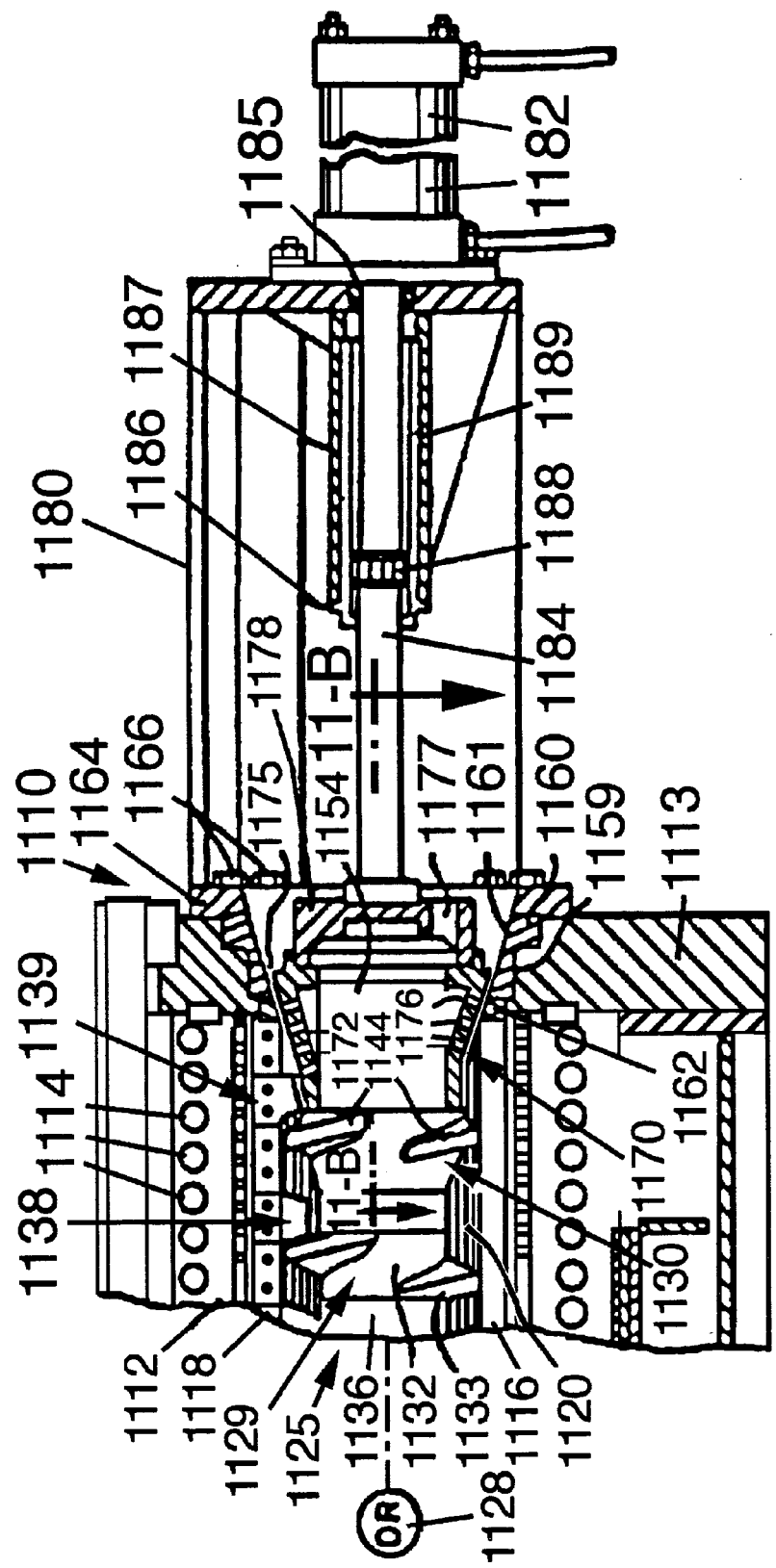
FIG. 12-A

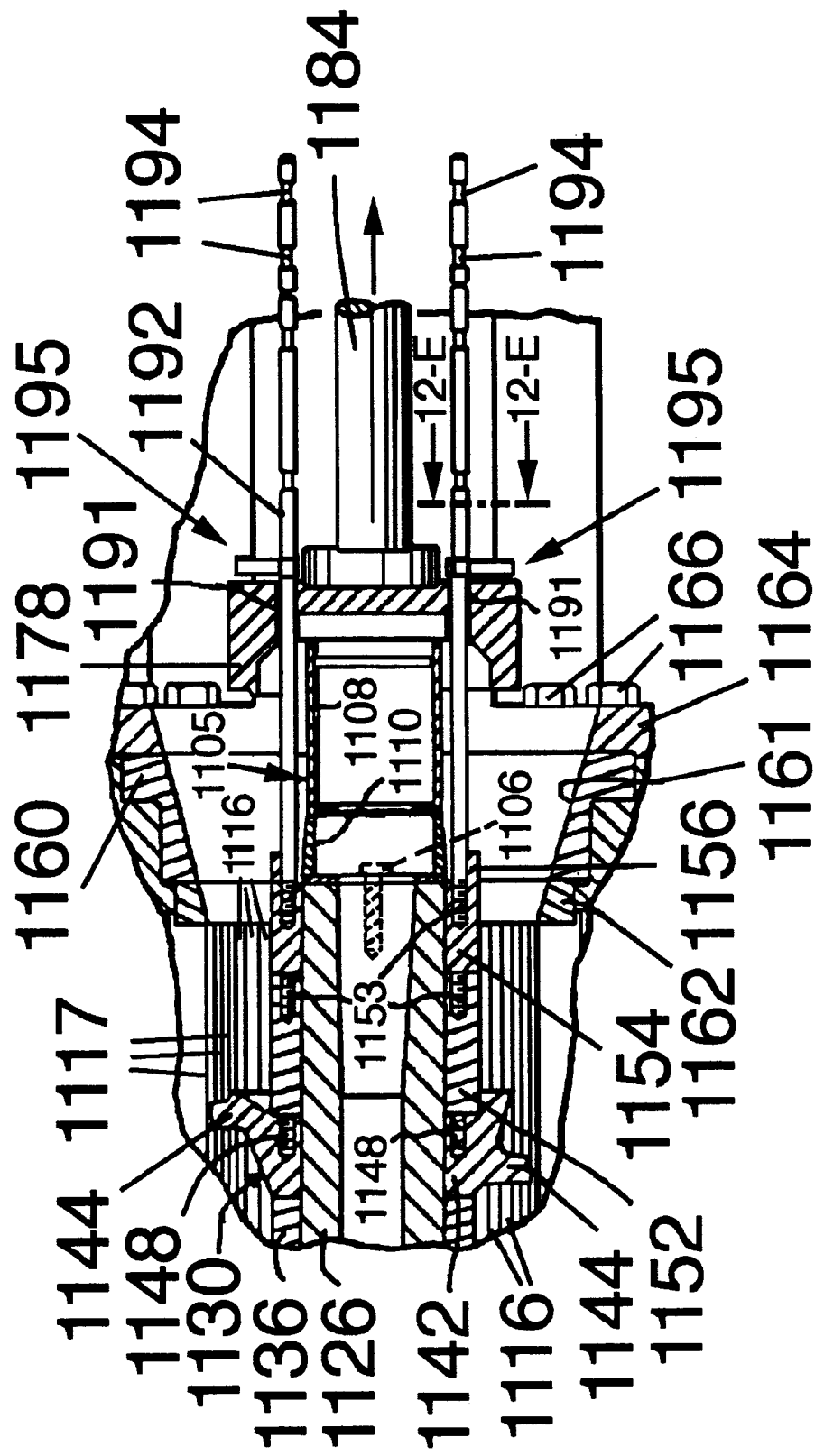
FIG. 12-B

FIG. 12-C
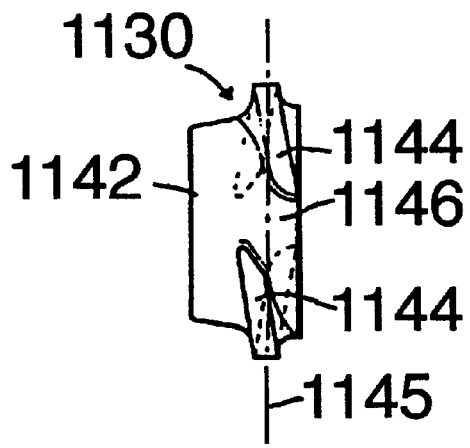
FIG. 12-D
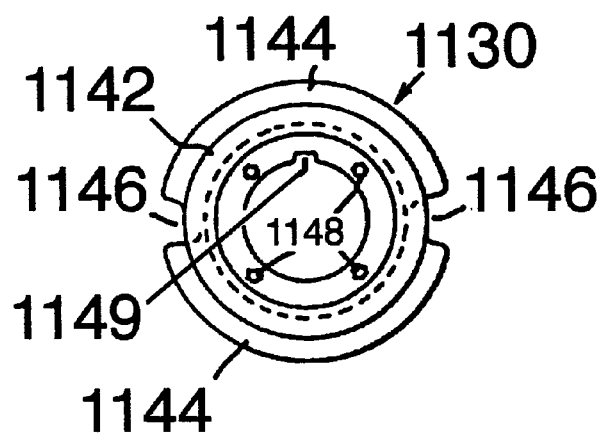
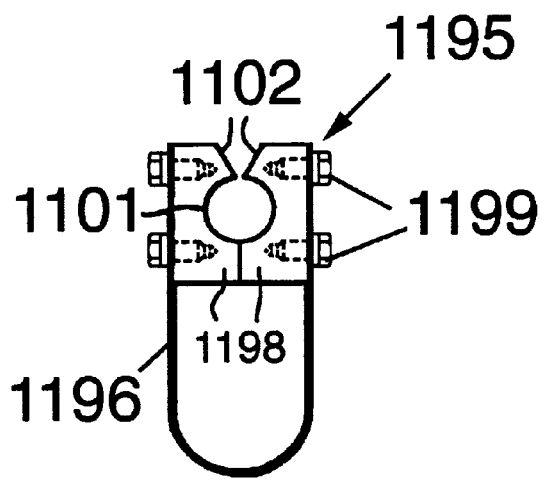
FIG. 12-E

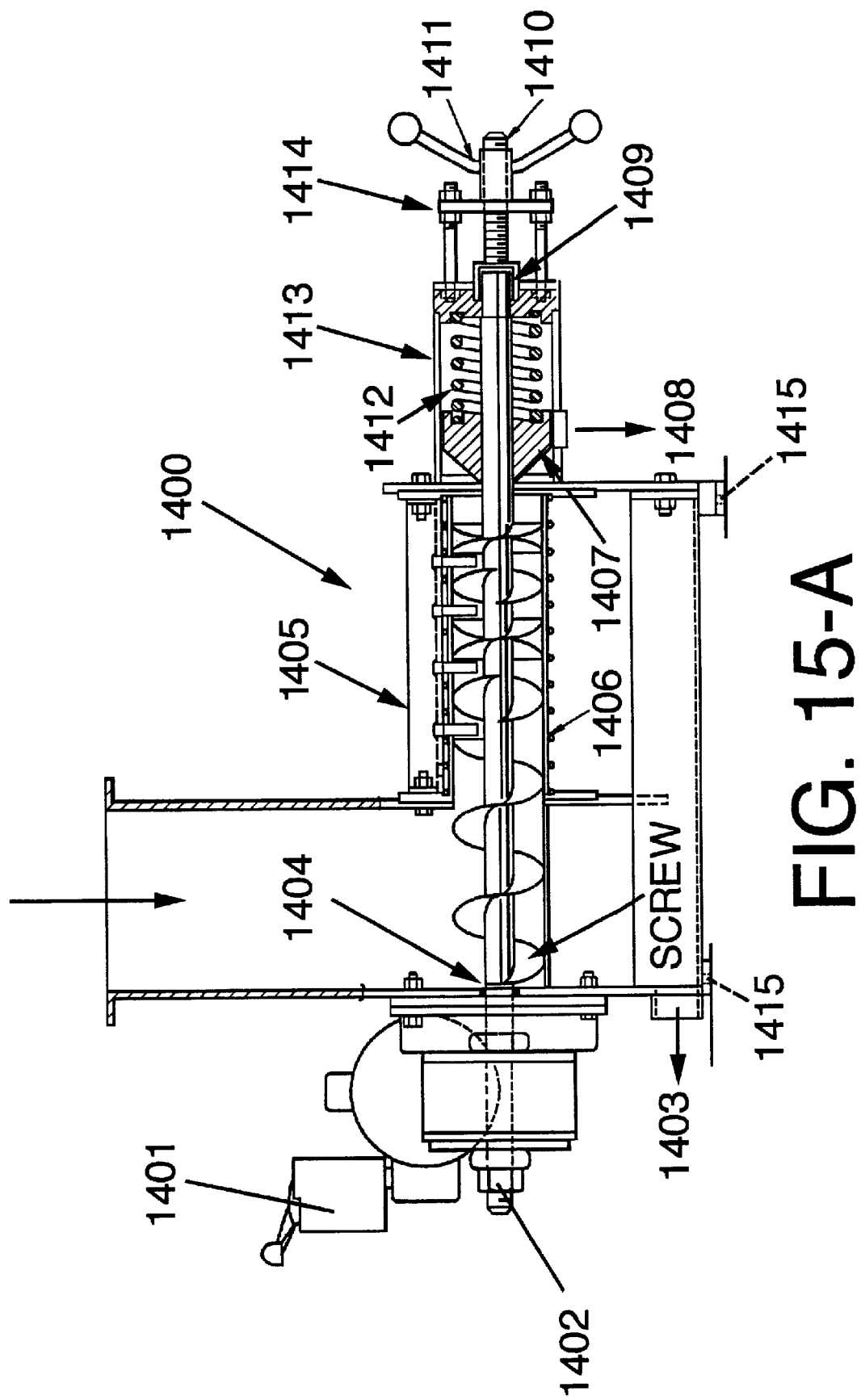
FIG. 15-A

FIG. 15-B
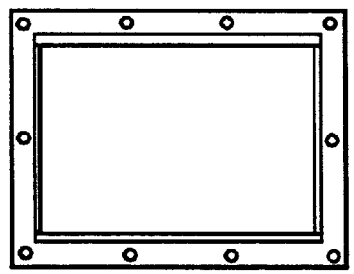
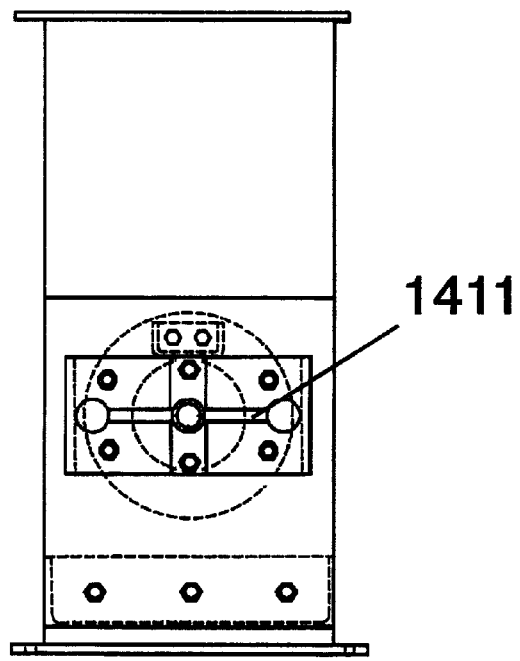
FIG. 15-C

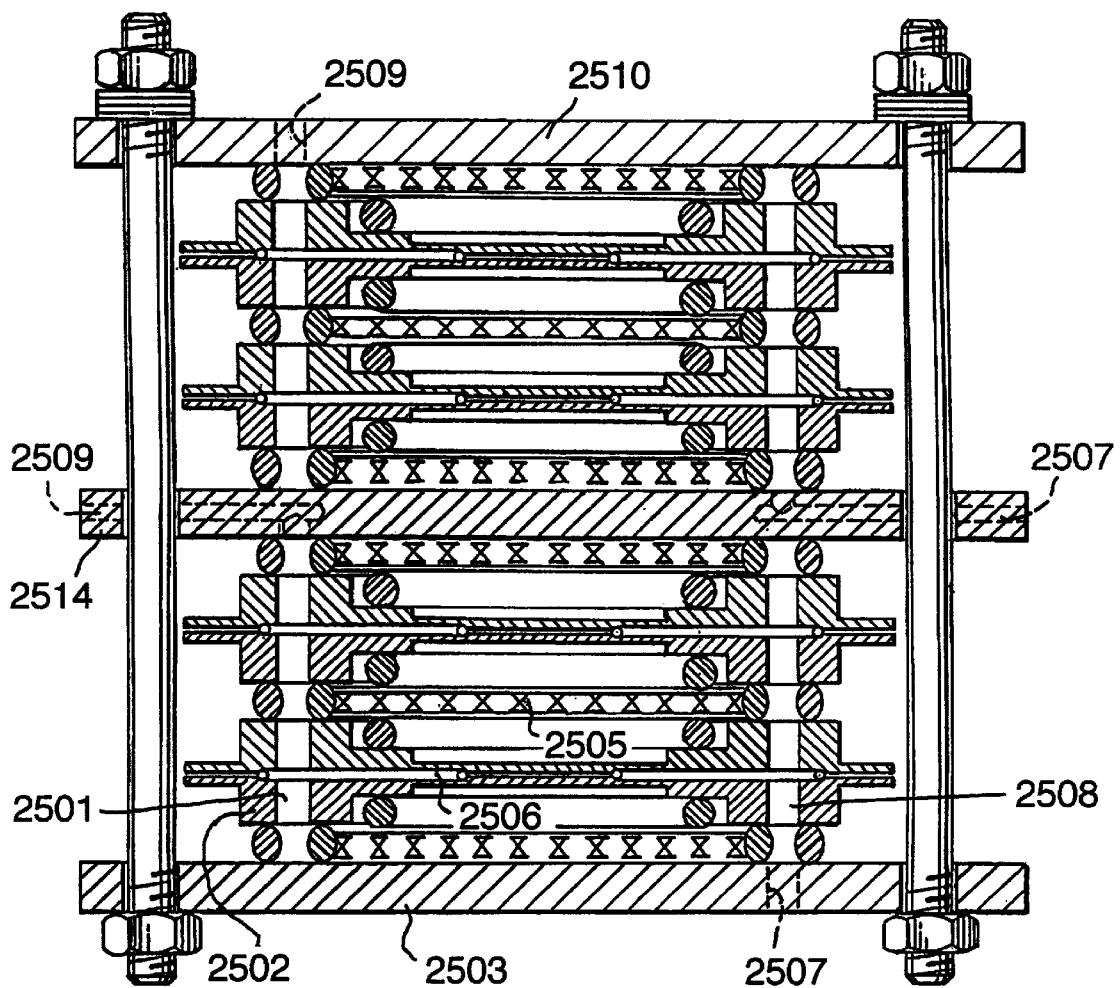
FIG. 20-A

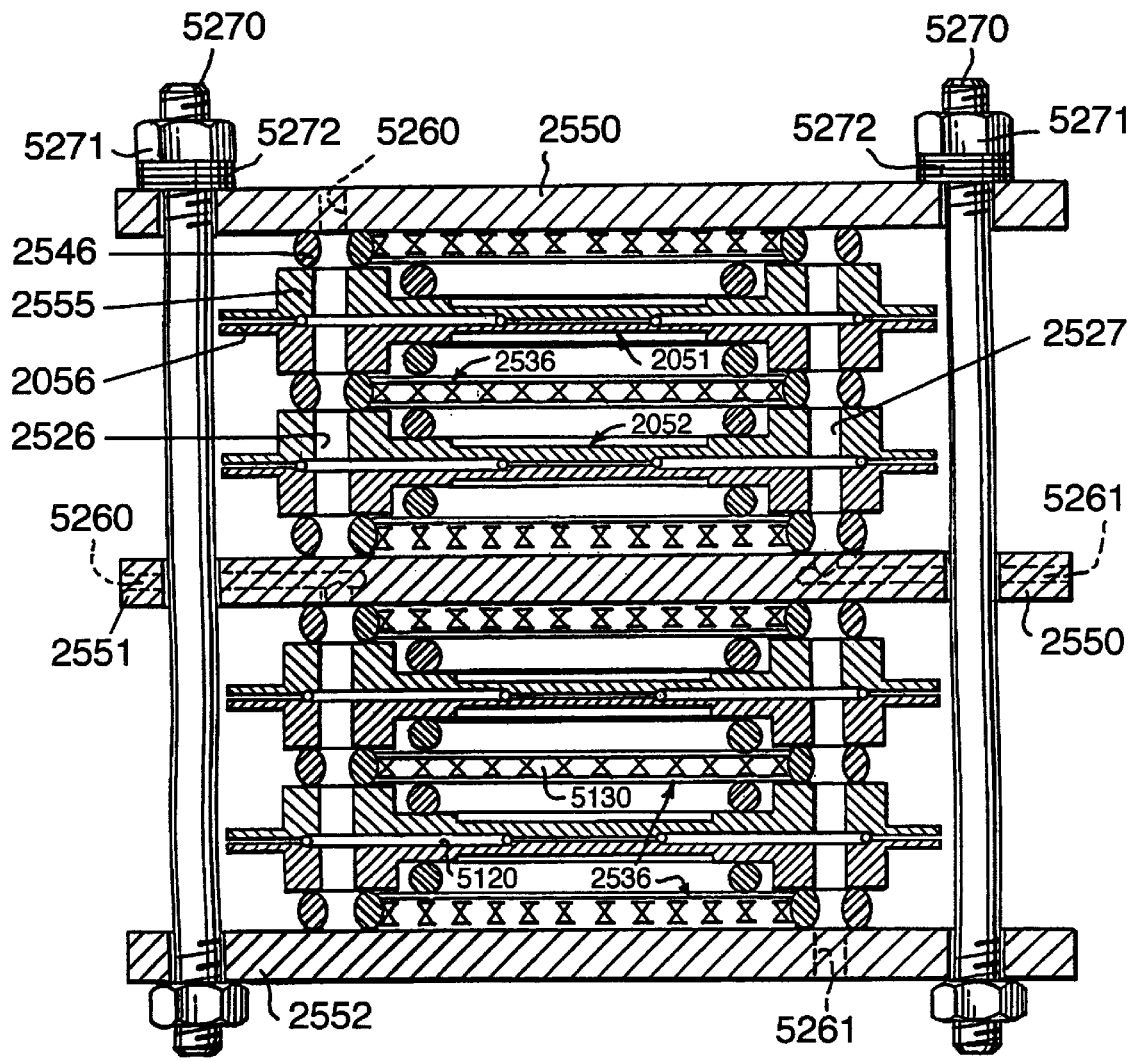
FIG. 20-B

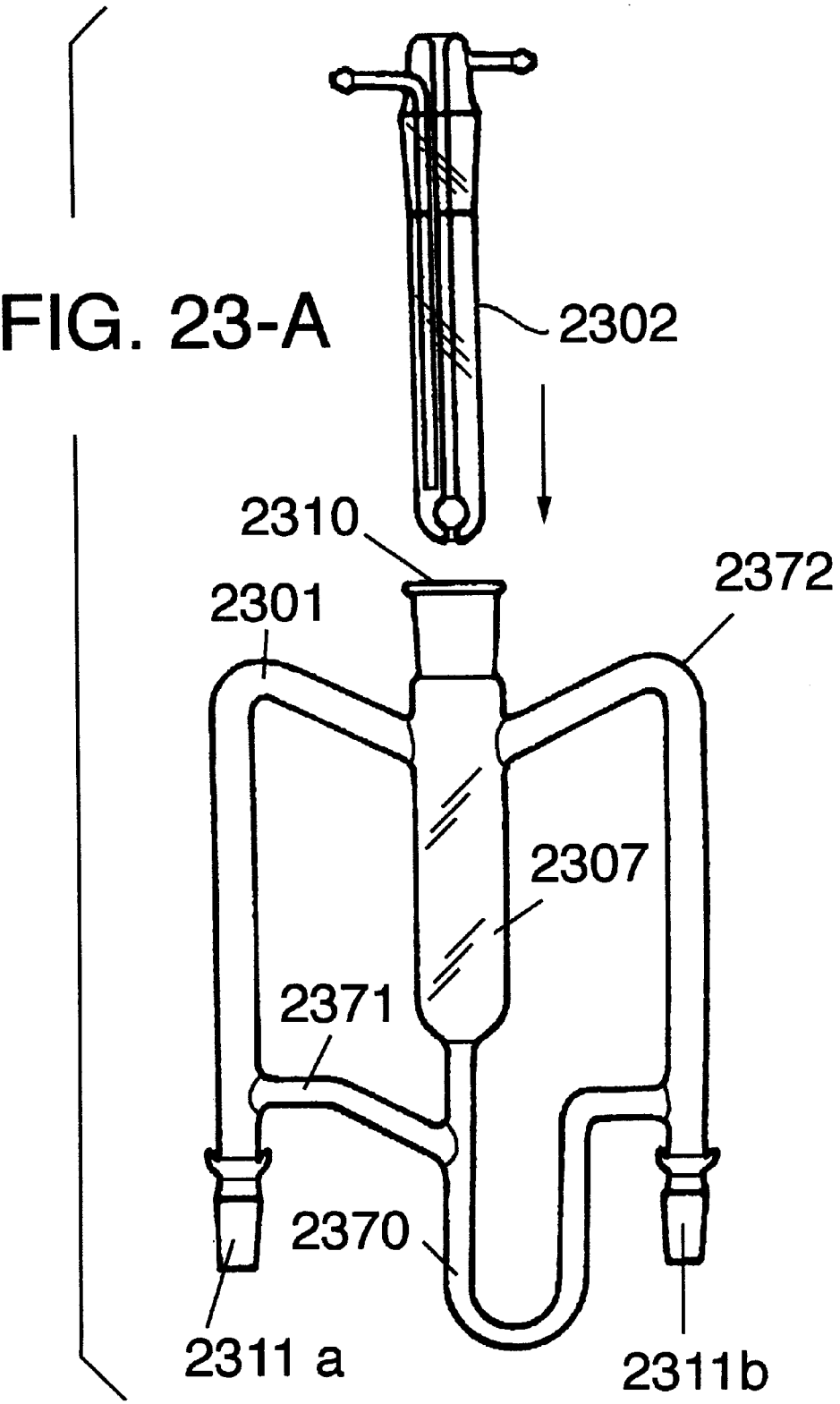
FIG. 23-A

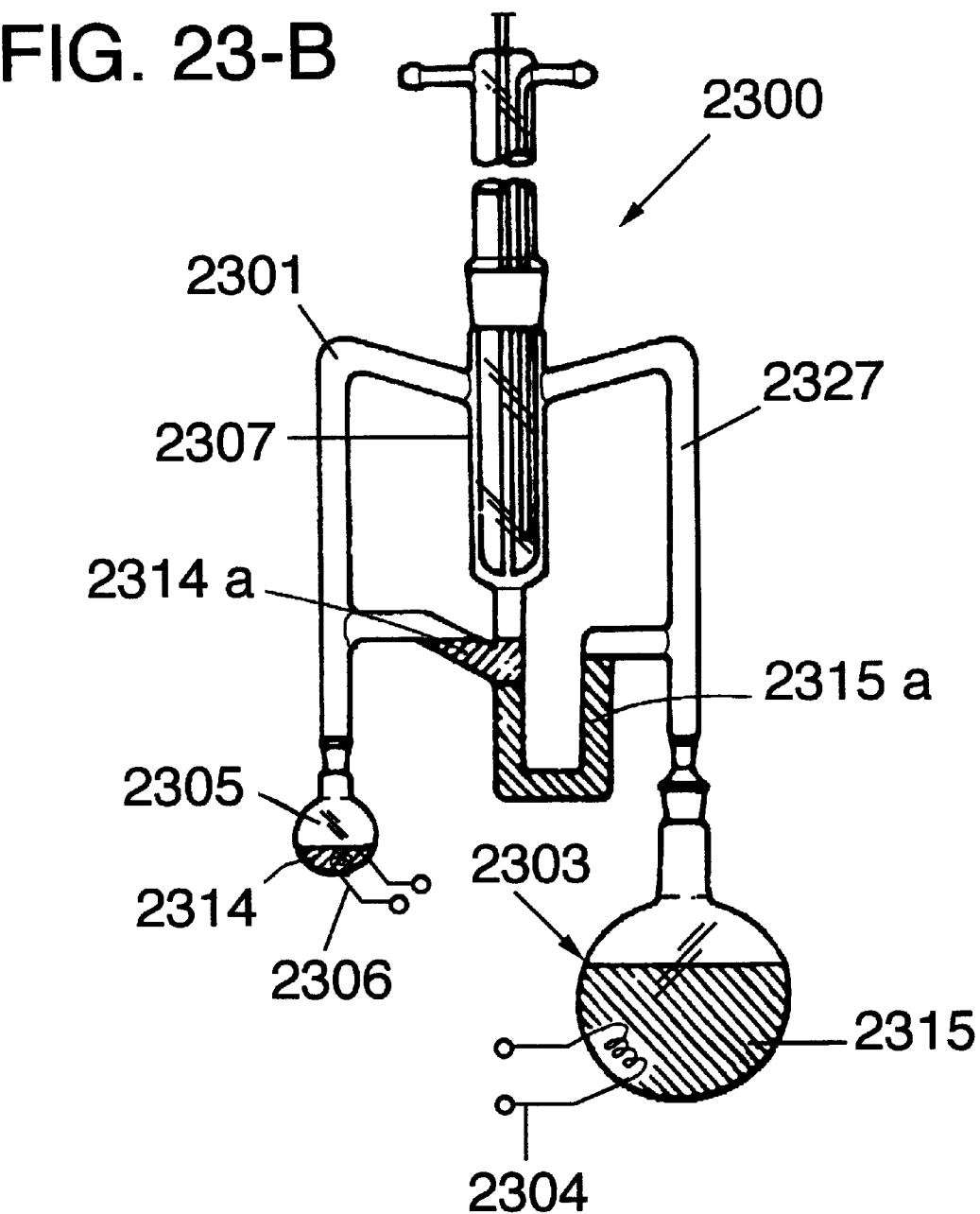
FIG. 23-B

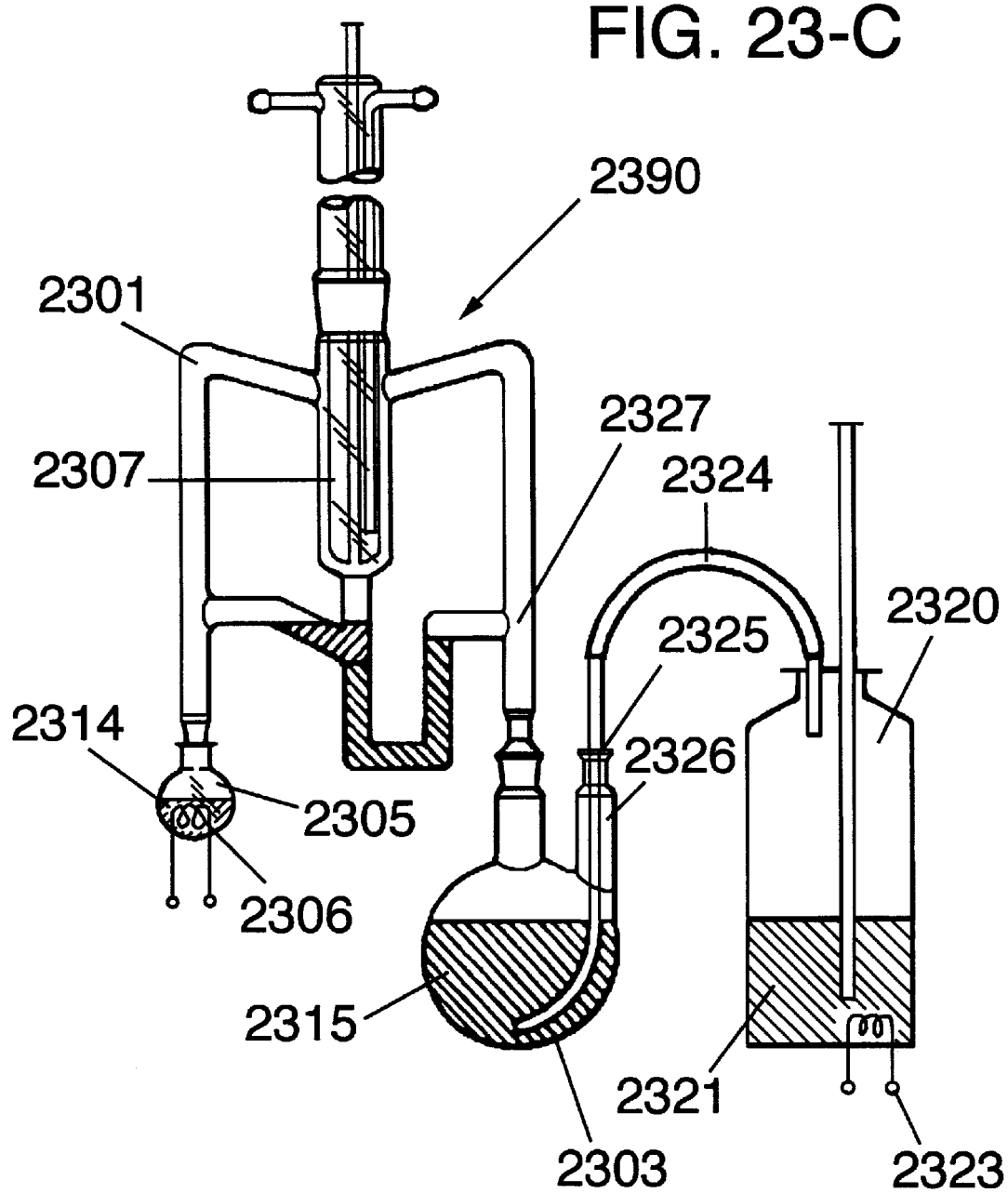

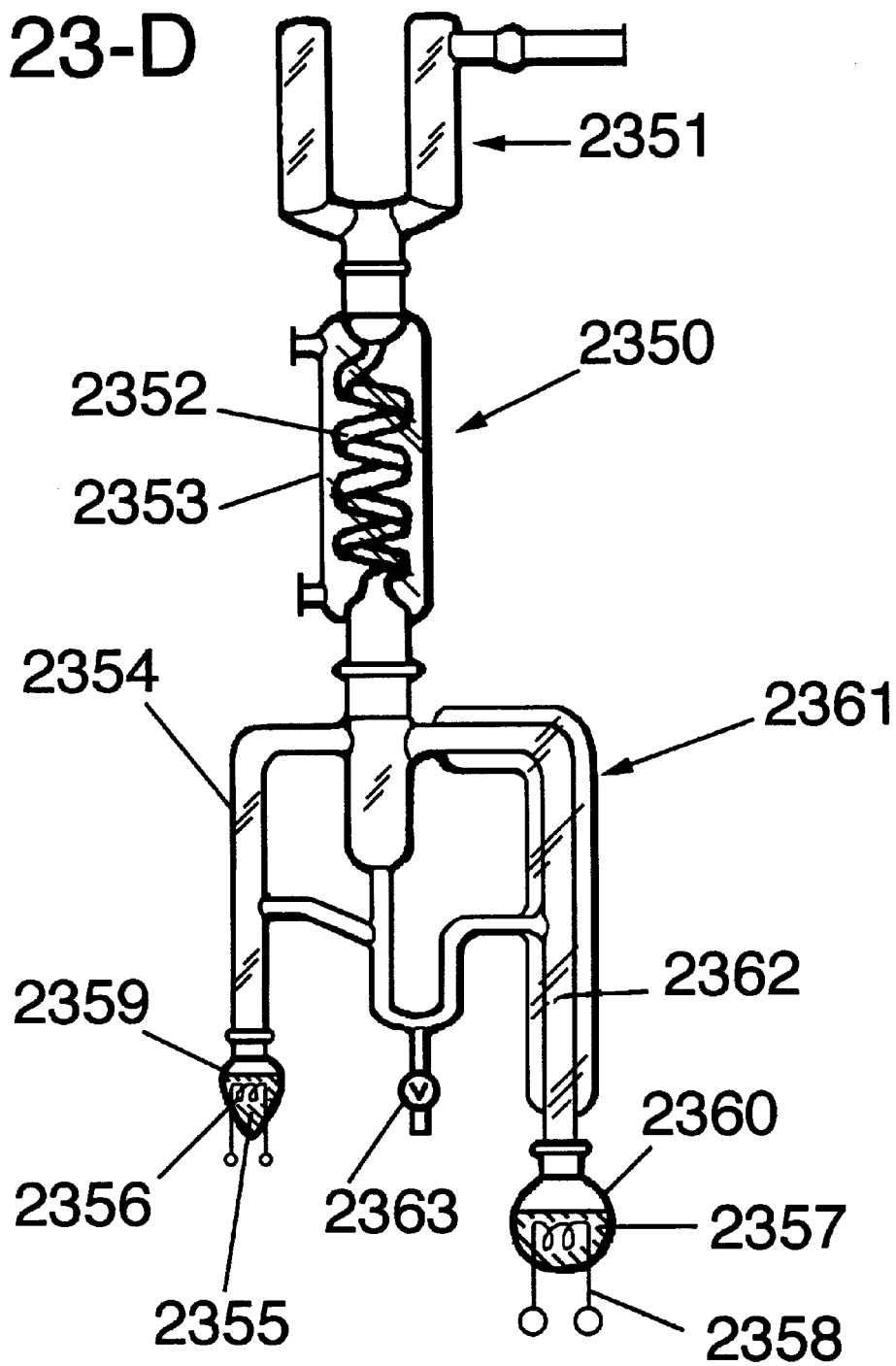
FIG. 23-D

PRODUCING TASTANDS INCLUDING FOOD AND BEVERAGE ADDITIVES

This is a Divisional of application Ser. No. 09/038,945 filed Mar. 12, 1998 pending.

BACKGROUND OF THE INVENTION

Our invention relates to a process for producing one or more tastands including one or more natural food additives comprising the sequential steps of:

(i) providing a plurality of *Saccharum officinarum* leaves (sugarcane leaves), macerates thereof or a mixture of *Saccharum officinarum* leaves and macerates thereof; and (ii) carrying out one or more physical separation unit operations on said plurality of *Saccharum officinarum* leaves, macerates thereof or mixture of leaves and macerates thereof;

whereby a natural tastand or food additive is separated and isolated from the remainder of said plurality of *Saccharum officinarum* leaves, macerates thereof or mixtures of leaves and macerates thereof. The physical separation unit operations include but are not limited to steam distillation; high pressure extraction, for example, using one or more screw presses; pervaporation; extraction using an extraction column such as a charcoal extraction column; standard fractional distillation, batch or continuous; high pressure, volatile solvent extraction; and super critical carbon dioxide extraction.

Foodstuffs, chewing gums and beverages, which are sweetened with sweeteners other than natural sugars or which contain sodium chloride replacers, for example foodstuffs, chewing gums and beverages which contain potassium chloride and/or L-aspartyl-L-phenylalanine ethyl ester have been made the subject of intensive research efforts whereby the bitter or metallic taste of the eatable is covered or "improved." Thus, for example, U.S. Pat. No. 5,639,788 assigned to Bioresearch, Incorporated discloses a composition comprising (a) an eatable having a bitter and/or metallic taste and (b) at least one tastand selected from L-aspartyl-L-phenylalanine, L-aspartyl-L-tyrosine and their salts in a substantially tasteless amount of 0.0000001–300 weight percent based on the weight of the eatable. U.S. Pat. No. 5,639,788 indicates that the eatable is bitter tasting potassium chloride, an amino acid, a peptide, a polypeptide, or a protein or N-1-α-aspartyl-1-phenylalanine ethyl ester. It is further indicated in U.S. Pat. No. 5,639,788 that the eatable is any ingested material taken by humans, animals and the like and may be a foodstuff, non-calorie food component (e.g., flavoring or medicine including bitter chocolate or a drug such as ibuprofen). The tastand is indicated in U.S. Pat. No. 5,639,788 to be incorporated in or ingested with an eatable and can prevent bitter components from interacting with the mammalian taste receptor. Use of the tastand is indicated in U.S. Pat. No. 5,639,788 to allow reformulation for low-calorie or low-sodium foods.

From a reading of such documents as U.S. Pat. No. 5,639,788, it has become apparent that there exists a need to provide improvement of bitter or metallic taste of such eatables containing such materials as potassium chloride and L-aspartyl-L-phenylalanine ethyl ester using natural substances.

Nothing in the prior art and nothing known in commerce has implicitly or explicitly yielded the information that *Saccharum officinarum* leaves, macerated and/or non-macerated are a source of such improvement.

The prior art techniques for processing sugarcane (*Saccharum officinarum*) and analyzing sugarcane products include the processing of *Saccharum officinarum* leaves along with the sugarcane where the *Saccharum officinarum* leaves are intended to be primarily discarded.

Thus, in *Proceedings of the 1978 Technical Session on Cane Sugar Refining Research*, Sep. 17–19, 1978, Washington, D.C., published by the Science and Education Administration, U.S. Department of Agriculture, Godshall, et al published a paper entitled "THE IDENTIFICATION OF VOLATILE CONSTITUENTS IN SUGARCANE AND CANE SUGAR PRODUCTS" at pages 46–67. Godshall, et al identified the volatiles eluted from *Saccharum officinarum* leaves, including 3-hexen-1-ol and dimethyl sulfide and also hypothesized several pathways by which the dimethyl sulfide formation can occur. In Table 1 on page 48 of Godshall, et al, a partial list of constituents previously identified in molasses that contribute to aroma and flavor is set forth. Table 2 of the Godshall, et al paper (set forth at page 53) shows the volatile constituents identified in molasses. Table 3 on page 56 of Godshall, et al sets forth the volatile constituents identified in cane leaves, to wit: acetaldehyde, ethanol, acetonitrile, 2-propanol, acetone, dimethyl sulfide, 3-hexen-1-ol, 2,4-hexadienal, 1-hexen-3-ol and 2,4-heptadienal. A GLC profile is set forth for volatiles eluted from *Saccharum officinarum* leaves on page 58 of Godshall, et al.

Similarly, in Chapter 2 of the text *Cane Sugar Handbook, a manual for cane sugar manufacturers and their chemists*, Tenth Edition, published by John Wiley & Sons, Meade and Chen, 1977, it is indicated in Section 2.1 at page 15 (Chapter 2, Irvine, "Composition of Cane and Juice"):

"2.1 Trash and Cane. When cane is cut and cleaned by hand, and delivered fresh, processors receive the best possible starting material for sugar production. Cane that is cut and loaded by machine invariably contains tops, leaves, stubble and roots, as well as soil, water, and other extraneous matter.

Deduction for trash in the delivered cane is a worldwide practice, but methods of trash determination vary widely. To judge the effect of trash, one should consider each fraction of the cane plant and its contribution of sucrose and of undesirable components. Juice from tops—including the stem tip, or soft, elongating joints as well leaf blades, sheaths, and rolls—contains less than 1% sucrose and is relatively rich in starch, soluble polysaccharides, and reducing sugars (Table 2.2). When tops (and dead leaves) are milled, these undesirable constituents are extracted and adversely affect sucrose recovery. Milled cane trash mixes with the crushed stalks, sponges up the richer stalk juices, and leaves the mill train with 3% sucrose . . . ."

At page 77 of Chapter 2 of the above-identified publication, at FIG. 5.26, there is shown a diagram of a French screw press (manufactured by the French Oil Mill Machinery Company) for use in processing cush-cush fiber. It is indicated on page 77 of the Meade and Chen Publication:

"The French screw press has also been used for one more extraction of bagasse from the last mill in several mills in Florida and Louisiana. The report from Osceola mill shows the arrangement in FIG. 5.28, and the analysis (Table 5.10) of juice and bagasse for two grinding seasons."

In *FAO AGRICULTURAL SERVICES BULLETIN*, No. 39, "small-scale cane sugar processing and residue utilization" by Issay Isaias, published by the Food and Agricultural Organization of the United Nations, Rome 1980, at page 35, it is indicated that cane tops and leaves are byproducts of the cane sugar industry and the general use is for animal feed. At paragraph 2 on page 36 of the FAO Publication No. 39, it is indicated:

"3.2.1 Cane Tops . . . The feeding system to be applied in the use of cane tops and leaves is important and deserves practical consideration with respect to feed intake and digestibility. Depending on the availability of other crop residues and molasses as liquid supplement, cane tops and leaves could be incorporated into a complete cattle feed in various ways and proportions . . . ."

The use of the screw press in extracting liquids from materials such as cotton seeds, copra, linen seeds, bagasse and the like, wherein the screw acts as a conveyor through a press cage, is set forth in detail in the following documents:

U.S. Pat. No. 3,561,351 issued on Feb. 9, 1971;
U.S. Pat. No. 3,662,679 issued on May 16, 1972;
U.S. Pat. No. 3,661,082 issued on May 9, 1972;
U.S. Pat. No. 643,891 issued on Feb. 20, 1900, each of which patent is incorporated by reference herein.

However, nothing in the prior art discloses a process for producing tastands, including natural food additives comprising the sequential steps of:

(i) providing a plurality of *Saccharum officinarum* leaves (sugarcane leaves), macerates thereof or a mixture of *Saccharum officinarum* leaves and macerates thereof; and (ii) carrying out one or more physical separation unit operations on said plurality of *Saccharum officinarum* leaves, macerates thereof or mixture of leaves and macerates thereof;

whereby a natural food additive is separated and isolated from the remainder of said plurality of *Saccharum officinarum* leaves, macerates thereof or mixtures of leaves and macerates thereof. Furthermore, nothing in the prior art sets forth apparatus for carrying out such a process.

BRIEF DESCRIPTION OF THE INVENTION

Our invention is directed to a process for producing tastands, including a natural food additive comprising the sequential steps of:

(i) providing a plurality of *Saccharum officinarum* leaves (sugarcane leaves), macerates thereof or a mixture of *Saccharum officinarum* leaves and macerates thereof; and (ii) carrying out one or more physical separation unit operations on said plurality of *Saccharum officinarum* leaves, macerates thereof or mixture of leaves and macerates thereof;

whereby a tastand, including natural food additive is separated and isolated from the remainder of said plurality of *Saccharum officinarum* leaves, macerates thereof or mixtures of leaves and macerates thereof.

Our invention is also directed to compositions comprising (a) such tastands in admixture with (b) an eatable having a bitter and/or metallic taste where the eatable is any ingested material taken by mammals, such as foodstuffs, non-calorie food components or medicines including bitter chocolate or a drug such as ibuprofen.

The *Saccharum officinarum* leaves, useful in carrying out the process of our invention and in producing the compositions of our invention, may be immature or mature *Saccharum officinarum* leaves, that is *Saccharum officinarum* leaves taken from young *Saccharum officinarum* plants or *Saccharum officinarum* plants ready to be harvested. The *Saccharum officinarum* leaves which are used in the processes of our invention, whether mature or immature, may include or may not include that portion of the sugarcane above the terminal node including the meristem. The materials used in the processes of our invention are not intended to include any portion of the sugarcane below the terminal node thereof.

Reference is herein made to texts describing sugarcane parts, to wit:

*PRODUCTION OF SUGAR CANE*, 1972 by F. LeGrand; and *SUGARCANE CROP LOGGING AND CROP CONTROL: PRINCIPLES AND PRACTICES*, 1980 by Harry F. Clements.

Both of the above references are incorporated by reference herein.

More particularly, the process of our invention is such that the step of carrying out the physical separation unit operations on said plurality of *Saccharum officinarum* leaves, macerates thereof or mixtures of leaves and macerates thereof comprises the sequential substeps of:

(a) effecting pressurization of said leaves, macerates thereof or mixture of leaves and macerates thereof using a hydraulic press such as a screw press, thereby separating liquid leaf extract from pressed cake; and (b) separating said tastand including natural food additive from said extract by means of a second unit operation such as fractional distillation and/or high-pressure solvent extraction (using, for example, 1,1,1,2-tetrafluoroethane) and/or supercritical carbon dioxide extraction and/or pervaporation.

In the alternative, the step of carrying out the physical separation unit operation on said plurality of *Saccharum officinarum* leaves, macerates thereof or mixtures of leaves and macerates thereof may comprise the unit operation of steam distillation of the *Saccharum officinarum* leaves, macerates thereof or mixtures of leaves and macerates thereof. The resulting steam distillate is condensed as an aqueous solution and the resulting aqueous solution is then subjected to a second unit operation such as high-pressure solvent extraction (using, for example, 1,1,1,2-tetrafluoroethane) and/or supercritical carbon dioxide extraction and/or pervaporation.

The resultant materials may then be subjected to further refinement using activated charcoal adsorption/elution techniques. Thus, activated charcoal can be used to adsorb the distillate of the *Saccharum officinarum* leaf. The adsorbed charcoal is then packed into a glass column and steamed distilled to yield specific materials, such as damascenone having the structure:

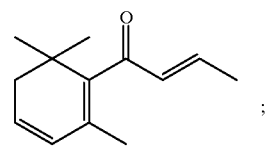

β-homocyclocitral having the structure:

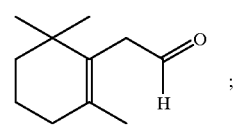

2,2,6-trimethyl cyclohexanone having the structure:

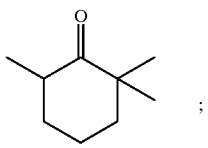

1-octen-3-ol having the structure:

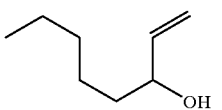

cis-3-hexenol having the structure:

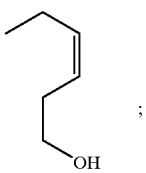

acetophenone having the structure:

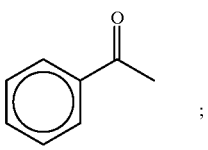

β-damascone having the structure:

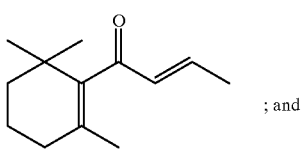

; and 3-methyl-2-buten-1-ol having the structure:

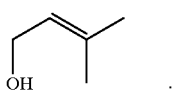

In addition, d-borneol having the structure:

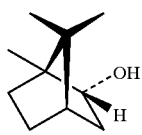

is recovered in this manner.

The distillate of the press extract as well as the steam distillate may, if desired, be subjected to a pervaporation unit operation. Furthermore, other liquid phase unit operation products resulting from the process of our invention may be subjected to the pervaporation unit operation.

In the pervaporation step, the press extract and/or distillate is passed over a pervaporation membrane capable of (i) permitting concentrated essence in the gaseous phase to pass therethrough and (ii) preventing the passage therethrough of juice or dilute essence components other than the concentrated essence containing desirable, natural food additive products. The conditions of the pervaporation are as follows:

(a) an inlet pressure in the range of from about 0.5 up to about 30 psig;

(b) an outlet pressure in the range of from about zero up to about 400 mm/Hg;

(c) a pressure drop across the membrane in the range of from 11,100 up to about 34,000 mm/Hg;

(d) an inlet pressure in the range of from about 40° C. up to about 90° C.;

(e) an outlet pressure in the range of from about −320° C. up to about +20° C.;

(f) a temperature change across the membrane in the range of from about 20° C. up to about 410° C.; and (g) a mass throughput in the range of from about 2 up to about 20 gallons/hour-foot².

The concentrated essence in the gaseous phase is condensed whereby a liquid phase is formed. The condensation step has two consecutive substeps:

(α) first partially condensing the gaseous phase and removing water, whereby the gaseous phase is converted to a liquid water phase; and then (β) condensing the essence portion of the gaseous phase, whereby a condensed essence in the liquid phase is formed.

The pervaporation step is controlled by the algorithm:

$$Q = K_1 \left[ \frac{(P_i)}{(T_i)} \right]^{\alpha} \left[ \left[ \frac{\partial(\Delta P)}{\partial(\Delta T)} \right]_{P_i,T_i} + K_2 \right]$$

wherein $K_1$ is a constant in the range of 0.01 up to 0.03 and is a function of the flavor essence; $K_2$ is a constant in the range of −700 to −100 and is a function of the flavor essence; α is a constant in the range of 0.01 up to 0.05 and is a function of the flavor essence; $P_i$ is the inlet pressure; $T_i$ is the inlet temperature; and $$\left[ \frac{\partial(\Delta P)}{\partial(\Delta T)} \right]_{P_i,T_i}$$

is the first derivative of pressure drop with respect to temperature change across the pervaporation membrane and pressure is in units of psig and temperature is in units of degrees Kelvin.

More specifically, preferred pervaporation apparatus has an inlet temperature of 150° F. and an effluent temperature of 20° F. with the exit pressure being at 40 mm/Hg pressure.

The fractional distillation described above takes place using a column having from about 6 plates up to about 15 plates with a reflux ratio of between 1:1 and 7:1 with a preferred reflux ratio of 4:1. The distillation is carried out at from about 70° C. up to about 225° C. and at pressures in the range of from about 0.7 up to about 3 atmospheres absolute, preferably at atmospheric pressure at 100° C., whether (i) the distillate is steam distillate from the *Saccharum officinarum* leaves themselves or (ii) the distillate is the overhead distillation product of the press extract.

More specifically, the process of our invention comprises the sequential steps of:

(i) harvesting a plurality of *Saccharum officinarum* stalks which a bear a plurality of *Saccharum officinarum* leaves;

(ii) removing a plurality of *Saccharum officinarum* leaves from said stalks which may or may not include that part of the stalk above the terminal node, which stalks bear a plurality of *Saccharum officinarum* leaves;

(iii) removing a plurality of *Saccharum officinarum* leaves from said stalks thereby providing to a plurality of leaves, and this may include that part of the stalk above the terminal node;

(iv) macerating at least a finite portion of said leaves (including or not including that part of the stalk above the terminal node) to produce a leaf composition comprising macerated *Saccharum officinarum* leaves;

(v) either (α) placing said leaf composition in intimate contact with an aqueous vapor over a prolonged period of time in order to form an aqueous vapor-tastand or food additive composition in the vapor phase; or (β) applying pressure to said leaf composition in order to form an aqueous tastand or food additive composition;

(vi) in the case of forming the aqueous vapor-tastand or food additive composition in the vapor phase, condensing the vapor phase aqueous vapor-tastand or food additive composition whereby a liquid phase aqueous tastand or food additive composition is formed; and (vii) carrying out physical separation unit operations on said liquid phase aqueous tastand or food additive compositions whereby said natural tastand or food additive compositions are formed.

As stated, supra, the physical separation unit operations include but are not limited to fractional distillation, pervaporation, super critical carbon dioxide extraction, solvent extraction as by using a volatile solvent such as diethyl ether or 1,1,1,2-tetrafluoroethane and the like.

When (as in step (v), supra) applying pressure to the *Saccharum officinarum* leaves, it is preferred to utilize a screw press, such as that described in U.S. Pat. No. 3,662,679 issued on May 16, 1972 or such as that described in U.S. Pat. No. 3,561,351 issued on Feb. 9, 1971, the specifications for which are incorporated by reference herein. A single pressure device may be used or multiple pressure devices may be used. Thus, for example, two screw presses may be used in series whereby the macerate from the first screw press is admixed with water and then fed into a second screw press. Thus, the pressing stages may be one or several stages and may involve the use of one screw press, several screw presses or screw presses and other hydraulic pressing devices. In addition, a multi-screw press as described in U.S. Pat. No. 5,526,740 issued on Jun. 18, 1996 (incorporated by reference herein) may also be used in practicing our invention.

Screw presses of the type utilizable in our invention are set forth in British Patent Specification No. 1,244,047 published on Aug. 25, 1971. With respect to the use of the *Saccharum officinarum* leaf pressing device, outside air pressure of between about 50 up to about 100 psig may be used at a rate of 5–10 tons of *Saccharum officinarum* leaves per hour, yielding from about 250 up to about 300 gallons/hour of aqueous fluid. The internal pressure in the leaf pressing device varies from about 2,000 up to about 5,000 psig.

Overall, 50 tons of distillate will be produced by between 1,200 and 2,000 tons of *Saccharum officinarum* leaves, depending upon whether the leaves are mature or immature; that is depending on the stage at which the leaves are harvested from *Saccharum officinarum* canes.

With respect to the use of the screw press, the fluid yield is a function of:

(a) the physical properties of the fluid in the *Saccharum officinarum* leaves fed into the press, e.g., viscosity, density and temperature;

(b) the internal press pressure;

(c) the residence time of the *Saccharum officinarum* leaves in the press;

(d) the kinematic viscosity of the fluid within the press at press temperature;

(e) the degree of maturity of the *Saccharum officinarum* leaves fed into the press; and (f) the feed rate of the *Saccharum officinarum* leaves into the press and is shown by the following algorithm:

$$W^2 = \frac{CW_0^2 P^x \theta^y}{\gamma^z},$$

for example, the algorithm:

$$W^2 = \frac{CW_0^2 P^{1/2} \theta^{1/6}}{\gamma^{3/2}}$$

where the range of internal press pressure is from about 2,000 up to about 5,000 psig at a temperature of 18° C.; where θ is the residence time within the press in hours; $W_0$ is the initial *Saccharum officinarum* leaf oil content (including water) in the leaves prior to pressurization; wherein W is the expressed leaf oil yield (including water); wherein C is a constant for the *Saccharum officinarum* leaf depending upon maturity thereof and varying from about 0.003 up to about 0.01; and wherein γ is the kinematic viscosity (in units of stokes) of the fluid evolving from the press at press temperature.

In the generic algorithm:

$$W^2 = \frac{CW_0^2 P^x \theta^y}{\gamma^z}, x, y$$

and z are exponents which vary depending again on the leaf maturity. "x" May vary from 0.5 up to 1.3; y may vary from 0.2 up to 0.5; and z may vary from 0.1 up to 0.6. The rate of pressing of *Saccharum officinarum* leaf oil is calculated from the differential equation:

$$\frac{dW}{d\theta} = \frac{yCW_0^2 P^x \theta^{y-1}}{2W\gamma^z} + \frac{xCW_0^2 \theta^y P^{x-1}}{2W\gamma^z}\left(\frac{dP}{d\theta}\right)$$

wherein the term $$\frac{dW}{d\theta}$$

represents the rate of pressing of the leaf oil over a period of time and wherein the term $$\left(\frac{dP}{d\theta}\right)$$

represents the rate of the change of the internal press pressure with respect to time.

Work concerning the expression of oils has been carried out by Koo, in the article "Expression of Vegetable Oils/A General Equation on Oil Expression," *Industrial and Engineering Chemistry*, March 1942 at page 342–345, said reference being incorporated by reference herein.

The apparatus useful for carrying out the process of our invention for production of natural tastands including food additives comprises:

(i) harvesting means for harvesting a plurality of sugarcane stalks which bear a plurality of cane stalk leaves;

(ii) first conveying means for conveying said plurality of sugarcane stalks to leaf removal means;

(iii) leaf removal means proximate said first conveying means for removing a plurality of leaves from said sugarcane stalks in order to provide a plurality of cane stalk leaves;

(iv) second conveying means for conveying said cane stalk leaves to macerating means;

(v) macerating means for macerating at least a finite portion of said cane stalk leaves in order to produce a composition comprising macerated cane stalk leaves;

(vi) third conveying means for conveying said macerated cane stalk leaves to extraction means;

(vii) extraction means for causing the cane stalk leaves, including macerated cane stalk leaves, to be in intimate contact with an aqueous vapor (such as steam) over a prolonged period of time in order to form an aqueous vapor-tastand or food additive composition in the vapor phase;

(viii) vapor condensing means for condensing said vapor phase aqueous vapor-tastand or food additive composition whereby a liquid phase aqueous food additive composition is formed (for example, steam distillate condensate); and (ix) physical separation means for carrying out a physical separation unit operation on said liquid phase aqueous tastand or food additive composition whereby said natural tastand or food additive composition is isolated.

The physical separation means (ix) may be, for example, supercritical carbon dioxide extraction means or solvent extraction means such as high-pressure solvent extraction means using, for example, the solvent 1,1,1,2-tetrafluoroethane at pressures of 50 atmospheres or greater. In addition, further purification of the tastand or food additive may be used such as adsorption of the tastand or natural food additive composition on a material which may be, in the alternative:

(a) activated charcoal;

(b) resin; or (c) zeolites.

The physical separation means (ix) may also include pervaporation apparatus described in detail, infra.

In the alternative, the apparatus of our invention for producing natural tastands including food additives comprises:

(i) harvesting means for harvesting a plurality of sugarcane stalks which bear a plurality of cane stalk leaves;

(ii) leaf stripping means for removing a plurality of leaves from said harvested sugarcane stalks immediately after harvesting whereby a plurality of cane stalk leaves is provided;

(iii) first conveying means for conveying said plurality of cane stalk leaves to macerating means;

(iv) proximate said first conveying means, macerating means for macerating at least a finite portion of said cane stalk leaves to produce a composition comprising macerated cane stalk leaves (v) second conveying means for conveying cane stalk leaves and macerated cane stalk leaves to hydraulic pressurization means;

(vi) proximate said second conveying means, hydraulic pressurization means for applying from about 2,000 up to about 5,000 psig pressure to said cane stalk leaves including macerated cane stalk leaves over a period of time in order to separate an aqueous tastand or food additive composition from the cane suger leaves including macerated cane sugar leaves;

(vii) physical separation means for carrying out a physical separation unit operation on said tastand or food additive composition whereby said natural tastand or food additive composition is formed.

The physical separation means for carrying out the physical separation unit operation on said tastand or food additive composition whereby said natural tastand or food additive composition is formed may be fractional distillation means whereby the tastand or food additive composition is condensed from the overhead distillation product. In the alternative, or in addition, the physical separation means may comprise supercritical carbon dioxide extraction means and/or may comprise solvent extraction means such as diethyl ether extraction means or high-pressure solvent extraction means such as that using 1,1,1,2-tetrafluoroethane at pressures of 50 atmospheres and greater. In addition, an additional physical separation means may also be used such as means for adsorption of said tastand or natural food additive composition on a material selected from the group consisting of:

(a) activated charcoal;

(b) resin; or (c) zeolites.

In addition, the physical separation means of (vii) of the aforesaid process may also include pervaporation apparatus means as more specifically described in detail, infra.

The tastand and food additive compositions isolated as a result of carrying out the unit operations of the processes of our invention using the apparatus of our invention have been found to include a number of materials which in and of themselves, in combination with one another, remove bitter aftertaste and enhance sweetness of various beverages and foodstuffs including but not limited to beverages produced from cola-nut extract and yogurts, using sweeteners other than natural sugars. These tastand additive or food additive components include but are not limited to:

damascenone having the structure:

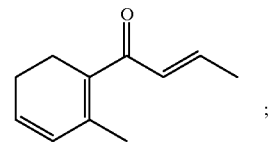

β-damascone having the structure:

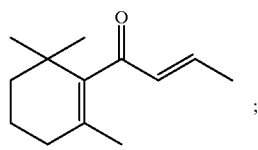

β-homocyclocitral having the structure:

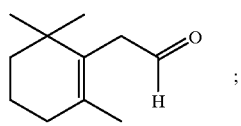

cis-3-hexenol having the structure:

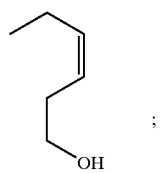

1-octen-3-ol having the structure:

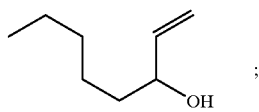

β-phenylethyl alcohol having the structure:

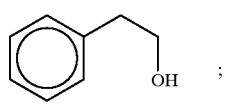

3-methyl-2-buten-1-ol having the structure:

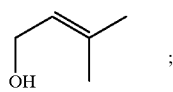

acetophenone having the structure:

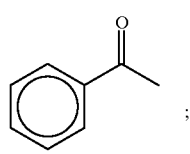

2,2,6-trimethyl cyclohexanone having the structure:

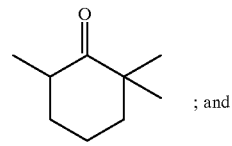

; and d-borneol having the structure:

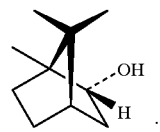

Our invention is directed to compositions containing at least two of the above components for use in removing bitter aftertaste and enhancing sweetness of beverages, particularly those which include aspartame and its homologs defined according to the structure:

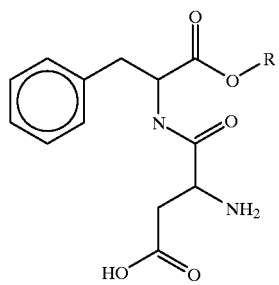

wherein R represents $C_1$–$C_4$ lower alkyl. Aspartame itself has the structure:

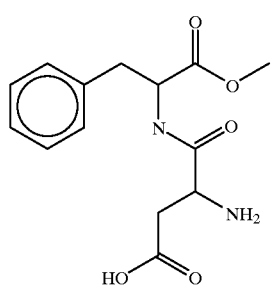

wherein R is methyl.

More specifically, our invention is directed to processes for removing bitter aftertaste and enhancing sweetness comprising the step of adding to an eatable having bitter nuances (such as an artificially sweetened beverage containing aspartame) from about 1 up to about 20 ppb (parts per billion) of damascenone having the structure:

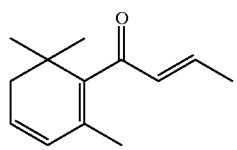

and an alcohol selected from the group consisting of:

cis-3-hexenol having the s structure:

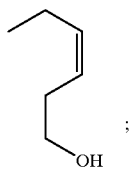

1-octen-3-ol having the structure:

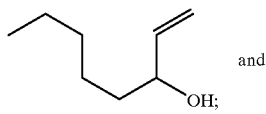
and

β-phenylethyl alcohol having the structure:

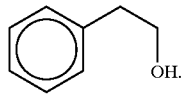

Our invention is also directed to a process for removing the bitter aftertaste and enhancing sweetness comprising the step of adding to an eatable having bitter nuances from about 1 up to about 20 ppb of β-homocyclocitral having the structure:

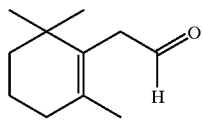

and an oxo compound selected from the group consisting of:

(a) cis-3-hexenol having the structure:

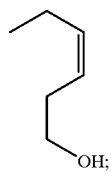

(b) acetophenone having the structure:

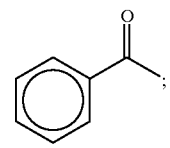

(c) massoia lactone having the structure:

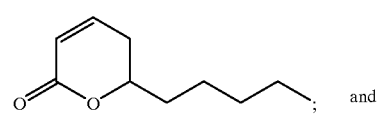
and (d) the "pineapple compound" having the structure:

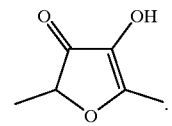

Although massoia lactone having the structure:

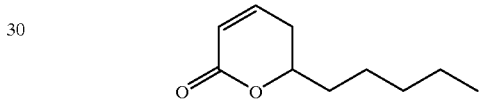

and the pineapple compound having the structure:

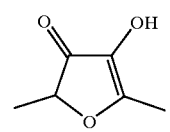

were not found in the extract of the sugarcane leaves produced according to the process of our invention, we have found that both massoia lactone and the pineapple compound in admixture with β-homocyclocitral as well as in admixture with cis-3-hexenol unexpectedly and unobviously removed bitter aftertaste and enhanced sweetness of an eatable having bitter nuances.

Thus, our invention is also directed to a process for removing bitter aftertaste and enhancing sweetness comprising the step of adding to an eatable having bitter nuances from about 1 up to about 20 ppb of cis-3-hexenol having the structure:

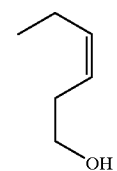

and an oxo compound selected from the group consisting of:
(a) massoia lactone having the structure:

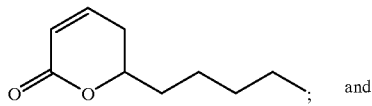
; and (b) the "pineapple compound" having the structure:

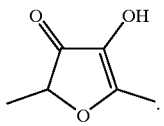
.

With respect to the mixtures of our invention containing damascenone and alcohol, the mole ratio of damascenone:alcohol may vary from about 1:10 up to about 10:1 damascenone:alcohol.

With respect to the compositions of our invention containing β-homocyclocitral and an oxo compound as defined, supra, the mole ratio of β-homocyclocitral:oxo compound may vary from about 1:10 up to about 10:1.

With respect to the compositions of our invention containing cis-3-hexenol and an oxo compound, the mole ratio of cis-3-hexenol:oxo compound as defined, supra, may vary from about 1:10 up to about 10:1.

Accordingly, it will be appreciated from the present disclosure that the compositions as set forth above according to the present invention can be used to alter, vary, fortify, modify, enhance or otherwise improve the flavor of a wide variety of consumable materials which are ingested, consumed or otherwise organoleptically sensed.

The terms "alter" and "modify" in their various forms will be understood herein to mean the supplying or imparting of a flavor character or note to an otherwise bland, relatively tasteless substance, or augmenting an existing flavor characteristic where the natural flavor is deficient in some regard or supplementing the existing flavor impression to modify their organoleptic character, such as removing bitter and metallic notes and bitter aftertaste as well as enhancing sweetness.

Thus, the term "enhance" is intended herein to mean the intensification (by use of the tastand compositions of our invention) of a flavor or aroma note or nuance in a foodstuff without changing the quality of said note or nuance.

A "flavoring composition" is taken to mean one which contributes a part of the overall flavor impression by supplementing or fortifying a natural or artificial flavor in a material or one which supplies substantially all the flavor and/or aroma character to a consumable article.

The term "foodstuff" as used herein includes both solid and liquid ingestible materials for man or animals, which materials usually do, but need not have nutritional value. Thus, foodstuffs include meats, gravies, soups, convenience foods, malt, alcoholic and other beverages, milk and dairy products, seafoods, including fish, crustaceans, mollusks and the like, candies, vegetables, cereals, soft drinks, snacks, dog and cat food, other veterinary products and the like. The tastand compositions of our invention are also useful tobacco flavorants and flavor enhancers.

When the tastand compositions of our invention, including the damascenone:alcohol compositions, the β-homocyclocitral:oxo compound compositions and the cis-3-hexenol:oxo compositions of our invention as well as the products prepared according to the processes of our composition prior to ultimate purification thereof as set forth, supra, are used in a flavoring composition, they can be combined with conventional flavoring materials or adjuvants. Such co-ingredients or flavoring adjuvants are well known in the art for such use and have been extensively described in the literature. Requirements of such adjuvant materials are:

(1) that they be non-reactive with the products produced according to the processes, supra, prior to final purification;

(2) that they be non-reactive with the damascenone:alcohol compositions defined, supra; or the β-homocyclocitral:oxo compound compositions defined, supra; or the cis-3-hexenol:oxo compound compositions defined, supra;

(3) that they be organoleptically compatible with the products produced according to the processes described, supra; as well as the damascenone:alcohol compositions defined, supra; and the β-homocyclocitral:oxo compound compositions defined, supra; as well as the cis-3-hexenol:oxo compound compositions defined, supra, whereby the flavor of the ultimate consumable material to which these tastands are added are not detrimentally affected by the use of the adjuvant; and (4) that they be ingestibly acceptable and thus non-toxic or otherwise deleterious.

Apart from these requirements, conventional materials can be used and broadly include other flavor materials, vehicles, istabilizers, thickeners, surface-active agents, conditioners and flavor intensifiers.

Such conventional flavoring materials include saturated fatty acids, unsaturated fatty acids and amino acids; other alcohols including primary and secondary alcohols, esters, other carbonyl compounds including ketones and aldehydes; lactones; other cyclic organic materials including benzene derivatives, alicyclic compounds, heterocyclics such as furans, pyridines, pyrazines and the like; sulfur-containing compounds including thiols, sulfides, disulfides and the like; proteins, lipids carbohydrates; so-called flavor potentiators such as monosodium glutamate, magnesium glutamate, calcium glutamate, guanylates and inosinates; natural flavoring materials such as cocoa, vanilla and caramel; essential oils and extracts such as anise oil, clove oil and the like; and artificial flavoring materials such as vanillin and the like.

Specific preferred flavor adjuvants are as follows:

anise oil;

ethyl-2-methyl butyrate;

vanillin;

butyl valerate;

2,3-diethyl pyrazine;

methyl cyclopentenolone;

benzaldehyde;

valerian oil;

3,4-dimethoxyphenol;

amyl acetate;

amyl cinnamate;

γ-butyryl lactone;

furfural trimethyl pyrazine;

phenyl acetic acid;

isovaleraldehyde;

maltol;

ethyl maltol;
ethyl vanillin;
ethyl valerate;
ethyl butyrate;
cocoa extract;
coffee extract;
peppermint oil;
spearmint oil;
clove oil;
anethol;
cardamom oil;
wintergreen oil;
cinnamic aldehyde;
ethyl-2-methyl valerate;
γ-hexenyl lactone;
2,4-decadienal;
2,4-heptadienal; and
butylidene phthalide.

BRIEF DESCRIPTION OF THE DRAWINGS

FIG. 1A is a perspective view of the *Saccharum officinarum* plant (sugarcane plant) bearing *Saccharum officinarum* leaves, useful in the practice of our invention.

FIG. 1B is a perspective view of the upper part of the *Saccharum officinarum* plant showing the *Saccharum officinarum* (sugarcane plant) leaves.

FIG. 1C is a schematic diagram of the *Saccharum officinarum* plant with leaves showing the places where the plant is cut above or below the terminal node 15 thereof for the purposes of practicing our invention.

FIG. 1D is a schematic cutaway perspective view of that section of the *Saccharum officinarum* plant shown schematically in FIG. 1C between lines 15 and 17 showing the terminal node 15.

FIG. 1E is a schematic diagram of the top view of a macerate of the *Saccharum officinarum* leaves of the *Saccharum officinarum* plant of FIGS. 1A, 1B and 1C.

FIG. 1F sets forth the center part of the *Saccharum officinarum* plant showing in detail a cutaway view of the terminal node area as well as the *Saccharum officinarum* leaves attached to the *Saccharum officinarum* stalk.

FIG. 1G is a cutaway perspective view of the terminal node section (the meristem) of the *Saccharum officinarum* plant (sugarcane).

FIG. 1H is a schematic side elevation diagram of a blossomed *Saccharum officinarum* stalk separated into its several parts showing the *Saccharum officinarum* leaves schematically and showing the *Saccharum officinarum* stalk schematically as well as the stalk blossoms.

FIG. 1I is a cutaway schematic side elevation view showing all the parts of the *Saccharum officinarum* stalk including a vegetative cane top, internodes, leaf sheaths and blades as well as the meristematic tip. Shown are corresponding sheaths, blades, nodes and internodes.

FIG. 1J is an enlargement of the inner portion of the *Saccharum officinarum* stem tip showing relationship of the leaf next to the meristematic tip and the meristematic tip itself.

FIG. 1K is the entire cross section (schematic) of the stem tip of the sugarcane stalk as shown schematically in FIG. 1I.

FIG. 1L is a perspective schematic cutaway diagram of a *Saccharum officinarum* meristem showing nodal plates and vegetative buds in various stages of development as well as vascula leading into the leaves.

FIG. 1M is another diagram of a *Saccharum officinarum* sugarcane top showing leaves and showing the dewlap and sheath.

FIG. 1N is a cutaway perspective view of the center part of the cane top of FIG. 1M with tissues cut away to show relationship of the meristem to the other parts.

FIG. 2A is the GC-capillary survey for the extraction product of Example I (Carbowax column).

FIG. 2B is a GC-capillary survey for the extraction product of Example I using an OV-1 column.

FIG. 3A is a GC-capillary survey for the extraction product of Example II using an OV-1 column.

FIG. 3B is a GC-capillary survey for the extraction product of Example II using a Carbowax column.

FIG. 4 is a GC-mass spectrum for the distillate of Example IV.

FIG. 5A is a GC-mass spectrum for the distillate of Example V using an OV-1 column.

FIG. 5B is a GC-mass spectrum for the permeate of Example V.

FIG. 6A is a GC-mass spectrum for the charcoal column adsorbate of Example VI using a Carbowax column.

FIG. 6B is a GC-mass spectrum for the charcoal column adsorbate of Example VI using an OV-1 column.

FIG. 7A is a schematic block flow diagram showing the apparatus used in Example III.

FIG. 7B is a schematic block flow diagram showing the apparatus used in Example VI.

FIG. 10A is a schematic block flow diagram of apparatus used in connection with carrying out Example VII.

FIG. 10B is a schematic block flow diagram of apparatus used in carrying out Example V.

FIG. 11A, 11B, 11C and 11D are a cutaway side elevation view in schematic form of a screw press used in Example II. It is also described in detail in U.S. Pat. No. 643,891 issued on Feb. 20, 1900, the specification for which is incorporated by reference herein.

FIG. 12A. is a fragmentary section of the discharge end portion of a screw press having a final discharge worm constructed and replacable in accordance with the disclosure of U.K. Patent Specification No. 1,375,497 published on Nov. 27, 1974.

FIG. 12B is a larger fragmentary section of the apparatus of FIG. 12A.

FIG. 12C is an enlarged elevational view of the final discharge worm shown in FIGS. 12A and 12B.

FIG. 12D is an axial view of the discharge worm shown in FIG. 12C.

FIG. 12E is a view of a clamping device of the apparatus shown in FIG. 12B.

FIG. 15A is a cutaway side elevation view of a Vincent Corporation CP-4 inch press useful in the practice of Examples II and IV of our invention, manufactured by the Vincent Corporation of Tampa, Fla.

FIG. 15B is a top view of the inlet flange of the apparatus of FIG. 15A.

FIG. 15C is an end view of the screw press of FIG. 15A.

FIG. 20A and FIG. 20B show schematically an assembled unit of a plurality of separation modules of pervaporation apparatus (as used in Example IV of our invention) manufactured by the Chemical Equipment Division of Carbone of America, a subsidiary of GFT-Ingenieurbuero für Industrieanlagenplanung of Germany. The apparatus of FIGS. 20A and 20B is disclosed in detail in U.S. Pat. No. 4,769,140 issued on Sep. 6, 1988 and incorporated by reference herein.

FIG. 23A is a cutaway side elevation schematic view of "exploded" apparatus for carrying out the analysis for Example VIII of our invention. The apparatus is "Likens-Nickerson" apparatus described in detail in *PROGRESS IN FLAVOUR RESEARCH*, edited by D. G. Land and H. E. Nursten and given at the proceedings of the second Weurman Flavour Research Symposium held at the University of East Anglia at Norwich, England on Apr. 2–6, 1978 and published by the Applied Science Publishers Ltd. of London, England.

FIG. 23B is a cutaway side elevation view of the Likens-Nickerson analytical apparatus used in carrying out the analysis for Example VIII of our invention, described, infra, and showing solvent and aqueous solution in respective containers in the apparatus.

FIG. 23C is a variation of the Likens-Nickerson apparatus used in carrying out the analysis for Example VIII, infra. The apparatus of FIG. 23C shows steam distillation equipment in use in conjunction with the Likens-Nickerson apparatus.

FIG. 23D is another variation of the Likens-Nickerson apparatus used for the purposes of analysis for carrying out Example VIII, described, infra.

DETAILED DESCRIPTION OF THE DRAWINGS

Figure 8:
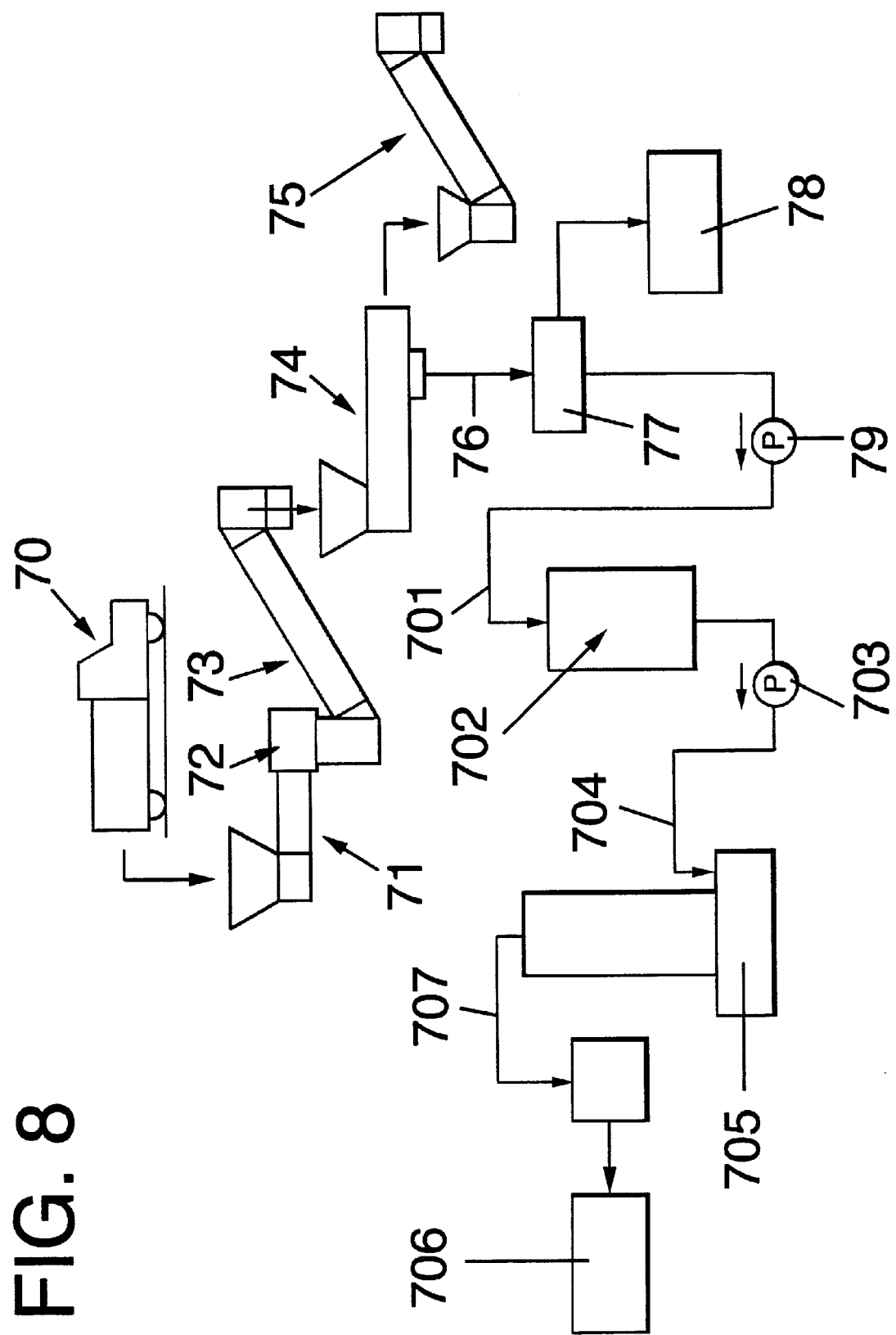
FIG. 8 is a schematic block flow diagram of apparatus used in Example VI.

Referring to FIGS. 1A, 1B, 1C and 1D, the *Saccharum officinarum* stalk (sugarcane stalk) is indicated by reference numeral 12; the *Saccharum officinarum* leaf is indicated by reference numeral 10; and the sugarcane top in the area of the meristem is indicated by reference numeral 11. The terminal node is indicated by reference numeral 15 and the cutting point above the terminal node is indicated by reference numeral 17, and the cutting point below the terminal node is indicated by reference numeral 16.

The macerated *Saccharum officinarum* leaves prior to steam distillation and/or hydraulic pressurization is indicated by reference numeral 18 in FIG. 1E.

FIGS. 1F, 1G, 1H, 1I, 1J and 1K are taken from *SUGARCANE CROP LOGGING AND CROP CONTROL: PRINCIPLES AND PRACTICES*, 1980, by Harry F. Clements, pages 52–55.

Referring to FIGS. 1F and 1G, reference numeral 106 refers to the *Saccharum officinarum* leaf. Reference numeral 103 shows the meristematic tip of the *Saccharum officinarum* cane stalk. FIG. 1F shows the *Saccharum officinarum* stalk with certain parts removed to reveal the relation of meristem 103 to the rest of the cane top.

In FIG. 1H, a blossomed stalk showing blossom 116 is schematically separated into its several parts, with sections of the stalk indicated by reference numeral 101 and various leaves relating to various sections of the stalk indicated by reference numeral 106.

Similarly, in FIG. 1I, reference numeral 106 shows the *Saccharum officinarum* leaf affiliated with a section of the stalk indicated by reference numeral 101. The meristematic tip is indicated by reference numeral 103.

The meristematic tip is shown in detail in FIG. 1L and is indicated by reference numeral 103.

FIGS. 1L, 1M and 1N were taken from *PRODUCTION OF SUGARCANE*, 1972, by F. LeGrand at pages 99 and 100. Thus, referring to FIGS. 1M and 1N, the top of the *Saccharum officinarum* cane is indicated by reference numeral 104, and the meristem tip is indicated by reference numeral 103. The sheath around the top of the *Saccharum officinarum* cane stalk 101 is where the *Saccharum officinarum* leaves begin to sprout from the stalk, the leaves being indicated by reference numeral 106a, 106b, 106c, 106d and 106e. The nodes for each section of the cane are indicated by reference numeral 102 in FIG. 1M, and the base of the cane stalk is indicated by reference numeral 101. The region of the meristem tip is indicated by reference numeral 107.

Referring to FIG. 2A, the peak indicated by reference numeral 21 is the peak for cis-3-hexenol having the structure:

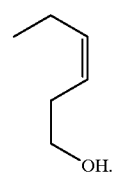

The peak indicated by reference numeral 22 is the peak for 1-octen-3-ol having the structure:

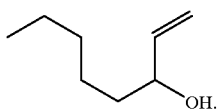

The peak indicated by reference numeral 23 is the peak for β-homocyclocitral having the structure:

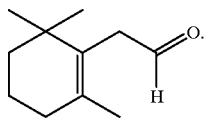

The peak indicated by reference numeral 24 is the peak for acetophenone having the structure:

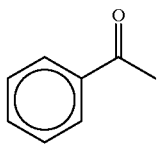

The peak indicated by reference numeral 25 is the peak for damascenone having the structure:

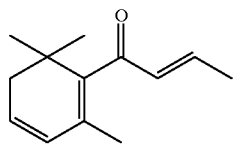

The peak indicated by reference numeral 26 is the peak for β-phenylethyl alcohol having the structure:

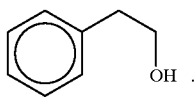

Referring to FIG. 3A, the peak indicated by reference numeral 31 is the peak for 1-octen-3-ol. The peak indicated by reference numeral 32 is the peak for 2,2,6-trimethyl cyclohexanone having the structure:

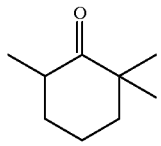

The peak indicated by reference numeral 33 is the peak for β-phenylethyl alcohol. The peak indicated by reference numeral 34 is the peak for damascenone. The peak indicated by reference numeral 35 is for β-damascone having the structure:

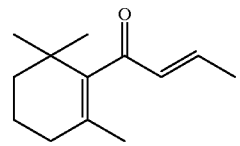

Referring to FIG. 3B, the peak indicated by reference numeral 36 is for cis-3-hexenol. The peak indicated by reference numeral 37 is for 1-octen-3-ol. The peak indicated by reference numeral 38 is for 2,2,6-trimethyl cyclohexanone. The peak indicated by reference numeral 39 is for damascenone. The peak indicated by reference numeral 301 is for β-phenylethyl alcohol.

Referring to FIG. 4, the peak indicated by reference numeral 40 is for 3-methyl-2-buten-1-ol having the structure:

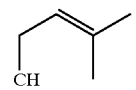

The peak indicated by reference numeral 41 is for cis-3-hexenol. The peak indicated by reference numeral 42 is for 1-octen-3-ol. The peak indicated by reference numeral 43 is for 2,2,6-trimethyl cyclohexanone. The peak indicated by reference numeral 44 is for β-homocyclocitral. The peak indicated by reference numeral 45 is for damascenone.

Referring to FIG. 5A, the peak indicated by reference numeral 50 is for 3-methyl-2-buten-1-ol. The peak indicated by reference numeral 51 is for cis-3-hexenol. The peak indicated by reference numeral 52 is for 1-octen-3-ol. The peak indicated by reference numeral 53 is for 2,2,6-trimethyl cyclohexanone. The peak indicated by reference numeral 54 is for d-borneol having the structure:

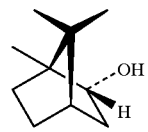

The peak indicated by reference numeral 55 is for damascenone. The peak indicated by reference numeral 56 is for β-damascone.

Referring to FIG. 5B, the peak indicated by reference numeral 57 is for 3-methyl-2-buten-1-ol. The peak indicated by reference numeral 58 is for cis-3-hexenol. The peak indicated by reference numeral 59 is for 1-octen-3-ol. The peak indicated by reference numeral 501 is for β-phenylethyl alcohol. The peak indicated by reference numeral 502 is for damascenone.

Referring to FIG. 6A, the peak indicated by reference numeral 60 is for cis-3-hexenol. The peak indicated by reference numeral 61 is for 1-octen-3-ol. The peak indicated by reference numeral 62 is for damascenone.

Referring to FIG. 6B, the peak indicated by reference numeral 63 is for cis-3-hexenol. The peak indicated by reference numeral 64 is for 1-octen-3-ol. The peak indicated by reference numeral 65 is for damascenone.

Referring to FIG. 7A showing a block flow diagram for the process of Example III, sugarcane tops at location 163 are conveyed into a screw press indicated by reference numeral 160. On operation of the screw press, press extraction liquid passes through line 167 past valve 168 into container equipped with stirrer 169. Pressed sugarcane tops are conveyed through conveying means 161 into the second screw press 162, which on operation, yields extract II which is passed past valve 166 through line 165 into container 169. Extracts I and II are then passed through heat exchanger 601 and then through line 602 past valve 603 into flash distillation, jacketed tank 604. Overhead distillate is condensed in condenser 605 and the condensate is passed through line 606 through chiller (heat exchanger) 607. The thus-chilled distillate is then passed through line 608 into containers 612, 613 and 614 with sections of the distillate sent into container 612, 613 and 614 being controlled using valves 609 and 610. Thus, distillate passing through lines 608 and 611 into container 614 contains 0.97 grams of cis-3-hexenol in 40 lbs of distillate. Distillate passed into container 613 contains 0.327 grams of cis-3-hexenol in 40 lbs of distillate. Distillate passed into container 612 contains 0.1 grams of cis-3-hexenol. Reference numerals 615, 616 and 617 indicate the purification locations for obtaining substantially pure cis-3-hexenol from the distillate liquids by means of high-pressure column chromatography.

Referring to FIG. 7B, the block flow diagram for the process of Example VI, *Saccharum officinarum* leaves are passed into screw press 618. Press extract I (liquid extract) is evolved from the screw press through line 619 past valve 620 through line 621 into holding tank 622. Screw press solid residue from screw press 618 is passed through line 624 into tank 625 equipped with stirrer where water from vessel 627 is added through line 650. The resulting slurry is then conveyed into screw press 626 which yields press cake through line 628 into vessel 629 and which yields additional press extract (liquid) which is passed through line 630 past valve 631 into holding tank 632. Extract II from screw press 626 is then passed through line 633 past valve 634 into distillation column 635. Simultaneously, extract I from screw press 618 is passed through line 623 into distillation tower 635 from holding tank 622. The distillation yields overhead distillate which is condensed via condenser at the top of distillation column 635 and is held in tank 637. Non-recoverable distillation discharge is accumulated in vessel 636. Overhead distillate from vessel 637 is then passed into charcoal column 638 and subsequently desorbed from charcoal column 638 and the desorbate is held in vessel 639.

Referring to FIG. 8, sugarcane leaves are conveyed via conveying means (such as a trailer truck) 70 into a screw conveyor 71 which leads directly into maceration means (grinder) 72. The macerated sugarcane leaves are then conveyed via cleated belt conveyor 73 into screw press 74. The screw press emits press liquor through line 76 past screen 77 and the press cake solids from screw press 74 are emitted through line 75 into a conveyor. Sludge discharge for recycling is passed into container 78. Fluid downstream from the screen is passed through pump 79 through line 701 into jacketed holding tank 702. The fluid from jacketed holding tank 702 is pumped using pump 703 through line 704 into distillation column 705 where it is fractionally distilled. The overhead distillate 707 is condensed and held for further processing at location 706.

Figure 9:
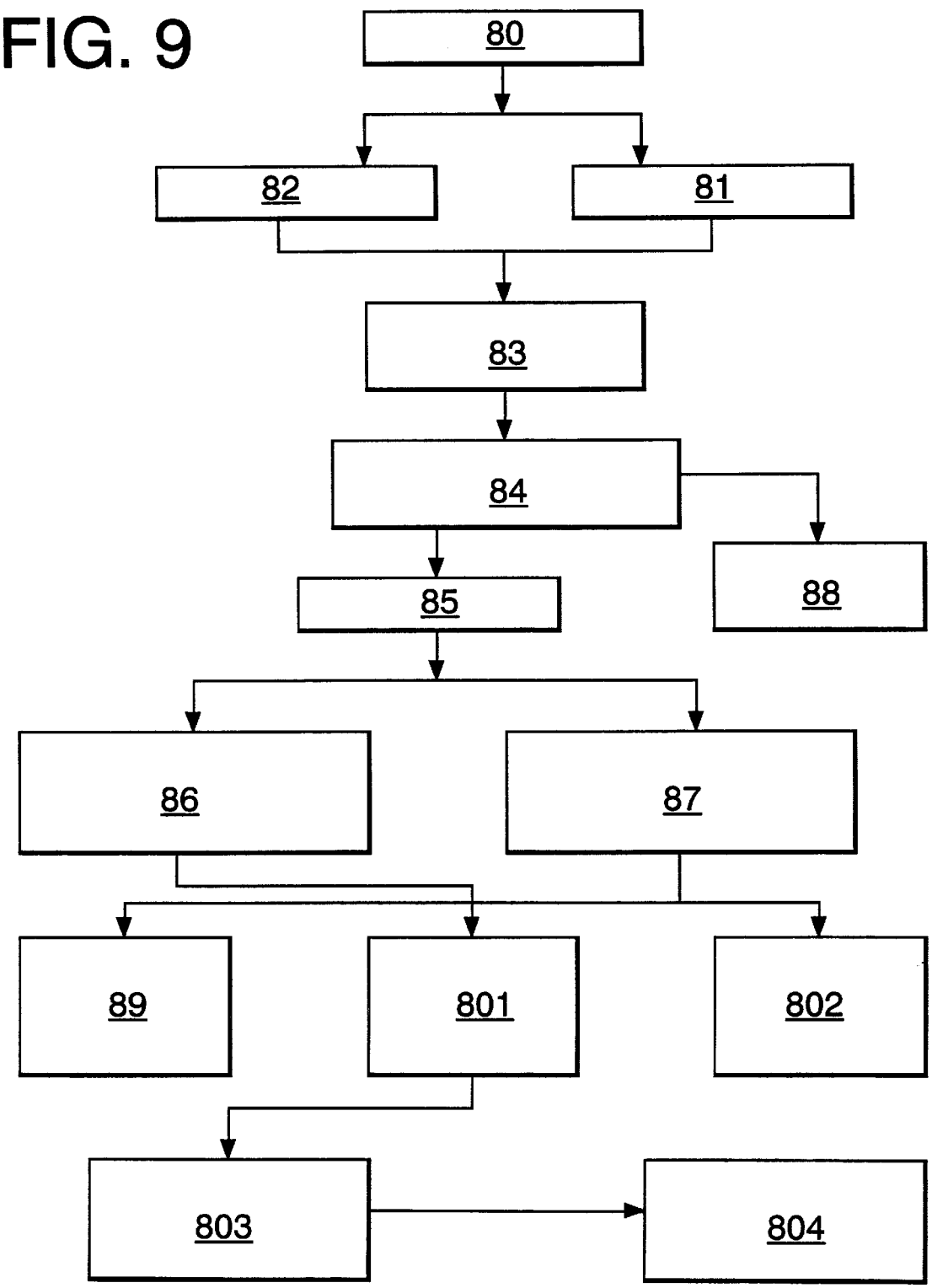
FIG. 9 is a schematic block flow diagram of apparatus used in Examples IV and V.

Referring to FIG. 9, sugarcane leaf at location 80 is divided into two parts, that part which is not ground or macerated is passed into location 82 and that part which is macerated is passed into grinder/cutter/shredder 81. The macerated and whole leaves are then combined and conveyed via cleated belt conveyor 83 into VINCENT® Screw Press, Model 22-P-40HP (40'×5'×10'/35 tons/hour) indicated by the reference numeral 84. Liquid from the screw press 84 is passed through SWECO Vibrating Screen-20 mesh indicated by reference numeral 85, and the resulting liquid is divided into two parts: a jacketed 500-gallon holding tank 86 and a jacketed 1,000-gallon holding tank 87. The press cake from the screw press 84 is conveyed through cleated belt conveyor 88 into a recycle tank.

The liquid from holding tanks 86 and 87 is then passed into three distillation units indicated by reference numerals 89, 801 and 802. Distillation product from distillation unit 801 is condensed and held in tank 803 and then passed into a pervaporation unit 804 where the product is passed through a pervaporation membrane as described in detail in FIGS. 16, 17, 18, 19, 20A, 20B, 21 and 22, infra.

Referring to FIG. 10A, sugarcane leaf at location 90 is divided into two parts: that part which is macerated is passed into grinder/cutter/shredder 92 and that part which is not macerated is passed into vessel 91. Conveyor 93 conveys macerated sugarcane leaf into cleated belt conveyor 95. Conveyor 94 conveys whole leaf from location 91 to cleated belt conveyor 95. Cleated belt conveyor 95 then conveys the mixture of macerated leaf and whole leaf through conveying means 96 to steam distillation tower 97. High-pressure steam from location 98 is passed into steam distillation tower 97, steaming the mixture of macerated and non-macerated sugarcane leaf. The resulting distillate is condensed in condenser 99 and then extracted under 50 atmospheres pressure in extraction unit 901 using 1,1,1,2-tetrafluoroethane. Condensate from condenser 99 is passed into extractor 901 where extraction solvent 1,1,1,2-tetrafluoroethane contacts the condensate under high pressure, e.g., 50 atmospheres. The solvent and extracted tastand is passed through drying column 902 and then into concentrator 904 where the solvent is evaporated. The aqueous phase from the extraction column is passed into vessel 903.

Referring to FIG. 10B, cane leaf from location 905 is conveyed into steam distillation apparatus 906. Steam distillate is condensed at location 907, and the condensate is subjected to pervaporation at location 908 with the pervaporation details set forth in the description of FIGS. 16, 17, 18, 19, 20A, 20B, 21 and 22.

An example of the screw press as indicated in FIG. 10B is set forth in U.S. Pat. No. 643,891 issued on Feb. 20, 1900 and is shown in FIG. 11. Thus, referring to FIG. 11, FIG. 11 is an elevation in section showing the construction of the screw press. FIGS. 11A, 11B, 11C and 11D are views illustrating the progressive diminution in the size of the strainer holes from the large to the small end of the tapered case. The screw press is shown by reference numeral 1000. The case or shell is tapered and supported on legs. A pipe or hollow shaft extends through the case. At the large end, this shaft turns in a hole or bearing in the closed head, and near the small end, the shaft turns in a bracket attached to the legs and projecting off from the small end. The small open end of the case is kept normally closed by a movable disk or plate, loose on the shaft, and a spring 1014 bears against this disk or plate and presses it to the small open end. In operation, when the pressure of the slurry of macerated sugarcane leaf and liquid in the case is sufficient to overcome the resistance of the spring (e.g., 2,000–5,000 psig), this plate will be forced away from the small end and allow the material to discharge through plates 1005, 1006, 1007 and 1008 and the like. The shell or wall of the case has slots or holes regularly spaced and extending all along and around the shell. These slots are rectangular in shape and shown in detail in FIGS. 11A, 11B, 11C and 11D. A lining of sheet copper is within the case and contacts with the shell or wall.

This lining is made in several sections or parts, one after the other, extending from the large end to the small end of the tapered case. Each section of the lining has strainer holes, those in the first section at the large end of the case being largest. These strainer holes vary from about 0.02 up to about 0.2 inches in diameter. By thus graduating the size of the strainer holes and gradually making them smaller from the large end to the small end of the tapered case, a very desirable action or operation is produced.

A feeding-in device of improved construction is provided and attached to the topmost cylinder, as indicated by reference numerals 1001, 1002 and 1003, and consists of a horizontally-placed tube 1003 whose curved end connects with an opening in the case wall. The other end of the feed tube is closed by a head, and near this end the tube has on top a funnel mouth or hopper 1001, and a shaft extends horizontally within the feed tube and projects through the head and on the outside has a pulley to be driven by a belt or chain. A compressing screw 1002 is on the shaft. This construction of horizontal tube with its end closed and its other end connecting with the case on the top insures that a supply of macerated sugarcane leaf may be continuously fed into the case under conditions that will keep the feed tube so choked or jammed full of macerated sugarcane leaf (and, as the case may be, in addition, whole sugarcane leaf) as to prevent escape of steam-pressure from the case. This construction and arrangement for horizontal feeding will operate satisfactorily, whether the mass of macerated sugarcane leaf that is being fed be either slightly wet or in a very wet condition.

The hollow shaft has on its outside end a pulley, and both ends of this shaft connect with suitable boxes. A steam pipe 1010 connects with one box and has a valve 1012 to govern the flow of steam that passes from a boiler to the hollow shaft. This shaft within the case has a tapered, spiraled flange or screw 1004 which fills the case and in revolving, just clears the lining of sheet copper. The shaft also has perforations 1011 extending along the entire length of the shaft so that at the large end of the case, where the compression of the macerated sugarcane leaf is very slight, steam will readily pass from the perforations 1011 and enter the mass of macerated sugarcane leaf and, as the case may be, whole sugarcane leaf. As the macerated and whole sugarcane leaf advances toward the small end, it gradually but rapidly becomes more and more compacted by the action of the tapered screw. A drain pipe 1009 leads from the valve 1013 and the open end of said pipe discharges into a tank or receptacle.

FIGS. 11A, 11B, 11C and 11D show plates 1005, 1006, 1007 and 1008, respectively, in detail, and these are also shown in FIGS. 11A, 11B, 11C and 11D by reference numerals 1005a, 1006a, 1007a and 1008a, respectively.

The apparatus of FIGS. 12A, 12B, 12C, 12D and 12E is shown and described in detail in United Kingdom 1,375,497 published on Nov. 27, 1974. Referring to FIG. 12A, FIG. 12A shows the discharge end portion of a screw press which generally includes a cylindrical cage 1110 which is constructed in two semi-cylindrical mating cage sections 1112, each having a plurality of parallel spaced, arcuate ribs integrally connected by longitudinally extending cage members. The cage sections 1112 are clamped together by a series of tie bolts which extend within the holes 1114, and the discharge end of the cage is supported by an upright end wall or member 1115 of the main frame. A plurality of screen bars 1116 are mounted on the ribs of each cage section 1112 and are circumferentially spaced to define longitudinally extending drainage slots or openings 1117 (FIG. 12B) therebetween. The screen bars 1116 are secured within each cage section by longitudinally extending retaining bars 1118 and cooperate to define a cylindrical pressing chamber 1120 having an inlet end and a discharge end 1122 which abuts the frame member 1115.

An elongated screw assembly 1125 extends through the pressing chamber 1120 and includes a hollow shaft 1126 (FIG. 12B) which is connected to a suitable drive motor 1128. A series of pressure worms, including a discharge worm 1129 and a final discharge worm 1130, are successively mounted on the shaft 1126 within the pressing chamber 1120 and are keyed to the shaft. The worm 1129 includes a cylindrical body 1132 and an integral helical flight 1133 which extends circumferentially around the body 1132 approximately 340°. A series of annular collars 1136 are mounted on the shaft 1126 interspaced between the pressure worms. A series of breaker bars 1138 are secured to the retaining bars 1118 and include lug portions which project inwardly into the pressing chamber 1120 in the areas of the annular collars 1136 and between the worms to minimize rotation of the macerated sugarcane leaf being pressed with the screw 1125. A final breaker bar or lug 1139 projects inwardly adjacent the discharge end of the final discharge worm 1130. The final discharge worm 1130 (FIGS. 12C and 12D) includes an annular body 1142 having an outer frusto-conical surface which tapers outwardly toward the discharge end of the screw assembly 1125. A pair of diametrically opposed helical flights 1144 are formed as an integral part of the body 1142, and each flight passes through a reference plane 1145 (FIG. 12C) and extends circumferentially approximately half way around the body 1142. Preferably, each of the helical flights 1144 extends circumferentially no greater than 200° and for an optimum angle of 170° so that opposing ends of the flights 1144 define diametrically opposed, axially extending passages or gaps 1146. A set of four uniformly spaced, axially extending, threaded holes 1148 (FIG. 12D) are formed within the discharge end of the worm 1130, and as mentioned, supra, all of the worms, including the worms 1129 and 1130, are secured to the shaft 1126 by keys which extend within corresponding keyways 1149.

A cylindrical collar 1152 (FIG. 12B) is mounted on the shaft 1126 adjacent the discharge end of the worm 1130, and a pair of diametrically spaced, threaded holes 1153 are formed within the collar 1152. A final cylindrical collar 1154 is mounted on the end portion of the shaft 1126 and has an outer diameter the same as the collar 1152. A counterbore 1156 (FIG. 12B) is formed within the end of the collar 1154 and is adapted to receive a circular retaining plate which is secured to the end of the shaft 1126 by suitable screws and functions to assure that the worms and collars do not shift axially on the shaft 1126. A large diameter counter bore 1159 (FIG. 12A) is formed within the frame member 1115 and receives a hardened discharge ring 1160 having a frusto-conical inner surface 1161 which continues inwardly onto a smaller adjacent discharge ring 1162. The discharge ring 1160 is retained by an annular plate 1164 which is secured to the frame member 1115 by a series of screws 1166. A non-rotatable discharge sleeve 1170 is mounted on the discharge collars 1152 and 1154 of the screw 1125 for axial sliding movement and has an outer frusto-conical surface 1172 which cooperates with the inner surface 1161 of the ring 1159 to define an annular discharge orifice 1175. An annular array of openings or holes 1176 are formed within the surface 1172 of the sleeve 1170 and provide for an inward escape of expressed tastand-containing fluid which drains from the sleeve 1170 through an outlet 1177 formed within the lower portion of a circular support or guide member 1178 secured to the end of the sleeve 1170.

A frame extension member or bracket 1180 is rigidly secured to the retaining plate 1164 and projects outwardly to support a double acting fluid or hydraulic cylinder 1182. The cylinder 1182 has a piston rod 1184 which is axially aligned with the screw assembly 1125 and supports the outer end of the sleeve 1170 through the guide member 1178. The rod 1184 is slidably supported by a bearing 1185 mounted on the frame extension member 1180 and by a bearing 1186 mounted on the outer end of a guide tube 1187 rigidly secured to frame extension 1180. A grooved collar 1188 is secured to the rod 1184 and engages a tubular spline 1189 confined within the tube 1187 to prevent the rod 1184 and sleeve from rotating.

The compressed press cake for re-extraction, or for other use, is discharged through the annular orifice 1175. The discharge sleeve 1170 is positioned axially by actuating the fluid cylinder 1182 to adjust the area of the orifice 1175 according to the back pressure desired in the pressing chamber 1120. When the mechanical screw press has been in operation for a substantial period of time and it becomes desirable to replace the final discharge worm 1130, the hydraulic cylinder 1182 is actuated, and the discharge sleeve 1170 is retracted from the discharge ring 1160. The sleeve 1170 is then removed from the guide member 1178, and the retaining plate is removed from the counterbore 1156 within the end portion of the final collar 1154.

The guide member 1178 is provided with a set of diametrically spaced, axially extending holes 1191 which receive a corresponding pair of elongated bars or rods 1192, each having a threaded forward end portion and a plurality of axially spaced neck portions 1194. A spring clamp 1195 (FIGS. 12A and 12E) is adapted to engage one of the neck portions 1194 of each rod 1192 and includes a U-shaped flat spring 1196 having end portions secured to a paired of mating block members 1198 by a set of screws 1199. The block members 1198 are urged together by the spring 1196 and cooperate to define a cylindrical bore 1101 having a diameter approximately the same as the neck portions 1194 and rods 1192. A tapered surface 1102 is formed on each block 1198, and these surfaces cooperate to provide a lead for pressing each of the spring clamps 1195 onto a neck portion 1194 of the corresponding rod 1192.

After the discharge sleeve 1170 is retracted from the screw 1125 and removed, a main shaft extension 1105 is secured by a set of screws 1106 to the end of the screw shaft 1126 in place of the retaining plate. The shaft extension 1105 includes a cylindrical portion 1108 having an outer diameter slightly less than that of the shaft 1126, and a lead portion 1110 has a slightly frusto-conical outer surface which tapers from the outer surface of the shaft 1126 to the outer surface of the cylindrical portion 1108.

As illustrated in FIG. 12A, the fluid cylinder 1182 primarily functions to position the discharge sleeve 1170 and to control the size of the annular discharge orifice 1175. However, the cylinder 1182 can also be used to aid in removing the collars 1154 and 1152 and the final discharge worm 1130 from the screw shaft 1126 and may be used for removing all members fitted and keyed to the shaft 1126. This is accomplished by simply extending the rods 1192 through the bores 1191 and threading the end portions of the rods into the corresponding axially extending, threaded holes 1153 within the final collar 1154. The piston rod 1184 is extended to position the guide member 1178 as shown in FIG. 12B, and the spring clamps 1195 are pressed onto the neck portions 1194 of the rods 1192 in back of the guide member 1178. The piston rod 1184 and the guide member 1178 are then retracted to pull the end collar 1154 from the shaft 1126 and onto the shaft extension 1105.

After the collar 1154 is removed, the pulling operation is repeated again to remove the adjacent collar 1152 and again to remove the final discharge worm 1130 and again for each worm and collar which is desired to be removed from the shaft 1126. However, before the worm 1130 is pulled from the shaft 1126, the gap 1146 between the ends of the helical flights 1144 is aligned with the last breaker bar lug 1139 by rotating the screw 1125. The rods 1192, the guide member 1178 and the fluid cylinder 1182 may also be used for mounting a new final discharge worm 1130 on the screw shaft 1126 and also for replacing the final collars 1152 and 1154. That is, the new final discharge worm 1130 is placed on the main shaft extension 1105, and the rods 1192 are threaded into two of the holes 1148 of the worm 1130. The spring clamps 1195 are then pressed onto neck portions 1194 of the rods 1192 in front of the retracted guide member 1178, and the piston rod 1184 is extended so that the worm 1130 is pushed or forced back onto the screw shaft 1126 and adjacent the collar 1136. The plurality of neck portions 1194 on each rod 1192 enables the pulling operation for removing the worm 1130 or the pushing operation for replacing a new worm 1130 is to be performed in successive steps simply by resetting the spring clamps 1195 to another set of neck portions 1194 of the rods 1192.

Figure 13:
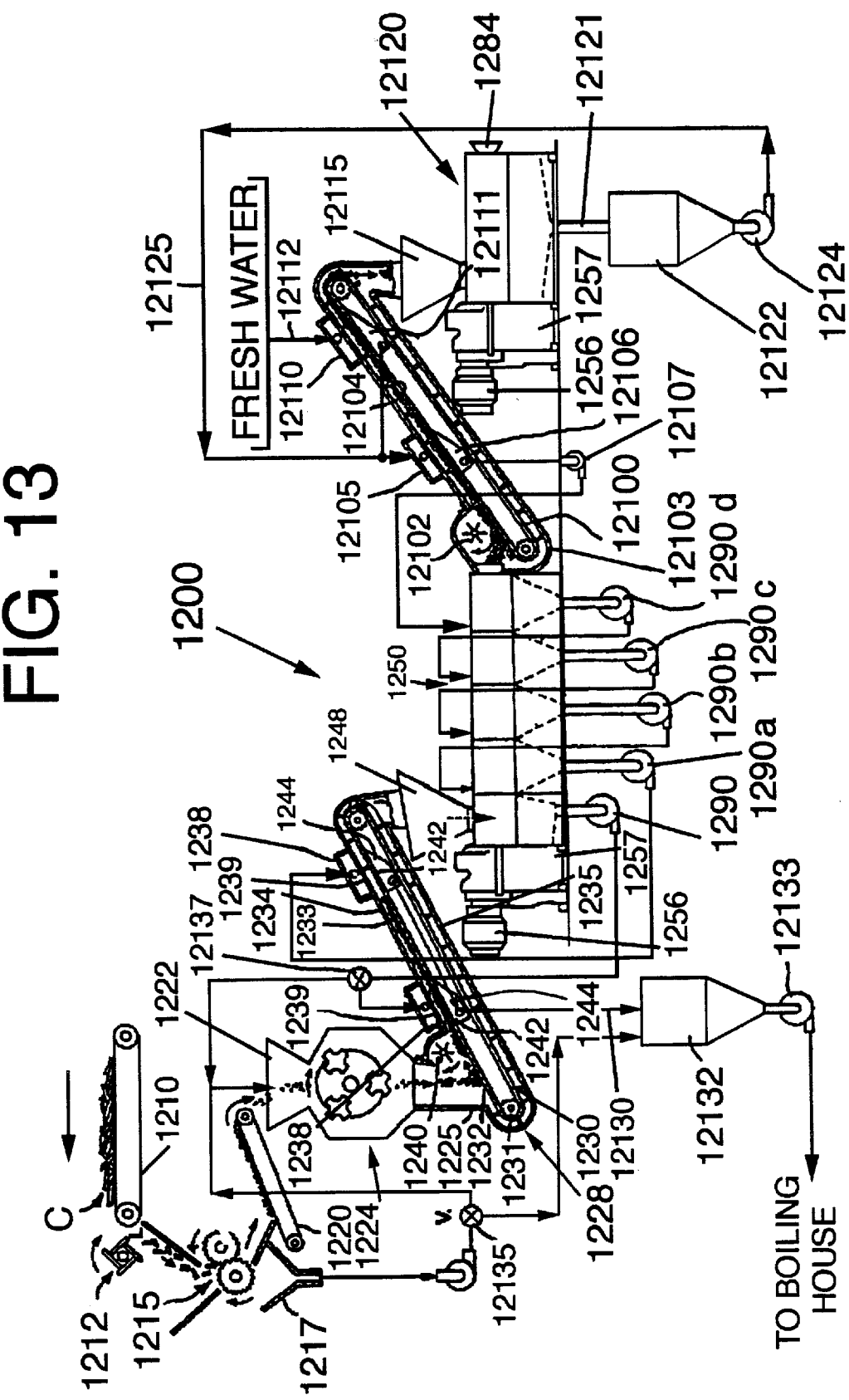
FIG. 13 is a cutaway side elevation view in schematic form of apparatus including sugarcane cutting means, conveying means and hydraulic press means useful in carrying out the process of Example II of our invention and is described in detail in U.S. Pat. No. 3,661,082 issued on May 9, 1972, the specification for which is incorporated by reference herein.

FIG. 13 sets forth apparatus including a mechanical screw press having sequentially arranged drainage cage sections as fully described in U.S. Pat. No. 3,661,082 issued on May 9, 1972, the specification for which is incorporated by reference herein.

Referring to FIG. 13, macerated sugarcane leaf and, if desired, whole sugarcane leaf material is fed by conveyor 1210 into a maceration device 1212 and then through a crusher 1215 where an initial portion of juice is released from the macerated sugarcane leaf material and is collected within the receptacle 1217. The crushed material is fed by the conveyor 1220 directly into the inlet hopper 1222 of a shredder 1224.

The shredded material which is discharged from the shredder 1224 is directed into a bin or hopper 1225 formed at the lower end of an inclined drag conveyor 1228. This conveyor includes a pair of endless chains 1230 directed around sprockets 1231 and carrying a series of laterally extending drag slats 1232. The upper reach of the inclined conveyor is partially supported by an intermediate wall 1233 extending between the upper conveyor housing wall 1234 and lower wall 1235.

A pair of manifolds 1238 are mounted on the upper wall 1234 in vertically spaced relationship, and each manifold is adapted to receive a flow of liquid extract containing tastand. These manifolds include openings 1239 directing the maceration liquid containing tastand through the bed of the material produced by a rotary leveling member 1240 positioned in the hopper 1225 in spaced relationship with the conveyor drag slats 1232. A series of openings 1242 are formed in the intermediate wall 1233, generally opposite each group of manifold openings 1239, and open into corresponding collecting pans 1244 mounted on the underneath surface of the intermediate wall 1233 for collecting the maceration liquid (extraction liquid containing tastand) which filters through the bed of material.

The bed of material on the conveyor 1228 is discharged into the inlet hopper 1248 of a special mechanical screw press 1250. The first or feed end section of this press surrounds a feed worm and is made up of a plurality of spaced apart screen bars. The worm may be interrupted at one or more locations, and in these interruptions, radially adjustable breaker bars or lugs are mounted extending toward the center of the feed worm between its sections. As is well known, these lugs provide resistance to rotation of the material and assist in creating pressure upon the macerated sugarcane leaves, which results in expression of tastand-containing liquids that drain through the spaces between the screen bars. The drive for this press is provided by a suitable motor 1256 which is connected through a gearbox 1257 to rotate a sleeve connection 1258 that is connected to rotate the feed worm at a predetermined higher speed and also to rotate at a slower speed in the internal shaft, which has a splined end extending into the transmission box.

The feed worm conveys and discharges the press cake into the first of a plurality of dewatering or drainage cage sections. Within each of these sections, there are worm members which are suitably connected to the shaft, as through a key to rotate therewith at the slower speed and force material toward the discharge of the press. This ring may be adjustable toward and away from the final drainage sections to adjust the size of the annular discharge orifice. Between the worms in each section, there are collars and the final worm in each section increases in size to a larger diameter on its downstream edge, this larger diameter being greater than the diameter of the succeeding collar. Radially outward, preferably spaced somewhat from the collars, there are breaker lugs or bars which resist rotation of the material and thus assist in the compaction and working of the macerated sugarcane leaf material as it progresses from one worm to the next. Downstream from the final worm, there is a discharge collar which cooperates with the discharge ring to define the discharge orifice from which the material exits the press. A nut is fastened to the end of the shaft and holds the entire assemblage of worms and collars in place on the shaft. If desired, the collars may be free to rotate on the shaft as described in U.S. Pat. No. 3,092,017, the specification for which is incorporated by reference herein, and the discharge collar may be mounted stationary on the press cage structure, also as disclosed in said U.S. Pat. No. 3,092,017.

The tastand-containing liquid, expressed from the macerated sugarcane leaf material and passing through the spaces between the screen bars, is collected in at least several separate sumps or bins, corresponding to the feed inlet or inlet section and to the expression cage sections. The discharge from each of these sumps is directed to the inlet of a recirculating pump, these being designated at 1290, 1290*a*, 1290*b*, 1290*c* and 1290*d*, respectively. The outlets of the last three of these pumps are directed to the supply pipes for the injector bars of the preceding stage. The discharge from pump 1290 is connected to the manifold 1238 on the lower end of the conveyor 1228, and the discharge from pump 1290*a* is connected to the upper manifold 1238 at the top of this conveyor. Thus, sugarcane leaf maceration liquid expressed from and drained away from the final stages of the press is recirculated back through the material passing through the initial stages of the press. It should be understood that more sections and additional circulating paths can be provided, if desired, within the concept of U.S. Pat. No. 3,661,082 and of this invention.

The sugarcane leaf press cake discharged from the countercurrent injection press is directed onto a further conveyor 12100 provided with a leveling device 12102 which forms a bed of predetermined thickness on the upper flight of the conveyor. This conveyor is likewise surrounded by housing 12103 and provided with a lower manifold 12105 having a corresponding collecting tank or pan 12106 beneath the upper flight of the conveyor. This pan 12106 is connected to the inlet of a pump 12107, which, in turn, pumps the liquid into the injector bars of the last drainage section. There is also an upper manifold 12110 having a corresponding collection pan 12111, which has its discharge connected to the inlet of the manifold 12105. Fresh sugarcane leaf maceration water is supplied through line 12112 into the upper manifold 12110. The material discharged from the conveyor 12100 is passed to the inlet hopper 12115 of a further screw press machine 12120, and liquid discharged in this second screw press passes through pipe 12121 into a collection tank 12122 and from that tank is recirculated by pump 12124 through line 12125 back to the lower manifold 12105 being added to the liquid drained through the material into the upper pan 12111.

The screw press cake containing pressed, macerated sugarcane leaf (and pressed sugarcane leaf as the case may be) discharged from the press 12120 has a relatively low moisture content, generally below approximately 50% moisture, and this press cake can be burned as fuel or put to other uses, as may be desired; or it may be recycled into yet another screw press.

The system provided using U.S. Pat. No. 3,661,082 incorporates numerous countercurrent flows of sugarcane leaf maceration liquid, beginning with the fresh sugarcane leaf maceration water added to the upper manifold of the second conveyor, or progressing through the material and through the several drainage sections of the first screw press 1250, then through the bed of macerated sugarcane leaf on the first conveyor 1230 with the liquid having the highest concentration of tastand being derived from pans 1244 and flowing through line 12130 into a collecting tank 12132 from which the liquid is pumped by the pump 12133 for further processing. Alternatively, raw liquid from the receptacle 1217 can be piped directly to tank 12132 by adjusting the diverter valve 12135, and in this condition, sugarcane leaf maceration liquid to the shredder 1224 can be obtained from the feed stage bin 1288 via pump 1290 by changing the diverter valve 12137.

Figure 14:
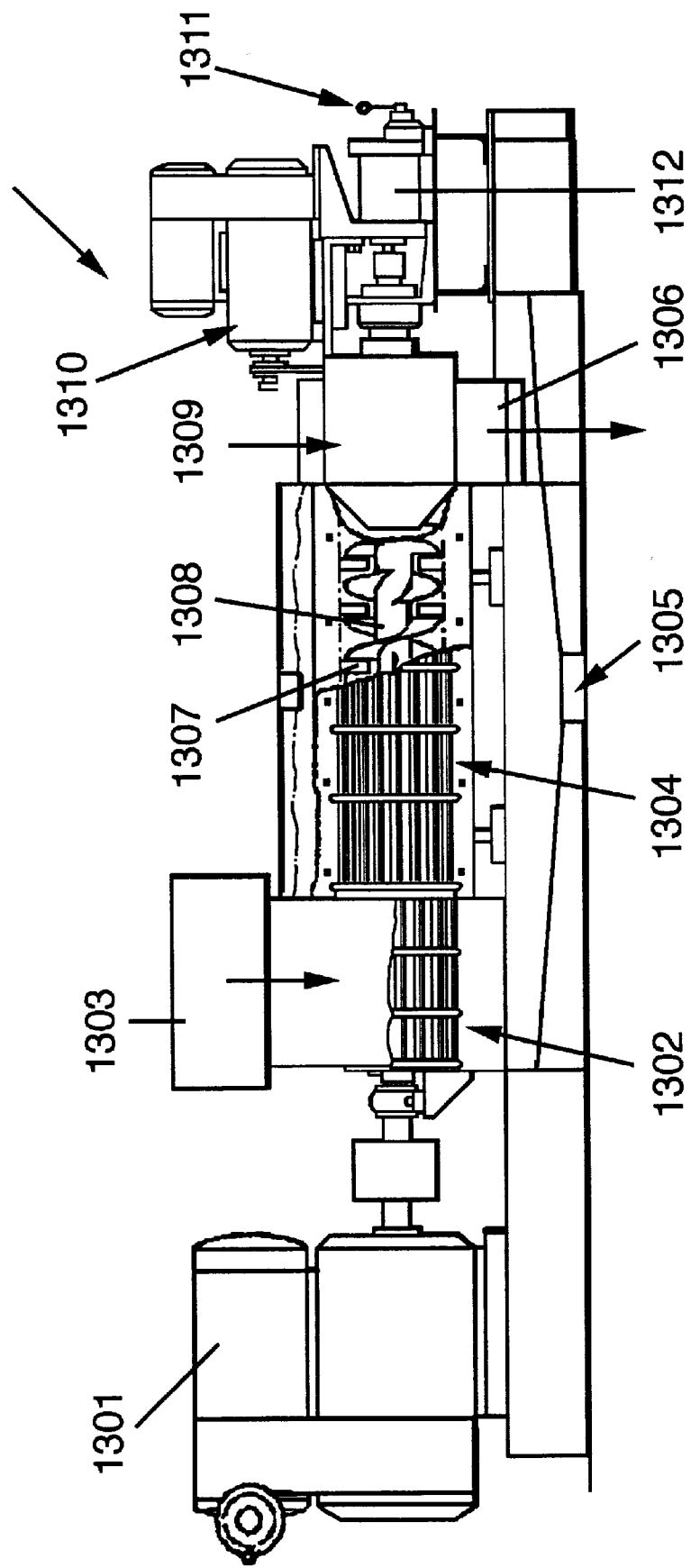
FIG. 14 is a cutaway side elevation view of a VINCENT® Horizontal Screw Press used in the practice of Example II and in the practice of Example IV of our invention, manufactured by the Vincent Corporation of 2810 Fifth Avenue, Tampa, Fla. 33601.

Referring to FIG. 14, the cutaway side elevation view of the VINCENT® Horizontal Screw Press, the main drive of the screw press is indicated by reference numeral 1301. Macerated sugarcane leaf and whole sugarcane leaf (if desired) is fed into hopper 1303 onto 180° hopper screen 1302. The maceration product and whole leaf product is then passed under pressure past 350° main screen with heavy fabricated frame 1304 during the operation of the screw spindle assembly 1308, which abuts resistor bar 1307. Extract containing tastand in the liquid phase is passed onto juice drain 1305 while press cake discharge is emitted thereafter. Simultaneously, cone drive 1310 is operated and adjusted using the cone positioning valve 1311 operated in conjunction with air cylinder 1312 and air-cushioned cone assembly 1309, the press cake being discharged from location 1306. The VINCENT® Horizontal Screw Press is produced by the Vincent Corporation of 2810 Fifth Avenue, Tampa, Fla. 33601.

Also useful in the practice of our invention is the VINCENT® CP-4 Screw Press, illustrated in detail in FIGS. 15A, 15B and 15C.

The CP-4 Screw Press is shown in general by reference numeral 1400. The press is operated using reversing drum switch 1401, and the shaft is held in place by a lock nut 1402 and is held in place using seal 1404. The press cake discharge evolves at location 1409 and is adjusted using handle 1411 held in place by cone adjustment screw 1410.

The cone 1407 is kept under pressure using spring 1412 contained in spring container 1413 and held in place with bracket 1414. At the cone-end of the shaft, the shaft is rotated on bearing 1409. Simultaneously, tastand-containing liquid is evolved through screen 1406 from the screw-end of the shaft, and the liquid is then discharged through orifices 1403 and 1415. The tastand-containing liquid is further processed as by means of pervaporation as shown in detail in the description of FIGS. 16, 17, 18, 19, 20A, 20B, 21 and 22, infra.

Figure 16:
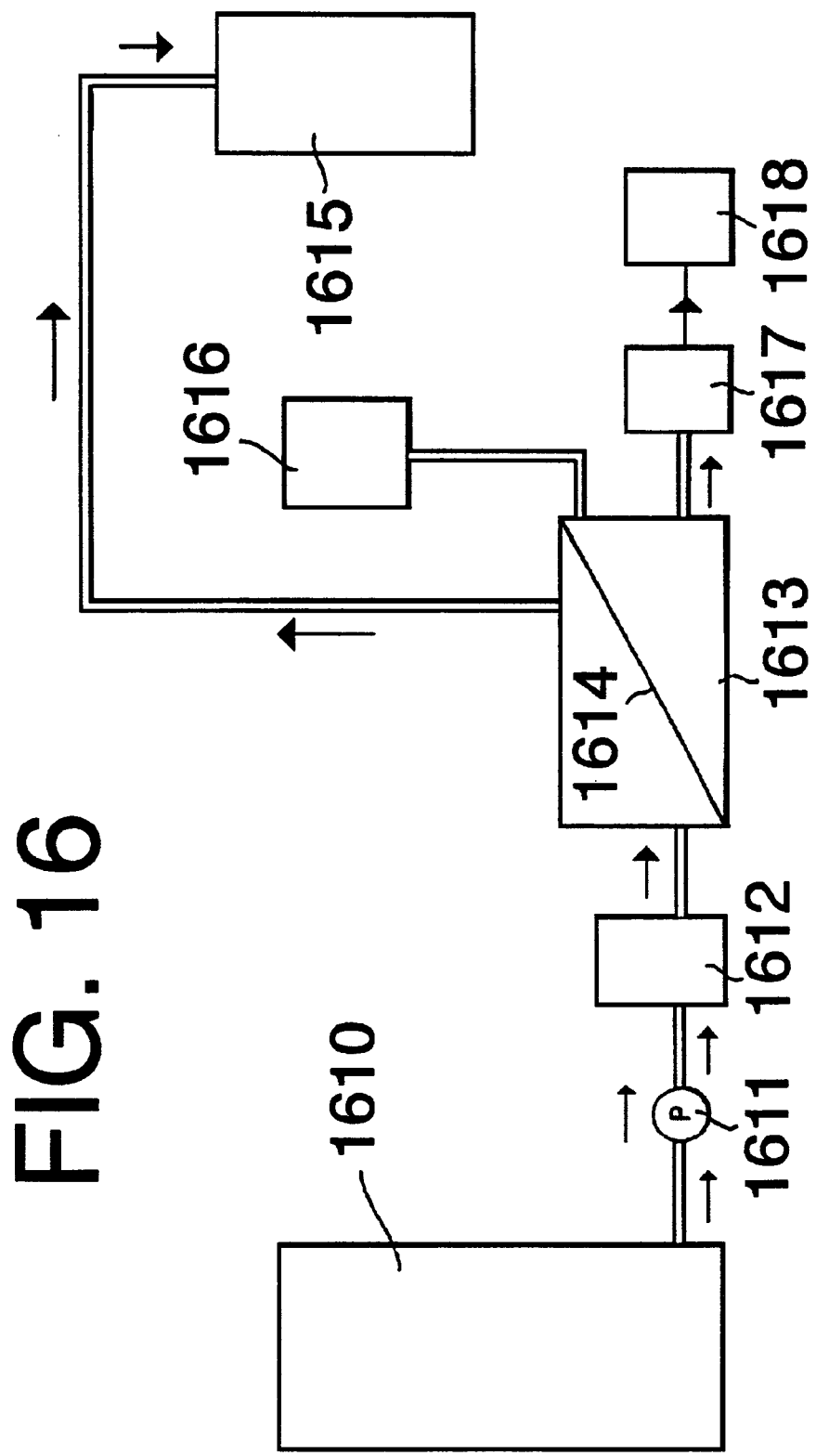
FIG. 16 is a schematic block flow diagram showing an aspect of the pervaporation process of our invention as described in detail in Example IV.

Referring to FIG. 16, tastand-containing liquid, for example, that from vessel 803 shown on FIG. 9, described, supra, is pumped into tank 1610, and tastand-containing liquid from tank 1610 is pumped using pump 1611 past heater 1612 into the pervaporation apparatus 1613 with the pervaporation membrane indicated by reference numeral 1614. Essence, for example, essence containing β-homocyclocitral having the structure:

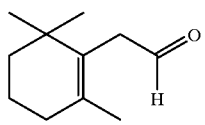

is evolved into container 1617 which is condensed at location 1618. Vacuum is applied to the pervaporation membrane from vacuum pump 1616. Odor-free water with low BOD is evolved from the pervaporation apparatus at unit 1615.

Figure 17:
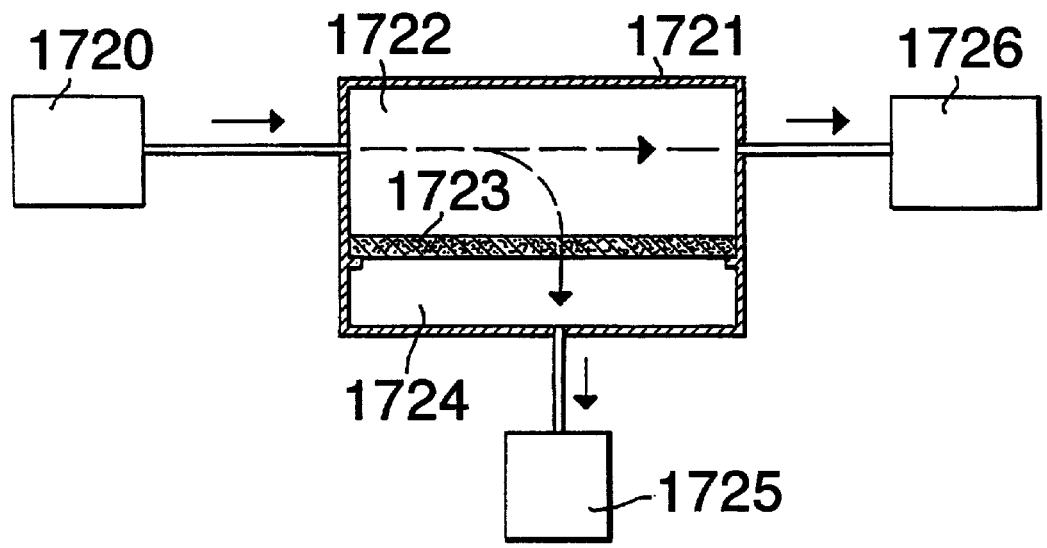
FIG. 17 is another schematic block flow diagram indicating permeation and evaporation in pervaporation apparatus as used in Example IV and also sets forth in schematic form that aspect of the process of our invention which includes the pervaporation step.

The membrane separation process is also shown in FIG. 17. In FIG. 17, tastand-containing liquid from location 1720 is pumped into the pervaporation apparatus 1721 with the input at location 1722, the pervaporation membrane at location 1723 and the essence-containing vapor (containing such materials as β-homocyclocitral having the structure:

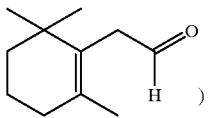

at location 1724. The essence-containing vapor is condensed at location 1725,and the liquid without the essence or with very little essence is collected at location 1726.

Figure 18:
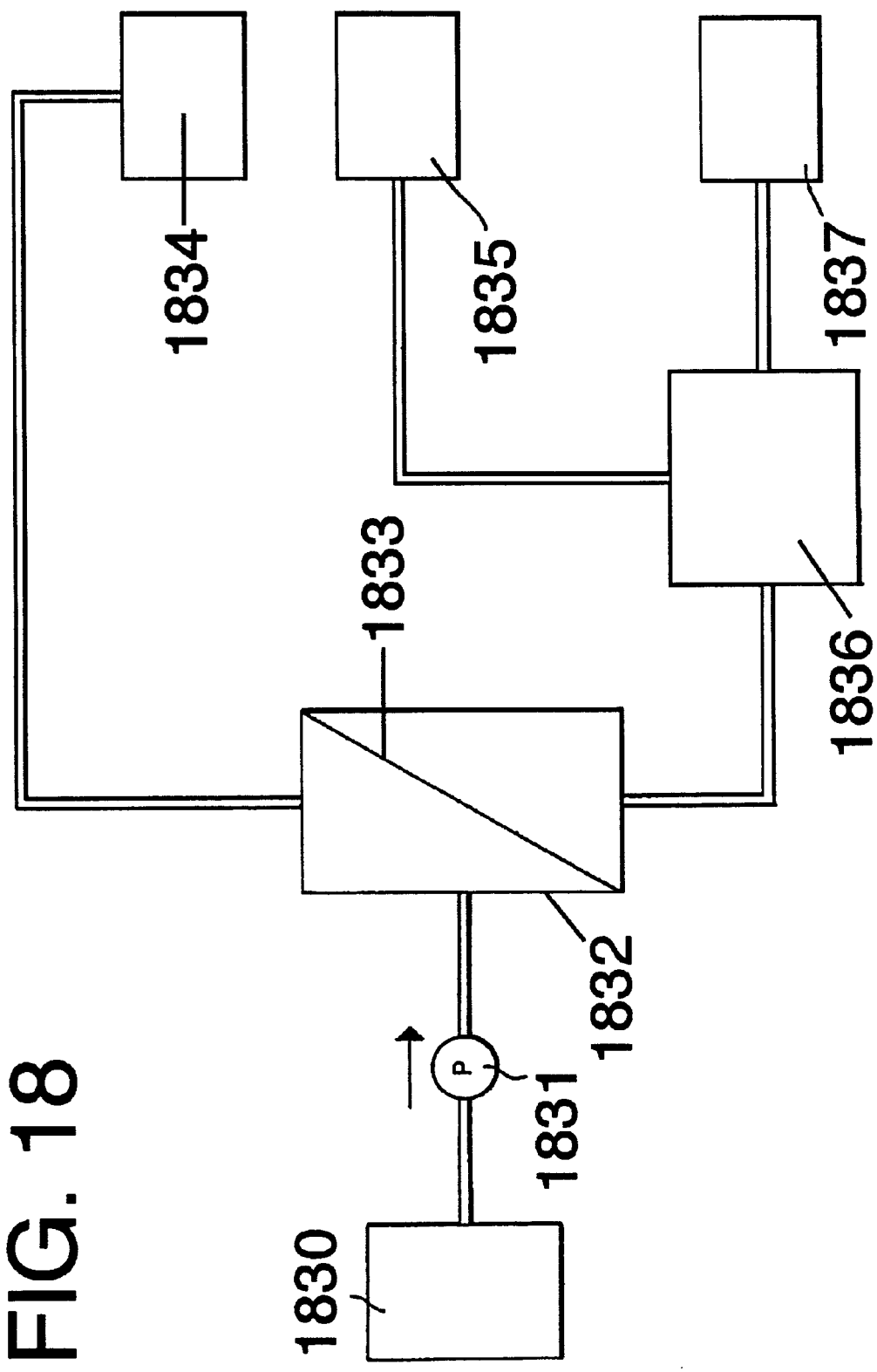
FIG. 18 is another schematic block flow diagram showing that aspect of the process of our invention which covers the pervaporation step as set forth in Example IV of our invention.

A simplified schematic diagram is set forth for the pervaporation aspect of our process in FIG. 18. In FIG. 18, feed from location 1830 is pumped through pump 1831 into pervaporation apparatus 1832 having pervaporation membrane 1833. Vacuum condenser system 1836 causes the gaseous essence (for example, containing β-homocyclocitral having the structure:

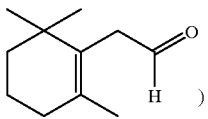

of the feed to be pulled through the pervaporation membrane whereby inerts are collected at location 1835 and condensed permeate (essence) is collected at location 1837. Meanwhile, residue (e.g., essence-free water) is collected at location 1834.

Figure 19:
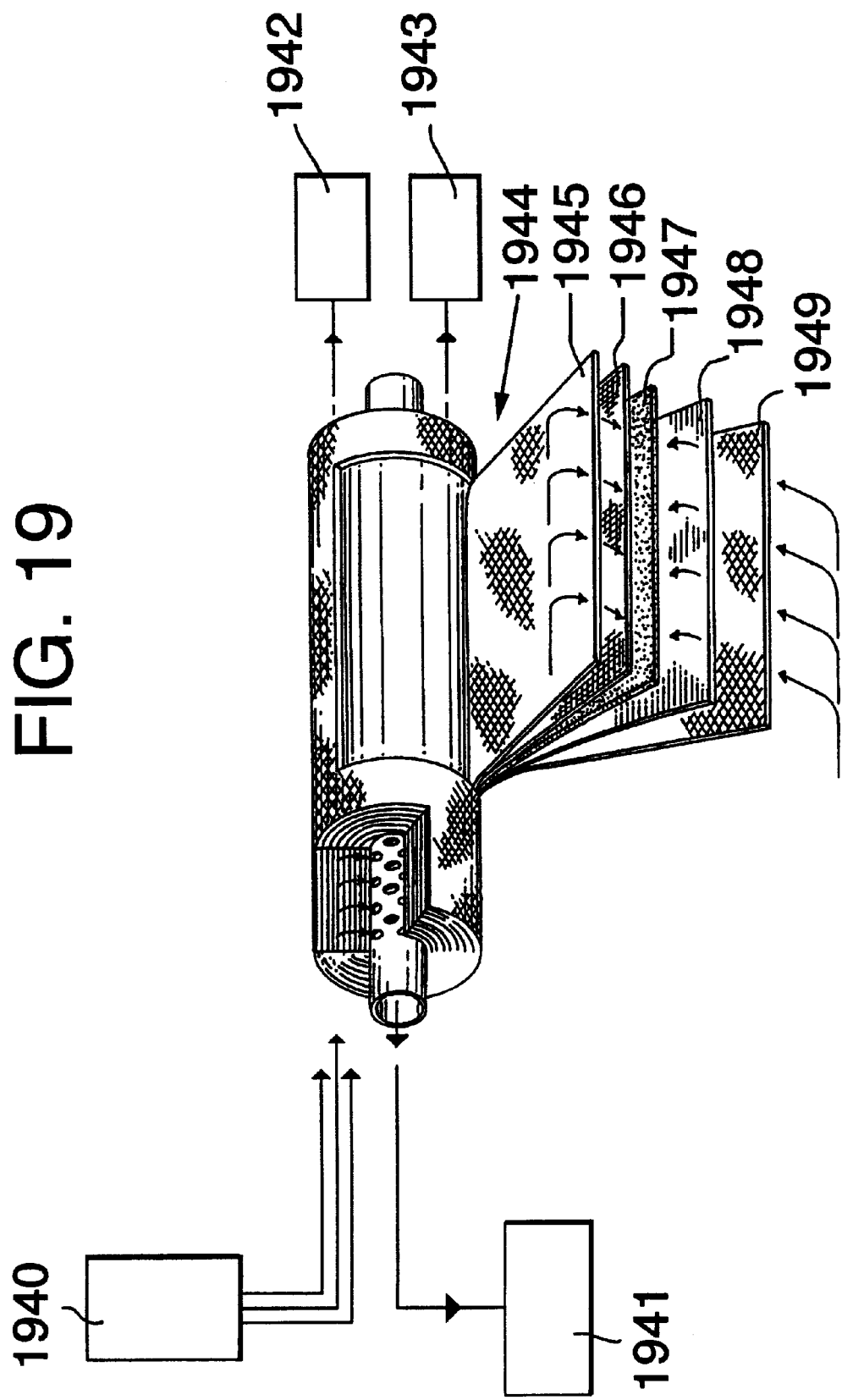
FIG. 19 is detailed, cutaway schematic diagram of a spiral-wound element configuration of the pervaporation apparatus used in the practice of Example IV of our invention, manufactured by Hoechst of Amsterdam, Netherlands.

A spiral-wound element configuration pervaporation apparatus is indicated in FIG. 19. Tastand-containing liquid feed from location 1940 enters the spiral-wound element 1944 and permeate exits from the spiral-wound element at location 1941. Residue is collected at locations 1942 and 1943. The spiral-wound element is "developed" from a drafting standpoint showing feed spacer 1945; membrane 1946; permeate spacer 1947; membrane 1948; and feed spacer 1949.

FIGS. 20A and 20B show the apparatus of U.S. Pat. No. 4,769,140 issued on Sep. 6, 1988, the specification for which is incorporated by reference herein. Referring to FIG. 20A, the apparatus for the separation of mixtures by means of pervaporation is shown. The apparatus contains end flange 2510 connected to middle flange 2514. The product inlets are shown at location 2509. The product channel is indicated at location 2501. The feed plate is indicated at reference numeral 2502. The end flange is indicated at reference numeral 2503. The middle flange is indicated by reference numeral 2514. The permeate space is indicated by reference numeral 2505. The feed space is indicated by reference numeral 2506. A feed inlet is indicated at reference numeral 2507, and the feed channel is indicated at reference numeral 2508.

Referring to FIG. 20B, FIG. 20B shows a module stack possessing a joint, raw feed inlet 2526 and a joint, raw feed product outlet 2527 for all raw feed chambers. Each module unit comprises two plates indicated by reference numeral 2056 arranged in mirror module image form. Each plate has a surrounding profile 2055 with raw feed inlet and outlet channels 2526 and 2527. The individual channels 2526 and 2527 form a complete inlet or outlet channel, respectively. The inlet channel is connected via a hole 5260 in a plate 2550 or 2551, respectively. These holes form the product inlet for the assembled unit. The permeate, i.e., the product that has passed through the membrane 2536, leaves the individual units sidewise. The sealing 2546 is only sealing the space surrounding the holes 2526. The outlet holes 2527 of each unit are interconnected to form an outlet channel. This outlet channel is connected via an opening 5261 in the middle flange 2551 or, respectively, in the end plate or end flange 2552 to conduits for further processing. The module units are held together between middle flange 2551 and end plates 2550 and 2552. The plates are forced together, pressing the plates 2056 into sealing engagement with the seals surrounding holes 2526, 2527 and with the seals surrounding the inlet and the outlet opening to and from feed chambers 2051 and 2052 by tie bolts 5270 with nuts 5271 and spring washers 5272. The feed space or feed chamber 5120 and the permeate space or permeate chamber 5130 are separated from each other by membranes 2536.

Figure 21:
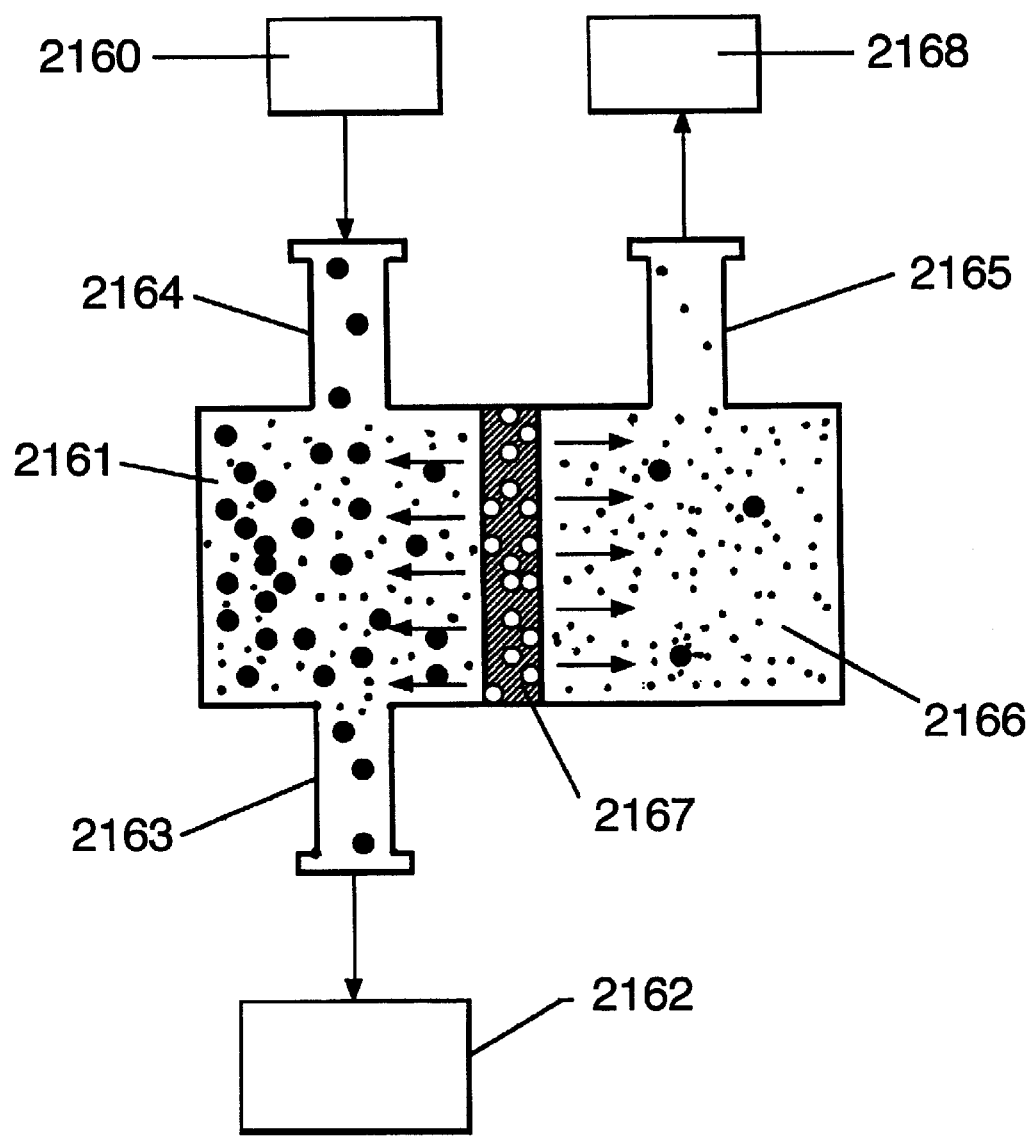
FIG. 21 is a schematic diagram of the inner workings of pervaporation apparatus showing the use of the pervaporation membrane and the location of feed, vaporous permeate and product containing the tastand which is a tastand of our invention.

The simple pervaporation module itself is shown in schematic form in FIG. 21. Referring to FIG. 21, feed from location 2160 enters the entry port for the pervaporation device at 2164. The product is subjected to pressure at location 2161, and product without much of the essence passes through channel 2163 to location 2162. Across pervaporation membrane 2167, gaseous product (for example, containing β-homocyclocitral having the structure:

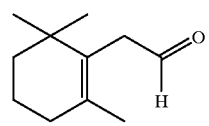

and damascenone having the structure:

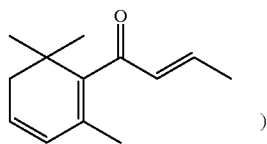

enters the three-space 2166 and exits via channel 2165 to location 2168. The driving force is equivalent to "chemical potential". The transport across the membrane is shown:

"Sorption→Diffusion→Desorption (Evaporation)"

Figure 22:
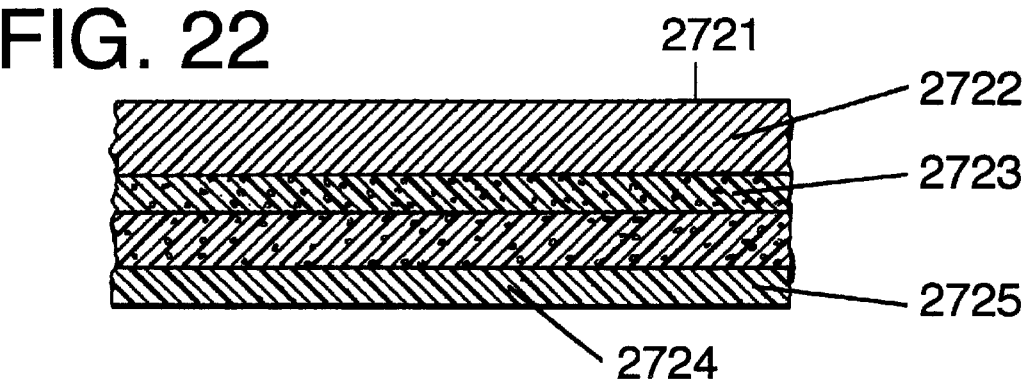
FIG. 22 is a cross section of a multilayer pervaporation membrane as disclosed in detail in U.S. Pat. No. 4,755,299 issued on Jul. 5, 1988 and incorporated by reference herein and assigned to GFT-Ingenieurbuero für Industrieanlagenplanung of Germany.

FIG. 22 shows in detail a multilayer membrane useful in the pervaporation apparatus useful in the process of our invention and useful in the operation of the process using the algorithm of our invention. FIG. 22 shows a multilayer membrane disclosed in detail in U.S. Pat. No. 4,755,299 issued on Jul. 5, 1988, the specification for which is incorporated by reference herein. Referring to FIG. 22, the multilayer membrane 2721 is comprised of a polymer fleece carrier layer 2722 having a thickness of 120 μm. Provided thereon is a porous backing layer 2723 of polyacrylonitrile having a layer thickness of 750 μm. Provided thereon is a porous intermediate layer (another backing layer) 2724 of saponified cellulose triacetate having a thickness of 750 μm. A nonporous separating layer 2725 of polyvinyl alcohol crosslinked with maleic acid has a layer thickness of under 1 μm. The production of that multilayer membrane is disclosed in Examples 5 and 6 of U.S. Pat. No. 4,755,299 issued on Jul. 5, 1988 and incorporated by reference herein.

FIGS. 23A, 23B, 23C and 23D show in detail Likens-Nickerson apparatus and "exploded" apparatus for the isolation of volatiles including the compounds:

damascenone having the structure:

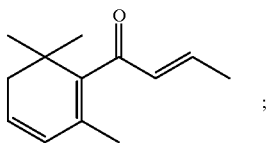

β-damascone having the structure:

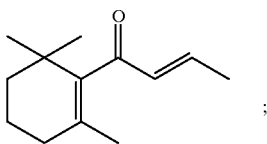

β-homocyclocitral having the structure:

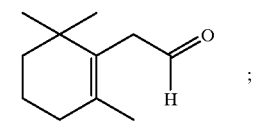

cis-3-hexenol having the structure:

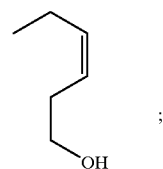

1-octen-3-ol having the structure:

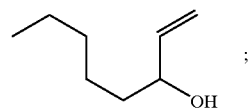

β-phenylethyl alcohol having the structure:

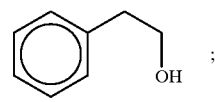

3-methyl-2-buten-1-ol having the structure:

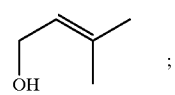

acetophenone having the structure:

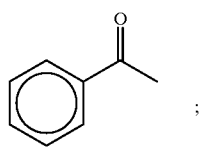

2,2,6-trimethyl cyclohexanone having the structure:

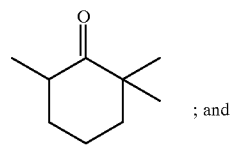

; and d-borneol having the structure:

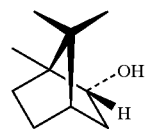

by means of simultaneous steam distillation and extraction.

Referring to FIG. 23A, the cooling device is indicated by reference numeral 2302. The cooling device fits into the upper framework opening 2310 and is sealably fitted therein via a glassware connection. Tube 2301 leads to fitting 2311*a* which fits with a vessel containing solvent. Tube 2372 leads to fitting 2311*b* which fits with a vessel containing aqueous liquid which contains the tastand to be extracted therefrom (e.g., distillate or pervaporate). Section 2307 of the framework is the holding volume for cooling apparatus 2302. Sections 2370 and 2371 contain the extract and raffinate of the aqueous substance being extracted with the solvent.

Referring to FIG. 23B, the cooling device 2302 is shown in place in the holding section of the apparatus 2307. Heater 2306 is shown as a heating coil for heating solvent 2314 located in solvent flask 2305. Heater 2304 is shown as a coil heater for heating and causing steam distillation of aqueous solution 2315 held in vessel 2303. In operation, the steam distillate of aqueous solution 2315 on being heated enters in the gas phase passageway 2327. The gaseous phase is then condensed at location 2307, and the condensate is mixed with vapors from the solvent flask 2305 of solvent 2314. The extracted material with solvent is shown at 2314a, and the residual aqueous phase is shown at location 2315a.

Referring to the apparatus showing the full steam distillation setup, FIG. 23C illustrates apparatus shown, overall, using reference numeral 2390. Flask 2303 is equipped with a second outlet through neck 2326 and opening 2325. Through opening 2325, steam is generated via steam tube 2324 from water container 2320 containing water 2321 and equipped with heater 2323. The heater, when engaged, causes evaporation of water 2321 into steam which travels through steam tube 2324 into aqueous liquid containing tastand 2315. Again, the steam distillate carrying a tastand such as d-borneol having the structure:

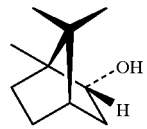

enters passageway 2327 and impinges upon the cooling apparatus at location 2307 and combines with solvent 2314 in the vapor phase heated by heating coil 2306 coming from vessel 2305 through tube 2301.

Referring to FIG. 23D, FIG. 23D is a Likens-Nickerson apparatus with vacuum jacket 2361 to minimize premature condensation and dry ice condenser 2351 coupled with heat exchanger 2352/2353 (condenser) to reduce volatilization losses. Solvent 2355 located in vessel 2359 is heated by heating coil 2356 and solvent in the gaseous phase passes through tube 2359. Simultaneously, aqueous composition 2357 containing tastand including such materials as d-borneol having the structure:

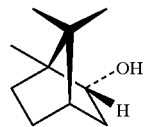

is heated using heating coil 2358 in vessel 2360, and the steam distillate passes through passageway 2362 past vacuum jacket 2361 to combine with solvent in the vapor phase coming from passageway 2354. The combined gasses pass through heat exchanger 2352/2353 to dry ice condenser 2351 and then condense and fall back into the framework of the apparatus. At the end of the procedure, valve 2363 is opened to remove product which is subsequently analyzed for product and utilized for further experimentation.

The apparatus of FIGS. 23A, 23B, 23C and 23D is used in the practice of Example VIII, described in detail in the "EXAMPLES" section, infra.

The full operation of the apparatus of FIGS. 23A, 23B, 23C and 23D is described in detail at pages 82, 83, 84 and 85 of *PROGRESS IN FLAVOUR RESEARCH*, edited by D. G Land and H. E. Nursten (Proceedings of the Second Weurman Flavour Research Symposium held at the University of East Anglia, Norwich, England, Apr. 2–6, 1978), published by Applied Science Publishers Ltd of London, England.

The following examples are given to illustrate embodiments of the invention as it is presently preferred to practice it. It will be understood that these examples are illustrative, and the invention is not to be considered restricted thereto except as indicated in the appended claims.

EXAMPLE I

PREPARATION OF SUGARCANE LEAF EXTRACT USING APPARATUS OF FIG. 8

Two lots of sugarcane leaves (approximately 1 ton) were cut, pressed in the VINCENT® Screw Press illustrated in FIG. 14, and the aqueous juice so obtained was fractionally distilled.

Distillation was carried out in a 500 gallon still equipped with a 25 plate packed column. In the first run, run "A," 1,167 pounds of juice was distilled at a reflux ratio of 7:1 to yield 77 pounds of distillate (2 fractions). In the second run, run "B," 1,138 pounds of juice was distilled at a reflux ratio of 7:1 to yield 185 pounds of distillate.

Fractions 2 and 3 of run "B" were bulked and the bulked distillation fractions were analyzed using GC-capillary survey techniques. The results are set forth in FIGS. 2A and 2B.

In summation, a distillate obtained from one ton of mature sugarcane leaves contains approximately 12.48 grams of cis-3-hexenol and 0.79 grams of damascenone, together with approximately 70 other components.

EXAMPLE II

PRODUCTION OF SUGARCANE LEAF EXTRACT

Two lots of sugarcane leaves, 2,000 pounds of immature sugarcane leaves and 3,000 pounds of mature cane leaves, were cut, pressed using a VINCENT® Screw Press as in Example I, and the aqueous juice generated was fractionally distilled. 3 Fractions were obtained and subjected to redistillation yielding 5 fractions. Fractions 2, 3 and 4 of the redistillation fractions were bulked and extracted with an equal volume of diethyl ether.

The diethyl ether extract was concentrated whereby all of the diethyl ether was evaporated. The diethyl ether was analyzed using a GC-capillary survey, and the results are set forth in FIGS. 3A and 3B.

In summary, a distillate obtained from one ton of immature sugarcane leaves contains approximately 3.27 grams of cis-3-hexenol and 0.089 grams of damascenone; and a distillate obtained from one ton of mature sugarcane leaves contains 3.65 grams of cis-3-hexenol and 0.071 grams of damascenone.

EXAMPLE III

Using the apparatus and process set forth in schematic form in FIG. 7A, described, supra, 3,000 pounds of mature sugarcane leaves were pressed in a VINCENT® CP-4 Press set forth in FIGS. 15A, 15B and 15C. 1,400 Pounds of liquid extract containing tastand were yielded. 1,600 Pounds of press cake from the VINCENT® Press were placed in a second VINCENT® Press as set forth in FIGS. 15A, 15B and 15C, and 1,600 pounds of liquid extract were obtained. The liquid extracts were combined, heated in a heat exchanger and placed in a flash-distillation jacketed tank where the combined product was distilled, condensed and chilled. A total of 11 samples were analyzed by means of GLC analyses. 1,000 Grams of each sample was extracted with diethyl ether, the ether stripped and the crude extract analyzed by capillary GLC and GC-MS analyses. The percent composition of the various components were determined by $I_e$ values and mass spectral analysis data.

The following Table I sets forth the major chemical components and percentages (average for 11 samples):

| Component | Percentage |
|---|---|
| 2-phenyl-2-propanol | 0.048 |
| β-phenylethyl alcohol | 0.197 |
| betuligenol | 0.342 |
| acetic acid | 6.08 |
| isobutyl alcohol | 0.033 |
| isoamyl alcohol | 0.05 |
| cis-3-hexenol | 0.511 |
| damascenone | 0.057 |
| p-vinyl phenol | 0.346 |
| 1-penten-3-ol | 1.15 |
| cis-2-penten-1-ol | 0.65 |
| 1-octen-3-ol | 0.168 |
| phenyl acetaldehyde | 0.365 |
| octanoic acid | 0.154 |
| 2, 4-decadienal | 0.105 |

EXAMPLE IV

PRODUCTION OF SUGARCANE LEAF EXTRACT USING PERVAPORATION

Using the process and apparatus described in the description of FIG. 9, supra, a mixture of 3 tons of macerated, immature sugarcane leaves and 3 tons of immature sugarcane leaves was fed into the VINCENT® Press of FIG. 14, described in detail, supra.

The liquid evolved from the VINCENT® Press was stored in a 500 gallon vessel.

20 Gallons of the product was distilled. The distillation was run with a 4:1 reflux ratio for the first 10 gallons and then changed to 1:1 for the last 10 gallons. Fractions were collected for each 5 gallons distilled.

The resulting product was then run through the pervaporation system described in the detailed description of FIGS. 16, 17, 18, 19, 20A, 20B, 21 and 22, supra. Pervaporation conditions were:

150° F.;

vacuum 44 mm/Hg; and collection time: 45 minutes.

The resulting product was analyzed via GC-mass spectral analysis, and the analysis is set forth on FIG. 4.

EXAMPLE V

PRODUCTION OF SUGARCANE LEAF EXTRACT USING DISTILLATION AND PERVAPORATION

Using the apparatus as set forth and described in FIG. 9, supra, 36.5 tons of macerated, mature sugarcane leaves were placed into a VINCENT® Press as shown in FIG. 14 and as described in detail, supra. 250 Gallons of liquid tastand-containing extract were obtained from the VINCENT® Press.

The 250 gallons were placed in an 8-plate 300 gallon still and heated to 100° C. at full reflux.

The reflux ratio was then changed to 4:1, and 5 gallons of distillate were obtained.

The reflux ratio was then changed to 1:1, and 20 gallons of distillate were obtained over a period of 8 hours.

Thus, a total of 25 gallons of distillate were obtained from 250 gallons of VINCENT® Press extract.

The resulting distillate (25 gallons) was subjected to pervaporation using the apparatus of FIGS. 16, 17, 18, 19, 20A, 20B, 21 and 22 at conditions of 40 mm/Hg pressure and at a inlet temperature of 150° F. and an outlet temperature of 20° F. The total pervaporate product was 1,350 grams. The pervaporate product was analyzed via GC-mass spectral analysis, and the analyses are set forth at FIGS. 5A and 5B and described in the DETAILED DESCRIPTION OF THE DRAWINGS, supra.

EXAMPLE VI

PREPARATION OF SUGARCANE LEAF EXTRACT

Using the apparatus and carrying out the process as set forth in FIG. 7B described in detail in the DETAILED DESCRIPTION OF THE DRAWINGS, supra, 1,650 pounds of sugarcane leaves was macerated and placed in a screw press described according to the description of FIGS. 15A, 15B and 15C, supra. 500 Pounds of extract I (liquid phase) was obtained on operation of the screw press, and simultaneously, the press cake was admixed with an additional 600 pounds of water. The mixture of press cake from the first screw press and 600 pounds of water was placed into a second screw press also described according to the description of FIGS. 15A, 15B and 15C. 100 Pounds of extract was obtained from the second screw press (extract II). The two extracts were simultaneously fed into a distillation column, and on distillation, 185 pounds of concentrate was obtained. The resulting concentrate was passed through an activated charcoal column where the charcoal adsorbed tastand contained in the distillate.

500 Grams of the adsorbed charcoal was then packed into a glass column and steam distilled. The first fraction of distillate (0.69 grams) separated as oil and was rich in dimethyl sulfide. The distillation was continued yielding 8 fractions. Each of the 8 fractions was combined, admixed with an equal volume of saturated, aqueous sodium chloride solution and extracted with diethyl ether. The resulting diethyl ether extract was dried over anhydrous magnesium sulfate and stripped of solvent, yielding 2.6 grams of oil.

The resulting product was analyzed via GC-mass spectral analysis, and these analyses are set forth in FIGS. 6A and 6B, described in the DETAILED DESCRIPTION OF THE DRAWINGS, supra.

EXAMPLE VII

PRODUCTION OF SUGARCANE LEAF EXTRACT USING STEAM DISTILLATION

Using the apparatus of FIG. 10A and the process described in the description of FIG. 10A in the DETAILED DESCRIPTION OF THE DRAWINGS, supra, 3.5 tons of a 50:50 mixture of macerated and non-macerated, immature sugarcane leaves was placed in a VP-22 VINCENT® Press using an 80 psig back pressure. The resulting liquid phase extract weighed 1,000 pounds.

The resulting product was then placed in a steam distillation tower, and steam was passed through the tower at a pressure of 2.5 psig for a period of 30 minutes, yielding 70 gallons of product.

The resulting product was then extracted under 50 atmospheres pressure using 1,1,1,2-tetrafluoroethane as an extraction agent.

The resulting extract was evaporated, and the recovered 1,1,1,2-tetrafluoroethane was recycled for additional use. The recovered product was used as a tastand in Examples IX, X and XI.

EXAMPLE VIII

DETERMINATION OF FLAVOR CHARACTERISTICS OF PERMEATE OF EXAMPLE V

A Likens-Nickerson extraction using 200 grams of diethyl ether and 3,200 grams of permeate produced according to Example V was carried out using the apparatus of FIG. 23B. The permeate was extracted continuously until the taste of the water did not have the presence of aroma. After stripping the solvent, approximately 0.5 grams of an oil was obtained. The odor of this oil was then matched with different proportions of the materials listed below with previously prepared, 1% ethanol solutions of each chemical produced.

EXAMPLE VIII(A)

1% Solutions of each of d-borneol, 3-methyl-2-buten-1-ol, acetophenone, damascenone, 2,2,6-trimethylcyclohexanone, β-homocyclocitral and 1-octen-3-ol were prepared in 95% ethyl alcohol. 0.8734 Grams of the 1% solution of borneol; 0.8734 grams of the 1% solution of the 3-methyl-2-buten-1-ol; 1.74 grams of the 1% solution of acetophenone; 2.61 grams of the 1% solution of damascenone; 1.74 grams of the 1% solution of 2,2,6-trimethylcyclohexanone; 0.8734 grams of the 1% solution of β-homocyclocitral; and 1.74 grams of the 1% solution of 1-octen-3-ol solution were combined. A 60 ppm solution was then prepared. The resulting solution was further diluted to 6 ppb (parts per billion) using DIET PEPSI COLA® as the diluent. The resulting "DIET PEPSI COLA® " removed the bitter aftertaste and improved the sweetness of the beverage, when the solution was added to the DIET PEPSI COLA® at the rate of 10%.

EXAMPLE VIII(B)

A 1% solution of each of the following materials was prepared in 95% food grade ethanol:
(i) cis-3-hexenol;
(ii) 1-octen-3-ol; and
(iii) damascenone.

0.8734 Grams of each of the 1% solutions of the cis-3-hexenol, damascenone and 1-octen-3-ol were weighed into a tared 0.5 ounce bottle. The solutions were then mixed together. From the resulting solution, a 60 ppm solution was produced in distilled water, which was further made into a 6 ppb solution (parts per billion) using DIET PEPSI COLA® as the diluent. The resulting DIET PEPSI COLA® (trademark of the Pepsi Cola Company) has no bitter aftertaste.

EXAMPLE VIII(C)

1% Solutions of each of the following materials were diluted to levels of 6 ppb in DIET PEPSI COLA®:

(i) cis-3-hexenol;
(ii) damascenone; and
(iii) 1-octen-3-ol.

At 6 ppm, the damascenone in DIET PEPSI COLA® masks the bitter taste and enhances sweetness.

The 1-octen-3-ol at 6 ppb in DIET PEPSI COLA® does not mask the bitter taste.

The cis-3-hexenol at 6 ppb in DIET PEPSI COLA® does not mask the bitterness.

EXAMPLE VIII(D)

The following mixtures were prepared:
(i) 6 ppb damascenone with 6 ppb 1-octen-3-ol in DIET PEPSI COLA®;
(ii) 6 ppb damascenone with 6 ppb cis-3-hexenol in DIET PEPSI COLA®; and
(iii) 6 ppb cis-3-hexenol with 6 ppb 1-octen-3-ol in DIET PEPSI COLA®.

Mixture (i) masks the bitter taste and enhances the sweetness in DIET PEPSI COLA®.

Mixture (ii) masks the bitter taste and enhances the sweetness in DIET PEPSI COLA®.

Mixture (iii) masks the bitter taste and enhances the sweetness in DIET PEPSI COLA®.

EXAMPLE VIII(E)

1% Solutions of each of the following materials were prepared in 95% food grade ethanol:
(i) β-phenylethyl alcohol;
(ii) damascenone;
(iii) β-homocyclocitral;
(iv) cis-3-hexenol; and
(v) acetophenone.

On dilution of each of the corresponding 1% solutions in deionized water, 60 ppm and 10 ppm solutions were prepared. The resulting solutions were then further diluted to produce solutions in DIET PEPSI COLA® having concentrations in DIET PEPSI COLA® of 6 ppb and 1 ppb. Mixtures were then produced as follows:

(a) 6 ppb damascenone with 6 ppb phenylethyl alcohol in DIET PEPSI COLA®;
(b) 6 ppb damascenone with 1 ppb phenylethyl alcohol in DIET PEPSI COLA®;
(c) 6 ppb β-homocyclocitral (no mixture) in DIET PEPSI COLA®;
(d) 1 ppb β-homocyclocitral (with no additional product) in DIET PEPSI COLA®;
(e) 6 ppb damascenone and 1 ppb β-homocyclocitral in DIET PEPSI COLA®;
(f) 6 ppb β-homocyclocitral with 6 ppb cis-3-hexenol in DIET PEPSI COLA®;
(g) 6 ppb acetophenone with 6 ppb β-homocyclocitral in DIET PEPSI COLA®; and
(h) 6 ppb acetophenone with 1 ppb β-homocyclocitral in DIET PEPSI COLA®.

The mixture of (a) (damascenone admixed with β-phenylethyl alcohol) produced an enhancement and sweetness and removed the bitter aftertaste of DIET PEPSI COLA®.

The mixture of (b) produced a slight increase in sweetness, but completely removed the bitter aftertaste of DIET PEPSI COLA®.

The material of (c) enhanced sweetness and removed bitterness in DIET PEPSI COLA®.

The material of (d) resulted in a very sweet enhancement and complete removal of the bitter aftertaste in DIET PEPSI COLA®.

The mixture of (e) resulted in the removal of bitter aftertaste, but did not enhance sweetness in DIET PEPSI COLA®.

The mixture of (f) increased sweetness and removed the bitter aftertaste in DIET PEPSI COLA®.

The mixture of (g) increased sweetness and removed the bitter taste of DIET PEPSI COLA®.

The mixture of (h) resulted in sweetness enhancement and removal of bitter aftertaste in DIET PEPSI COLA®.

EXAMPLE VIII(F)

A 1% solution of each of the following materials was prepared in 95% food grade ethanol:

(i) massoia lactone having the structure:

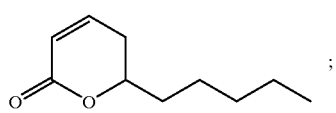

(ii) β-homocyclocitral having the structure:

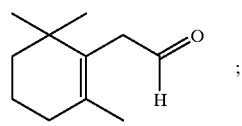

(iii) cis-3-hexenol having the structure:

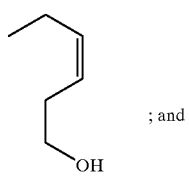

; and (iv) pineapple compound having the structure:

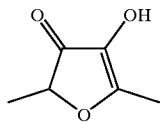

On dilution of each of the 1% solutions in deionized water, a 60 ppm solution was produced. The resulting solutions were then diluted to 6 ppb in DIET PEPSI COLA®. The following mixtures were produced:

(i) pineapple compound at 6 ppb with cis-3-hexenol at 6 ppb in DIET PEPSI COLA®;

(ii) pineapple compound at 6 ppb with β-homocyclocitral at 6 ppb in DIET PEPSI COLA®;

(iii) pineapple compound at 6 ppb with 6 ppb cis-3-hexenol and 6 ppb β-homocyclocitral in DIET PEPSI COLA®;

(iv) massoia lactone at 6 ppb with 6 ppb cis-3-hexenol and 6 ppb β-homocyclocitral in DIET PEPSI COLA®;

(v) 6 ppb massoia lactone with 6 ppb cis-3-hexenol in DIET PEPSI COLA®;

(vi) 6 ppb massoia lactone with 6 ppb β-homocyclocitral in DIET PEPSI COLA®;

(vii) 6 ppb massoia lactone alone (with no admixture) in DIET PEPSI COLA®;

(viii) 6 ppb pineapple compound alone (with no admixture) in DIET PEPSI COLA®; and (ix) 6 ppb massoia lactone with 6 ppb pineapple compound in DIET PEPSI COLA®.

The mixture of (i) (the pineapple compound admixed with cis-3-hexenol) in DIET PEPSI COLA® produced a very sweet enhancement with no bitter aftertaste.

The mixture of (ii) in DIET PEPSI COLA® produced a very sweet enhancement and completely removed the bitter aftertaste.

The mixture of (iii) in DIET PEPSI COLA® resulted in a sweet enhancement and the removal of bitter aftertaste.

The mixture of (iv) in DIET PEPSI COLA® resulted in sweet enhancement and the removal of bitter aftertaste.

The mixture of (v) in DIET PEPSI COLA® resulted in no bitter aftertaste.

The mixture of (vi) in DIET PEPSI COLA® resulted in no bitter aftertaste.

The material of (vii) in DIET PEPSI COLA® removed the bitter aftertaste and increased sweetness in DIET PEPSI COLA®.

The material of (viii) (the pineapple compound) in DIET PEPSI COLA® removed bitter aftertaste to a small extent and did not change the sweetness thereof.

The mixture of (ix) resulted, in DIET PEPSI COLA®, in a slight sweet enhancement, but increased the bitterness.

EXAMPLE IX

BASIC ORAL HYGIENE FLAVOR FORMULATION

The following basic oral hygiene flavor formulation is prepared:

| Ingredients | Parts by Weight |
| --- | --- |
| Peppermint oil | 89.0 |
| Spearmint oil | 2.0 |
| Clove oil | 1.0 |
| Anethol | 2.0 |
| Cardamom oil | 0.1 |
| Wintergreen oil | 5.0 |
| Cinnamic aldehyde | 0.9 |
| Aspartame having the structure: | 0.05 |

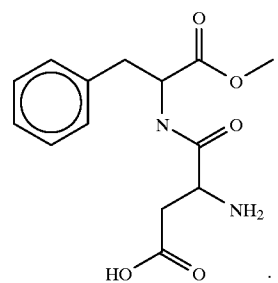

The basic oral hygiene flavor formulation is now divided into two parts. To the first part, the tastand produced according to Example VII is added at the rate of 10%. To the second part, nothing is added. The flavor with the addition of the material produced according to Example VII gives rise to a fresher, sweet, licorice, anise oil-like, spicy aroma and taste characteristic. The peppermint characteristics also appear to be enhanced. The flavor without the tastand composition of Example VII has a bitter aftertaste. Accordingly, the tastand-containing composition is preferred by a five member bench panel.

EXAMPLE X

LICORICE CHEWING STICK

A flexible licorice stick is prepared in a standard manner. Prior to hardening at the level of 0.05 ppm, aspartame having the structure:

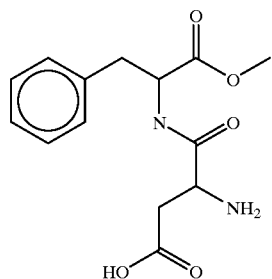

is added to the molten mixture. Also prior to hardening at the level of 6 ppb, the tastand composition of Example VII is added to the molten mixture. The molten mixture is molded into licorice sticks and hardened for marketing. Each of the licorice sticks has a pleasant, powerful, natural-like licorice anisic, China star anise oil flavor. None of the licorice sticks have a bitter aftertaste. In the absence of the tastand produced according to Example VII, each of the licorice sticks, on consumption, has a bitter aftertaste. Furthermore, the natural sweetness of each of the licorice sticks is enhanced as a result of the use of a tastand of Example VII.

What is claimed is:

1. Apparatus for carrying out the production of a natural tastand or food additive comprising:
   (i) harvesting means for harvesting a plurality of sugarcane stalks which bear a plurality of cane stalk leaves;
   (ii) first conveying means for conveying said plurality of sugarcane stalks to leaf removal means;
   (iii) leaf removal means proximate said first conveying means for removing a plurality of leaves from said sugarcane stalks in order to provide a plurality of cane stalk leaves;
   (iv) second conveying means for conveying said cane stalk leaves to macerating means;
   (v) macerating means for macerating at least a finite portion of said cane stalk leaves in order to produce a composition comprising macerated cane stalk leaves;
   (vi) third conveying means for conveying said macerated cane stalk leaves to extraction means;
   (vii) extraction means for causing cane stalk leaves, including macerated cane stalk leaves, to be in intimate contact with an aqueous vapor over a prolonged period of time in order to form an aqueous vapor-tastand or food additive composition in the vapor phase;
   (viii) vapor condensing means for condensing said vapor phase aqueous vapor-tastand or food additive composition whereby a liquid phase aqueous tastand or food additive composition is formed; and
   (ix) physical separation means for carrying out a physical separation unit operation on said liquid phase aqueous tastand or food additive composition whereby said natural tastand or food additive composition is isolated.

2. Apparatus for producing a natural tastand or food additive comprising:
   (i) harvesting means for harvesting a plurality of sugarcane stalks which bear a plurality of cane stalk leaves;
   (ii) leaf stripping means for removing a plurality of leaves from said harvested sugarcane stalks immediately after harvesting whereby a plurality of cane stalk leaves is provided;
   (iii) first conveying means for conveying said plurality of cane stalk leaves to macerated means;
   (iv) proximate said first conveying means, macerated means for macerating at least a finite portion of said cane stalk leaves to produce a composition comprising macerated cane stalk leaves;
   (v) second conveying means for conveying cane stalk leaves and macerated cane stalk leaves to hydraulic pressurization means;
   (vi) proximate said second conveying means, hydraulic pressurization means for applying 2,000–5,000 psig pressure to said cane stalk leaves including macerated cane stalk leaves over an extended period of time in order to separate aqueous tastand or food additive composition from the cane stalk leaves including macerated cane stalk leaves; and
   (vii) physical separation means for carrying out a physical separation unit operation on said tastand or food additive composition whereby said natural tastand or food additive composition is formed.

3. The apparatus of claim 1 wherein the extraction means (vii) is steam distillation means.

4. The apparatus of claim 1 wherein the physical separation means (ix) is supercritical carbon dioxide extraction means.

5. The apparatus of claim 1 having additional means (x) for adsorption of said natural tastand or food additive composition onto a material selected from the group consisting of:
   (a) activated charcoal;
   (b) resin; and
   (c) zeolites.

6. The apparatus of claim 2 wherein the physical separation means (vii) is fractional distillation means.

7. The apparatus of claim 2 wherein the physical separation means (vii) is supercritical carbon dioxide extraction means.

8. The apparatus of claim 2 having additional means (viii) for adsorption of said natural tastand or food additive composition onto a material selected from the group consisting of:
   (a) activated charcoal;
   (b) resin; and
   (c) zeolites.

* * * * *